US008962532B2

(12) United States Patent
Shapiro et al.

(10) Patent No.: US 8,962,532 B2
(45) Date of Patent: Feb. 24, 2015

(54) PROGRAMMABLE ITERATED ELONGATION: A METHOD FOR MANUFACTURING SYNTHETIC GENES AND COMBINATORIAL DNA AND PROTEIN LIBRARIES

(75) Inventors: Ehud Y. Shapiro, Nataf (IL); Gregory Linshiz, Rehovot (IL); Tuval Ben-Yehezkel, Ramat Gan (IL); Shai Kaplan, Rehovot (IL); Rivka Adar, Carmai Yosef (IL); Ilan Gronau, Haifa (IL); Sivan Tuvi, Tel-Aviv (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 458 days.

(21) Appl. No.: 12/308,557

(22) PCT Filed: Jun. 19, 2007

(86) PCT No.: PCT/IL2007/000747
§ 371 (c)(1),
(2), (4) Date: Aug. 25, 2009

(87) PCT Pub. No.: WO2007/148337
PCT Pub. Date: Dec. 27, 2007

(65) Prior Publication Data
US 2010/0240538 A1 Sep. 23, 2010

Related U.S. Application Data

(60) Provisional application No. 60/814,570, filed on Jun. 19, 2006, provisional application No. 60/924,042, filed on Apr. 27, 2007.

(51) Int. Cl.
*G06F 19/20* (2011.01)
*C12Q 1/68* (2006.01)
(Continued)

(52) U.S. Cl.
CPC ............ *C12N 15/1089* (2013.01); *C12Q 1/686* (2013.01); *C12N 15/1031* (2013.01); *C12N 15/66* (2013.01); *C40B 50/02* (2013.01); *G06F 19/22* (2013.01)
USPC .......................................... 506/24; 435/6.12

(58) Field of Classification Search
CPC .... C12N 2320/50; C12N 15/66; G06F 19/10; G06F 19/20; G06F 19/22; C40B 50/02; C12Q 1/686
See application file for complete search history.

(56) References Cited

U.S. PATENT DOCUMENTS 5,804,373 A 9/1998 Schweitzer et al.
6,266,569 B1 7/2001 Shapiro et al.
(Continued)

FOREIGN PATENT DOCUMENTS

WO 2006044956 4/2006

OTHER PUBLICATIONS

PCT Search Report for corresponding PCT application PCT/IL2007/000747 transmitted on Aug. 13, 2008.
(Continued)

*Primary Examiner* — Christopher M. Babic
*Assistant Examiner* — Jeremy C Flinders
(74) *Attorney, Agent, or Firm* — Graeser Associates International Inc; Dvorah Graeser

(57) ABSTRACT

A method for manufacturing synthetic genes and combinatorial DNA and protein libraries, termed here Divide and Conquer-DNA synthesis (D&C-DNA synthesis) method. The method can be used in a systematic and automated way to synthesize any long DNA molecule and, more generally, any combinatorial molecular library having the mathematical property of being a regular set of strings. The D&C-DNA synthesis method is an algorithm design paradigm that works by recursively breaking down a problem into two or more sub-problems of the same type. The division of long DNA sequences is done in silico. The assembly of the sequence is done in vitro. The D&C-DNA synthesis method protocol consists of a tree, in which each node represents an intermediate sequence. The internal nodes are created in elongation reactions from their daughter nodes, and the leaves are synthesized directly. After each elongation only one DNA strand passes to the next level in the tree until receiving the final product. Optionally and preferably, error correction is performed to correct any errors which may have occurred during the synthetic process.

9 Claims, 62 Drawing Sheets

(51) Int. Cl.
*C12N 15/10* (2006.01)
*C12N 15/66* (2006.01)
*C40B 50/02* (2006.01)
*G06F 19/22* (2011.01)

(56) References Cited

U.S. PATENT DOCUMENTS

| | | | |
|---|---|---|---|
| 2002/0119458 A1 | 8/2002 | Suyama et al. | |
| 2004/0077090 A1 | 4/2004 | Short | |
| 2004/0152108 A1 | 8/2004 | Keith et al. | |
| 2004/0224345 A1 | 11/2004 | Vandersall et al. | |
| 2007/0250497 A1 | 10/2007 | Mansfield et al. | |
| 2007/0269870 A1* | 11/2007 | Church et al. | 435/91.2 |
| 2008/0318795 A1* | 12/2008 | Selifonov et al. | 506/1 |
| 2011/0021361 A1* | 1/2011 | Chetverin et al. | 506/7 |

OTHER PUBLICATIONS

IPRP for corresponding PCT application PCT/IL2007/000747 transmitted on Mar. 17, 2009.
Supplementary Search Report for corresponding EP application 07736483.4 transmitted on Feb. 16, 2010.
Yingfeng et al., 2005, Applied Microbiology and Biotechnology, A rapid and efficient method for multiple-site mutagenesis with a modified overlap extension PCR.
Kodumal et al., 2004, PNAS, Total synthesis of long DNA sequences: Synthesis of a contiguous 32-kb polyketide synthase gene cluster.
Xiong et al. 2004, Nucleic Acid Research, A simple rapid high fidelity and cost effective PCR-based two step DAN synthesis method for long gene sequences.
Hoover et al., 2002, Nucleic Acid Research, DNAWorks: an automated method for designing oligonucleotides for PCR-based gene synthesis.
Yee et al., 1998, Proceedings international conference on intelligent systems for molecular biology, Automated clustering and assembly of large EST collections.
Adelman Leonard M., 1994, Science, Molecular Computation of Solutions to Combinatorial Problems.
Braich et al., 2001, DNA Computing—Lecture Notes in Computer Science, Solution of a Satisfiability Problem on a Gel-Based DNA Computer.
Braich et al., 2002, Science, Solution of a 20-Variable 3-SAT Problem on a DNA Computer.
Ben Yehezkel et al., 2008, Nucleic Acid Research, De novo DNA synthesis using single molecule PCR.
Barany F., 1991, PNAS, Genetic disease detection and DNA amplification using cloned thermostable ligase.
Office Action for corresponding EP application 07736483.4 issued on Mar. 8, 2012.
Binkowski B F et al: "Correcting errors in synthetic DNA through consensus shuffling", Nucleic Acids Research Special Publication, Oxford University Press, Surrey, GB, vol. 33, No. 6, Mar. 30, 2005, pp. 1-8, XP002368229, ISSN: 0305-1048, DOI: 10.1093/NAR/GNI053.
Carr P A et al: "Protein-mediated error correction for de novo DNA synthesis", Nucleic Acids Research Special Publication, Oxford University Press, Surrey, GB, vol. 32, No. 20, Nov. 23, 2004, pp. 1-9, XP002368230, ISSN: 0305-1048, DOI: 10.1093/NAR/GKH560.
Linshiz Gregory et al: "Recursive construction of perfect DNA molecules from imperfect oligonucleotides", Molecular Systems Biology, vol. 4, May 2008, XP002568816.
Office Action for corresponding EP application 07736483.4 issued on Jun. 8, 2011.
Office action for corresponding EP application 12167464 issued on Jun. 28, 2012.
Ben Yehezkel Tuval et al: "De novo DNA synthesis using single molecule PCR", Nucleic Acids Research, vol. 36, No. 17, Oct. 2008, XP002568817, ISSN: 0305-1048.
Office Action for corresponding EP application 12167464 issued on Apr. 8, 2013.
Office Action for corresponding EP application 12167464 issued on Oct. 23, 2013.
Kunkel, T. Rapid and efficient site-specific mutagenesis without phenotypic selection. Proc Natl Acad Sci U S A 82, 488-492 (1985).
Ho, S. et al., Site-directed mutagenesis by overlap extension using the polymerase chain reaction. Gene 77, 51-59 (1989).
Landt, O., et al. A general method for rapid site-directed mutagenesis using the polymerase chain reaction. Gene 96, 125-128 (1990).
Cirino, P., et al. Generating mutant libraries using error-prone PCR. Methods Mol Biol 231, 3-9 (2003).
Stemmer, W, et al. Single-step assembly of a gene and entire plasmid from large numbers of oligodeoxyribonucleotides. Gene 164, 49-53 (1995).
Wilson, G. Cloned restriction-modification systems—a review. Gene 74, 281-289 (1988).
Wilson, G. et al. Restriction and modification systems. Annu Rev Genet 25, 585-627 (1991).
Hartley, J., et al. DNA cloning using in vitro site-specific recombination. Genome Res 10, 1788-1795 (2000).
Li, M. et al. Harnessing homologous recombination in vitro to generate recombinant DNA via SLIC. Nat Methods 4, 251-256 (2007).
Au, L, et al. Gene synthesis by a LCR-based approach: high-level production of leptin-L54 using synthetic gene in *Escherichia coli*. Biochem Biophys Res Commun 248, 200-203 (1998).
Smith, H., et al. Generating a synthetic genome by whole genome assembly: phiX174 bacteriophage from synthetic oligonucleotides. Proc Natl Acad Sci U S A 100, 15440-15445 (2003).
Xiong, A. et al. PCR-based accurate synthesis of long DNA sequences. Nat Protoc 1, 791-797 (2006).
Horton, R., et al. Engineering hybrid genes without the use of restriction enzymes: gene splicing by overlap extension. Gene 77, 61-68 (1989).
Coco, W. et al. DNA shuffling method for generating highly recombined genes and evolved enzymes. Nat Biotechnol 19, 354-359 (2001).
Gaytán, P., et al. Combination of DMT-mononucleotide and Fmoc-trinucleotide phosphoramidites in oligonucleotide synthesis affords an automatable codon-level mutagenesis method. Chem Biol 5, 519-45 527 (1998).
Merkle, R.C. Convergent assembly. Nanotechnology 8, 18-22 (1997).
International search report and written opinion for PCT/IL2008/001629 dated Jul. 23, 2009.
Tian et al., Accurate multiplex gene synthesis from programmable DNA microchips. Nature 432(7020):1050-4 (2004).
Office Action for related EP application 12167464 issued on Jun. 30, 2014.

* cited by examiner

| | |
|---|---|
| Amp_PCR1-PCR4<br>ELONG3F-Prm1F<br>E3-F | ATGAGTATTCAACATTTCCGTGTCGCCCTTATTCCCTTTTTTGCGGCATTTTGCCTTCCT<br>----------------------GTCGCCCTTATTCCCTTTTTTGCGGCATTTTGCCTTCCT |
| Amp_PCR1-PCR4<br>ELONG3F-Prm1F<br>E3-F | GTTTTTGCTCACCCAGAAACGCTGGTGAAAGTAAAAGATGCTGAAGATCAGTTGGGTGCA<br>GTTTTTGCTCACCCAGAAACGCTGGTGAAAGTAAAAGATGCTGAAGATCAGTTGGGTGCA |
| Amp_PCR1-PCR4<br>ELONG3F-Prm1F<br>E3-F | CGAGTGGGTTACATCGAACTGGATCTCAACAGCGGTAAGATCCTTGAGAGTTTTCGCCCC<br>CGAGTGGGTTACATCGAACTGGATCTCAACAGCGGTAAGATCCTTGAGAGTTTTCGCCCC<br>--------------------GGTAAGATCCTTGAGAGTTTTCGCCCC<br>*********************** |
| Amp_PCR1-PCR4<br>ELONG3F-Prm1F<br>E3-F | GAAGAACGTTTTCCAATGATGAGCACTTTTAAAGTTCTGCTATGTGGCCGCGGTATATCC<br>GAAGAACGTTTTCCAATGATGAGCACTTTTAAAGTTCTGCTATGTGGCCGCGGTATATCC<br>GAAGAACGTTTTCCAATGATGAGCACTTTTAAAGTTCTGCTATGTGGCCGCGGTATATCC<br>*********************** |
| Amp_PCR1-PCR4<br>ELONG3F-Prm1F<br>E3-F | CGTATTGACGCCGGGCAAGAGCAACTCGGTCGCCGCATACACTATTCTCAGAATGACTTG<br>CGTATTGACGCCGGGCAAGAGCAACTCGGT--------------------------------<br>CGTATTGACGCCGGGCAAGAGCAACTCGGTCGCCGCATACACTATTCTCAGAATGACTTG<br>*********************** |
| Amp_PCR1-PCR4<br>E3-F | GTTGAGTGCTGCCATAACCATGAGTGATAACACTGCGGCCAACTTACTTCTGACAACGATC<br>GTTGAGTGCTGCCATAACCATGAGTGATAACACTGCGGCCAACTTACTTCTGACAACGATC |

FROM FIGURE 18A

```
Amp_PCR1-PCR4    TGCAGTGCTGCCATAACCATGAGTGATAACACTGCGGCCAACTTACTTCTGACAACGATC
E3-F             TGCAGTGCTGCCATAACCATGAGTGATAACACTGCGGCCAACTTACTTCTGACAACGATC

Amp_PCR1-PCR4    GGAGGACCGAAGGAGCTAACCGCTTTTTGCACAACATGGGGGATCATGTAACTCGCCTT
E3-F             GGAGGACCGAAGGAGCTAACCGCTTTTTGCACAACATGGGGGATCATGTAACTCGCCTT

Amp_PCR1-PCR4    GATCGTTGGGAACCGGAGCTGAATGAAGCCATACCAAACGACGAGCGTGACACCACGATG
E3-F             GATCGTTGGGAACCGGAGCTGAATGAAGCCATACCAAACGACGAGCGTGACACCACGATG

Amp_PCR1-PCR4    CCTGTAGCAATGGCAACAACGTTGCGCAAACTATTAACTGGCAACTACTACTCTAGCT
E3-F             CCTGTAGCAATGGCAACAACGTTGCGCAAACTATTAACTGGCAACTACTACTCTAGCT

Amp_PCR1-PCR4    TCCCGGCAACAATTAATAGACTGGATGGAGGCGGATAAAGTTGCAGGACCACTTCTGCGC
E3-F             TCCCGGCAACAATTAATAGACTGGATGGAGGCGGATAAAGTTGCAGGACCACTTCTGCGC

Amp_PCR1-PCR4    TCGGCCCTTCCGGCTGGCTGGTTATTGCTGATAAATCTGGAGCCGGTGAGCGTGGGTCT
E3-F             TCGGCCCTTCCGGCTGGCTGGTTATTGCTGATAAATCTGGAGCCGGTGAGCGTGGGTCT

Amp_PCR1-PCR4    CGCGGTATCATTGCAGC-
E3-F             CGCGGTATCATTGCAGCA
```

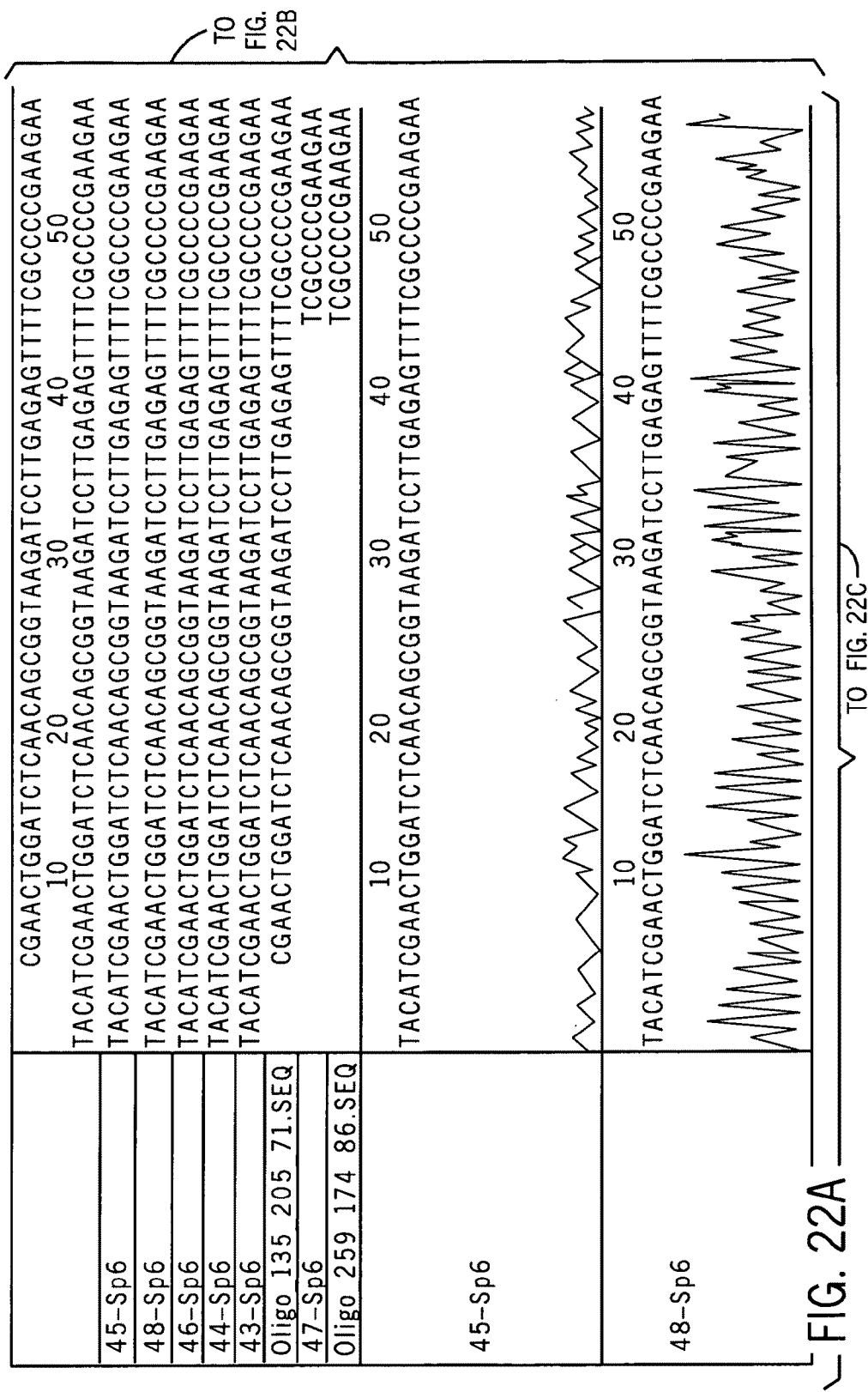

TO FIGURE 26B

FROM FIGURE 26A

C. CLONING AND SEQUENCING (~12 HOURS)

TARGET CLONES WITH ERRORS

D. COMPUTING MINIMAL CUT IN SILICO (~2 HOURS)

AMPLIFICATION OF ERROR-FREE FRAGMENTS FROM CLONES (~1.5 HOURS)

RECURSIVE RECONSTRUCTION IN VITRO (~6 HOURS)

TARGET GFP MOLECULE WITH NO ERRORS

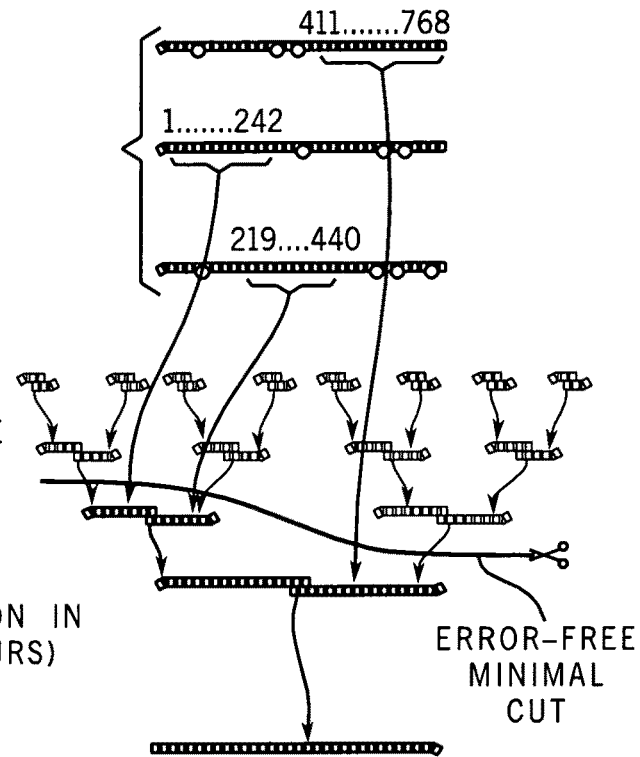

ERROR-FREE MINIMAL CUT

E. NATURAL & SYNTHETIC INPUT DNA

RECURSIVE RECONSTRUCTION OF 3Kb FRAGMENT

TARGET 3Kb MOLECULE WITH NO ERRORS

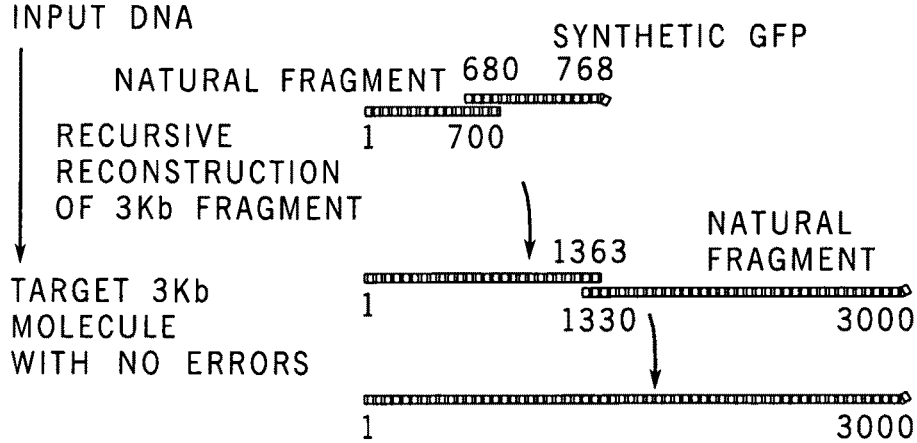

FIG. 26B

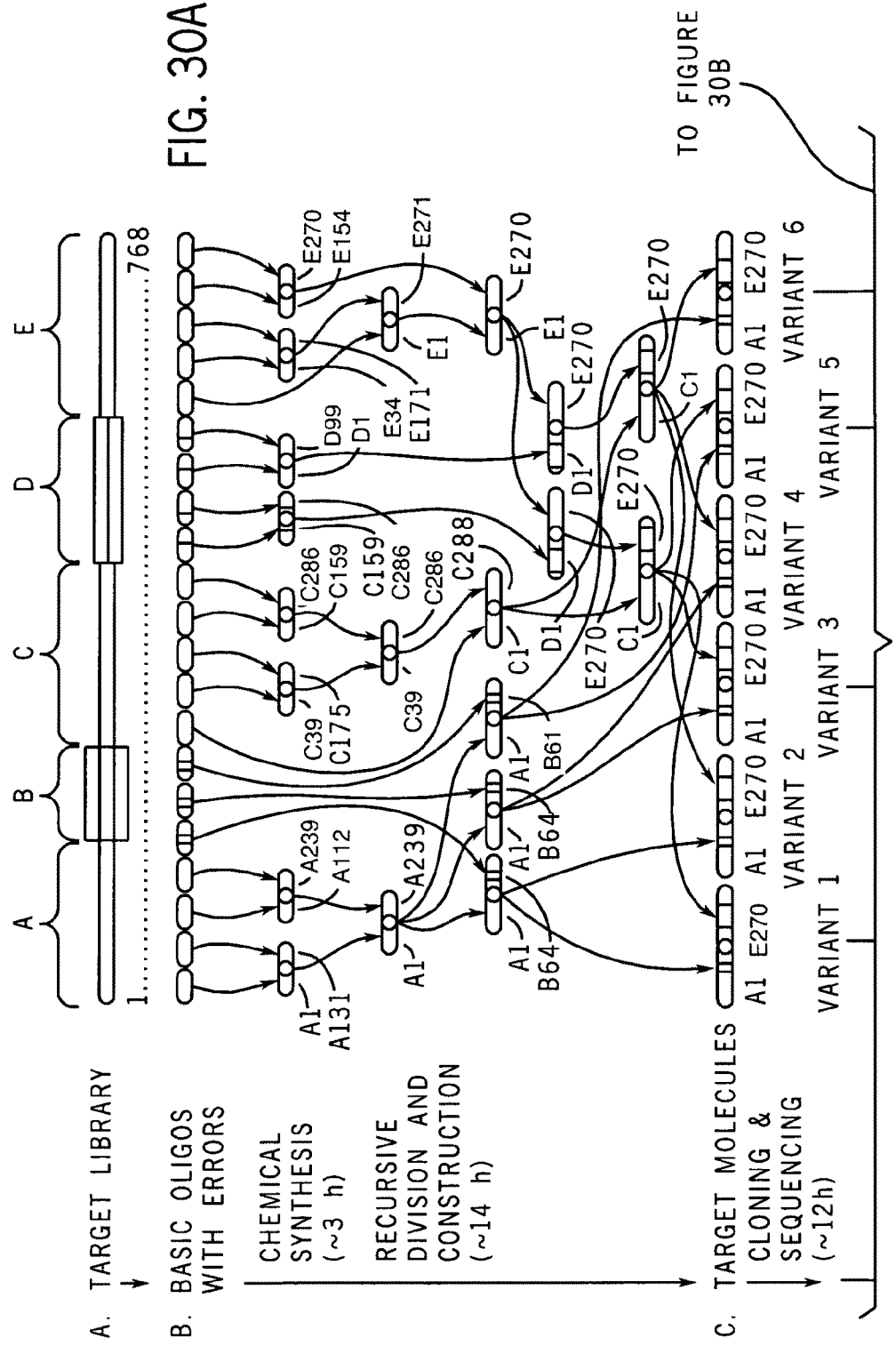

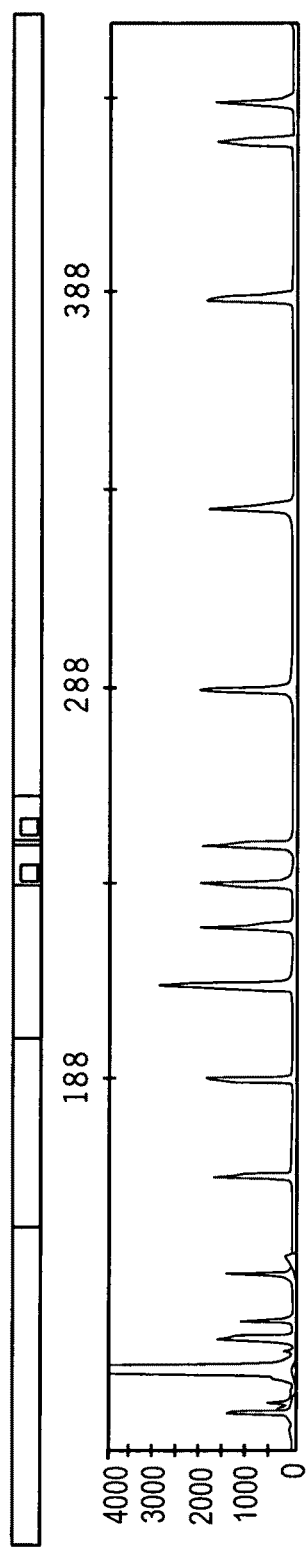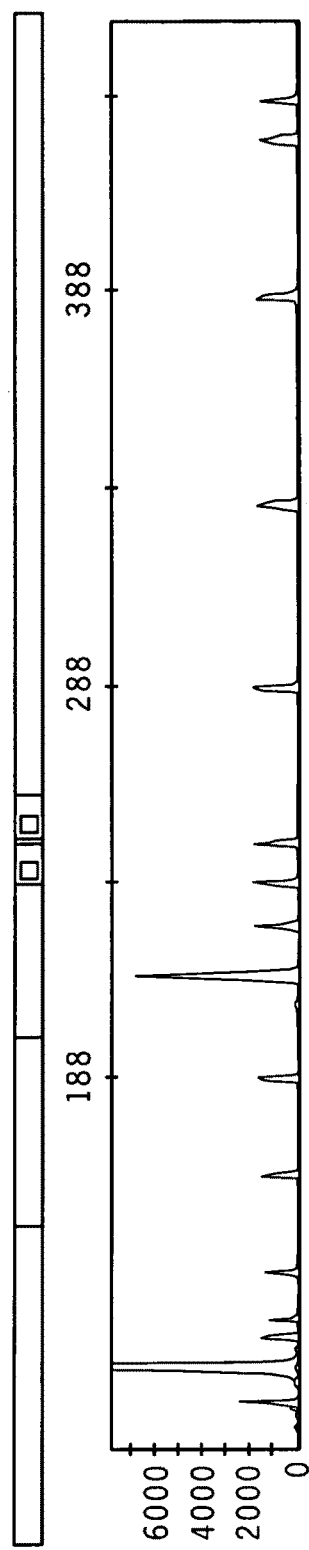
FIG. 31Ac

US 8,962,532 B2

PROGRAMMABLE ITERATED ELONGATION: A METHOD FOR MANUFACTURING SYNTHETIC GENES AND COMBINATORIAL DNA AND PROTEIN LIBRARIES

This Application is a national phase of and claims priority from, PCT Application No. PCT/IL2007/000747, filed on Jun. 19 2007, which claims priority from U.S. Provisional Application No. 60/814,570, filed on Jun. 19 2006, and from U.S. Provisional Application No. 60/924,042, filed on Apr. 27 2007, all of which are hereby incorporated by reference as if fully set forth herein.

FIELD OF THE INVENTION

The present invention is a system and method for constructing physical objects, including but not limited to polymers such as polynucleotides and polypeptides, and libraries thereof, preferably automatically but optionally at least semi-automatically.

BACKGROUND OF THE INVENTION

Advances in the technology of oligodeoxyribonucleotide (ODN) synthesis and purification have led to opportunities for de novo gene synthesis. There are two major approaches to the construction of a synthetic gene. The first approach involves the synthesis of ODNs comprising the entire sequence. ODNs are annealed in a piecemeal fashion followed by joining with DNA ligase[i]. The DNA fragments are then cloned into a plasmid vector either directly or after amplification by PCR. The second approach is a PCR-based method[ii] in which multiple ODNs belonging to the two strands of the gene sequence concerned are annealed by short overlaps and then extended by a thermal-stable polymerase using overlapped regions as primers. Synthetic genes sequences can be optimized for maximal expression by eliminating rare codons and utilizing optimal codons for a particular species or for multiple host systems, sequence optimization of transcription and translation initiation/termination region, modification of messenger stability, minimizing secondary structure and adjusting GC content. Existing restriction sites can be removed and/or new restriction sites can be added to prepare the gene for future cloning strategies.

Another example of a method for gene assembly involves solid-phase technology, as described by Stahl et al., in "Solid Phase Gene Assembly of Constructs Derived from the *Plasmodium falciparum* Malaria Blood-Stage Antigen Ag332"[iii] The oligonucleotide is synthesized while attached to a solid support. The synthetic procedure uses ligases rather than polymerase, in order to link preformed DNA segments. A similar method was described by Hostomsky et al., in "Solid Phase Assembly of Cow Colostrum Trypsin Inhibitor Gene"[iv]. The authors noted that the yields of full-length oligonucleotides decrease substantially as the length of the oligonucleotide (synthesized gene) increases. This result would be expected for any oligonucleotide/gene assembly process which uses ligase, because there is no proofreading function. Furthermore, there is no possibility to increase the yield by allowing additional cycles of ligation to be performed, such that yields of correctly formed oligonucleotides of the proper length would be expected to drop sharply as the length of the desired oligonucleotide increased.

U.S. Pat. No. 6,386,861 also describes a method for creating a library of DNA oligonucleotides, by recombining or "shuffling" families of oligonucleotides. However, rather than creating the library according to a set of mathematically defined principles, the library is only created according to homology with a previously defined sequence or group of sequences, thereby limiting the scope of the libraries which may be created by using this method.

SUMMARY OF THE INVENTION

The background art does not teach or suggest a method or system for recursively constructing a physical object from a plurality of subcomponents. The background art also does not teach or suggest such a method or system for constructing a library containing a plurality of physical objects.

The background art also does not teach or suggest a method or system for constructing such a physical object that is error free or at least has reduced errors, from a plurality of subcomponents of which at least one has at least one error. The background art also does not teach or suggest such a method or system for constructing a library containing a plurality of physical objects.

The background art also does not teach or suggest a method or system for straightforward, easily automated, manufacture of synthetic DNA longer than 100 nucleotides (nts). The background art also does not teach or suggest a method for the systematic synthesis of a combinatorial DNA or protein library from a plurality of defined specifications or characteristics.

The present invention overcomes these deficiencies of the background art by providing a system and method for constructing a final object from a plurality of subcomponents, in an efficient manner which is optionally and preferably capable of being at least partially automated and more preferably completely automated. The present invention also features, in some embodiments, a system and method for constructing a library of such final objects.

According to some embodiments of the present invention, there is provided a hierarchical, recursive construction process, preferably a modified recursive construction process, for constructing a final object from a plurality of subcomponents. These subcomponents are used to produce the final object. The process is preferably "modified recursion" because the type of the final object may optionally be different from the type of input subcomponents. Optionally and preferably, the input and output of each subprocess within the construction process may be of a different type. In recursive construction, pairs of smaller elements (or optionally groups of at least three smaller elements) are composed systematically into ever larger elements until the target element is constructed. A prerequisite of mathematically strict recursive construction is that the output of the composition operation be of the same type as its two or more inputs. However, as noted the present invention may optionally feature recursive or modified recursive construction, such that the final object may optionally be of a different type from one or more of the subcomponents and/or the output of each subprocess may optionally be of a different type from one or more inputs to the subprocess.

According to preferred embodiments of the present invention, at least one subcomponent may optionally be erroneous or at least potentially erroneous, such that at least one erroneous or potentially erroneous subcomponent is used in the construction process which is then preferably adjusted to overcome such an error or potential error. In general, a composite object constructed from error-prone building blocks is expected to have a higher number of errors than each of its building blocks. However, if errors are randomly distributed among the building blocks and occur randomly during construction, and if sufficiently many copies of an object are constructed, it is expected that some of the copies may contain error-free components. If such components could be identified and extracted from the faulty objects, they could be re-used as building blocks for another recursive construction of the object. Since this construction starts from typically larger building blocks that are error-free, the number of errors in the resulting object is expected to decrease, possibly down to zero. Even if the objects produced this way would have errors, they are expected to have fewer errors than their predecessors and hence to have even larger error-free components, which can be used as building blocks for a subsequent corrective recursive construction, until an error-free (or at least reduced error) object is preferably formed.

According to some embodiments of the background art, the system and method are for at least semi-automatically, but preferably automatically, manufacturing synthetic genes and combinatorial DNA and protein libraries, or any other biological polymer. The method can be used in a systematic and automated manner to synthesize any long DNA molecule, or other biological polymer, and, more generally, any combinatorial molecular library having a plurality of biological polymer molecules which optionally have the mathematical property of being a regular set of strings.

Much of molecular biology research requires DNA molecules, or other biopolymers, prepared to specification. While there is a standard automated method for preparing DNA oligonucleotides around 100 nts$^v$, longer DNA molecules and molecular libraries are typically prepared through a multitude of ad hoc, labor-intensive methods as previously described in the background section above. There is neither a common language for specifying DNA libraries and/or longer DNA molecules, nor a general-purpose, automated method to prepare these libraries and/or longer molecules.

It should be noted that these processes are preferably performed at least semi-automatically, and more preferably completely automatically. The hybrid process is amenable to end-to-end automation, taking as input a mathematical specification and producing as output the specified molecules, and as such has the potential of transforming the nature and pace of molecular biology research.

According to preferred embodiments of the present invention, there is provided a method for recursive construction of a polynucleotide. The method is preferably automated. The method preferably operates in a hierarchical manner, by first calculating the hierarchical building blocks required to construct the polynucleotide and then constructing the polynucleotide from the building blocks in an order determined according to the hierarchy. Optionally, a plurality of construction processes may be performed in parallel, the resultant blocks of which may optionally and preferably be used to construct the final molecule (in which case more preferably two such parallel processes are used). The complete set of reactions is preferably expressed as a hierarchical tree and the complete set of reactions for error correction is more preferably determined according to a minimal cut algorithm.

The method also preferably uses perfect building blocks, although imperfect building blocks may optionally be used at an intermediate stage. Imperfect building blocks may be used initially, but perfect building blocks are preferably obtained from the imperfect building blocks and then used to directly construct the polynucleotide.

According to preferred embodiments of the present invention, there is provided a method for reducing if not eliminating errors which occur during polynucleotide synthesis, preferably through an iterative error elimination process. Such a process is preferably performed as part of a recursive process of oligonucleotide construction. Recursive construction with iterative error elimination improves on previous approaches to DNA synthesis by enabling rapid, fully-automated and error-free construction of long DNA molecules. Such a method may also optionally be used to combine synthetic and natural DNA segments. Furthermore, such a method optionally enables efficient design, synthesis and error correction of combinatorial DNA libraries with shared and variant components. Optionally, such a method could be used for synthesizing new\synthetic\artificial genomes.

Optionally and preferably, a library (or any other collection of polynucleotide molecules having at least one variable region and at least one shared region) is constructed by first analyzing the plurality of polynucleotide sequences to create a set of building blocks according to the shared and variable regions, and then constructing in parallel each molecule in the library from the building blocks.

According to other preferred embodiments, the method of the present invention may optionally be used to prepare a library of variants of a DNA sequence using any naturally existing nucleic acids (e.g. plasmid, cDNA etc.) related to that sequence as input. For example, in order to generate different variants of a gene in the form of a variant library for the gene, the method of the present invention may optionally use the DNA of the gene itself as the starting material for library construction.

As used herein, the term "combinatorial molecular library" preferably includes a plurality of biological polymers, and more preferably includes a large number of such biological polymers which represent many different combinations of the building blocks of the biological polymers.

Hereinafter, the term "long oligonucleotide" preferably includes an oligonucleotide of at least about 100 bases in length, more preferably includes an oligonucleotide of at least about 200 bases in length and most preferably includes an oligonucleotide of at least about 400 bases in length.

BRIEF DESCRIPTION OF THE DRAWINGS

The invention is herein described, by way of example only, with reference to the accompanying drawings, wherein:

FIG. 4A shows the basic recursive process for D&C-DNA synthesis, while FIG. 4B shows a process for determining the optimal synthesis protocol(s);

FIG. 18 shows the sequence alignment of the obtained elongation 3 product with the expected sequence, including the following sequences: Amp pcr1-pcr4 (SEQ ID NO:1); Eong3f-prm1f (SEQ ID NO:2); and E3-f (SEQ ID NO:3).

FIG. 30, parts B and C, shown in FIG. 30, and part D, shown in FIG. 30B show a graph depicting the library construction process corresponding to D&C based in silico division; target library sequences were recursively divided into shared and unique components and then further divided into basic oligonucleotides using D&C. These oligo sequences were made (with errors) by conventional chemical oligo synthesis. Using in vitro recursive construction with these oligos as input, error prone approximations of all six target p53 library molecules were composed. These p53 variants were cloned, sequenced and errors were identified (marked red). An error free minimal cut (below black line, non faded) of the original library construction plan was computed from only four error prone clones (variants 1, 3, 5, 6) for all six library variants. Error free segments out of these four clones (delimited) were used as input for the error free recursive reconstruction of all six target library members across clones and across variants according to the computed minimal cut graph;

FIG. 37 shows gel electrophoresis of DNA from single molecule PCR with recursively constructed synthetic gene that codes for GFP as template.

DESCRIPTION OF THE PREFERRED EMBODIMENTS

Figure 1:
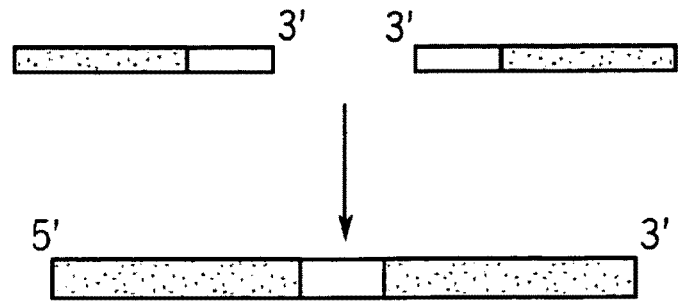
FIG. 1 shows recursive synthesis for use in the method of the present invention.

According to some embodiments of the present invention, there is provided a hierarchical, recursive construction process, preferably a modified recursive construction process, for constructing a final object from a plurality of subcomponents. These subcomponents are used to produce the final object. The process is preferably "modified recursion" because the type of the final object may optionally be different from the type of input subcomponents. Optionally and preferably, the input and output of each subprocess within the construction process may be of a different type. In recursive construction, pairs of smaller elements (or optionally groups of at least three smaller elements) are composed systematically into ever larger elements until the target element is constructed. A prerequisite of mathematically strict recursive construction is that the output of the composition operation be of the same type as its two or more inputs. However, as noted the present invention may optionally feature recursive or modified recursive construction, such that the final object may optionally be of a different type from one or more of the subcomponents and/or the output of each subprocess may optionally be of a different type from one or more inputs to the subprocess.

The subcomponents may optionally be of one type or alternatively of a plurality of types. By "type" it is meant a category of subcomponents rather than a particular instance thereof. A non-limiting example of a type is a type of a polymer or a type of a unit of a polymer. Non-limiting examples of such types include amino acids, nucleotides, polynucleotide, oligonucleotide, peptide, polypeptide, double stranded or single stranded DNA or RNA and/or any type of functional group and/or molecule, or combinations thereof. According to some embodiments of the present invention, the type is preferably double stranded or single stranded DNA or RNA, or combinations thereof. Other non-limiting examples of a type are an electrical component, including (without limitation) any component of an electronic device, or any combinatorial molecular library having the mathematical property of being a regular set of strings.

According to preferred embodiments of the present invention, the process for recursively constructing the final object is preferably determined at least partially automatically, by determining an efficient path for combining a plurality of subcomponents. By "efficient" it is meant that at least one of a majority of sub-processes for combining a plurality of subcomponents is preferred according to one or more criteria of time, energy input, by-products and monetary expense, and/or that the least number of subcomponents and/or sub-processes are required for preparing the final object.

Preferably, the efficient path is determined according to the "divide and conquer" method as described herein or a variation thereof. The divide and conquer method starts with the final object and then decomposes it to a plurality of subcomponents. The method searches for an optimal protocol for the construction of the target object under a set of constraints and a set of cost parameters. The method preferably features an optimal or at least efficient decomposition of the final object as provided by the user to a plurality of subcomponents, which can then preferably be assembled and/or combined to the final object according to one or more subprocesses, each of which has a protocol. This decomposition process is preferably performed iteratively a plurality of times, such that one or more subcomponents of subprocesses which are performed subsequently in the construction process are preferably assembled and/or constructed through earlier subprocesses.

According to preferred embodiments of the present invention, the decomposition process preferably includes searching for an optimal and valid division point of the final object. Such a point preferably fulfills a set of constraints such as the existence of specific subcomponents and overlap specificity for the division point, in addition to the existence of two valid protocols which may build the two divided parts. Once a valid division point is found the algorithm recursively searches a protocol to build its two parts. The recursion preferably stops when the target object has fulfilled one or more requirements. A cost function is computed for each sub-protocol based on the number of subcomponents and their costs thereof, the number of reactions and the number of protocol tree levels required to build its target. The smallest cost protocol is selected as the optimal protocol. Since the protocol space is very large, a dynamic programming algorithm is preferably used to keep previously computed sub-protocols in a cache which are then preferably reused when needed in a different search path. In addition, a branch and bound algorithm is preferably used to trim the search space when the intermediate cost show that the current best cost for a protocol cannot be improved.

Examples of constraints and a set of cost parameters for polynucleotide synthesis include the preference for the subcomponents to be synthesizable as oligo primers, size of oligonucleotides, number of oligonucleotides, number of reactions (as an example of the number of subprocesses), number of levels in the construction hierarchy, binding specificity, binding affinity whether the subcomponents, such as oligonucleotides, are ready for use or whether they must be prepared, and use of synthetic or natural DNA or RNA. Other parameters which may optionally be generalized for any type of construction process include energy input and any cost or difficulty in each of the subprocesses. Some of the above specific parameters may also optionally be generalized for other types of final objects, including but not limited to, number of subprocesses, number of levels in the construction hierarchy, size and/or other cost involved in creating the subcomponents, number of subcomponents and whether the subcomponents are ready for use or alternatively must be prepared.

According to an embodiment of the present invention, recursive construction (or optionally modified recursive construction) may optionally be used for construction of a library comprising a plurality of final objects. The algorithm receives a library description with variable regions and/or aspects separated by shared regions and/or aspects of the final objects. Each variable region may have two or more variants with one or more different properties. Optionally and preferably, an efficient path for combining a plurality of subcomponents to form the library of a plurality of final objects, more preferably according to one or more properties of the shared and/or variable aspects and/or regions of the final objects.

According to preferred embodiments thereof, the divide and conquer approach is used to determine the efficient path for combinatorial construction of the library. Using the divide and conquer approach, the algorithm finds the optimal library protocol to construct the library from its shared and variable regions with minimal number of reactions or subprocesses. The algorithm then finds a specific valid overlap within the shared regions that is suitable for synthesizing the two adjacent regions with all their variants. The overlap defines the building blocks (subcomponents) of the library, preferably for both the shared and variant regions and/or aspects of the final objects. More generally, the combinatorial optimization is preferably performed in order to minimize the overall number of required reactions from the subcomponents. Each final object is than planned using a divide and conquer algorithm for a final object (described above). The protocols for preparing final objects are preferably merged and additional reactions are added according to the optimal construction protocol as previously calculated.

According to preferred embodiments of the present invention, at least one subcomponent may optionally be erroneous or at least potentially erroneous, such that at least one erroneous or potentially erroneous subcomponent is used in the construction process which is then preferably adjusted to overcome such an error or potential error. In general, a composite object constructed from error-prone building blocks is expected to have a higher number of errors than each of its building blocks. However, if errors are randomly distributed among the building blocks and occur randomly during construction, and if sufficiently many copies of an object are constructed, it is expected that some of the copies may contain error-free components. If such components could be identified and extracted from the faulty objects, they could be re-used as building blocks for another recursive construction of the object. Since this construction starts from typically larger building blocks that are error-free, the number of errors in the resulting object is expected to decrease, possibly down to zero. Even if the objects produced this way would have errors, they are expected to have fewer errors than their predecessors and hence to have even larger error-free components, which can be used as building blocks for a subsequent corrective recursive construction, until an error-free (or at least reduced error) object is preferably formed.

According to preferred embodiments of the present invention, maximal error-free subcomponents are used as building blocks for another construction attempt. Specifically, the subcomponents are preferably analyzed to find a minimal cut in the recursive construction tree (described in greater detail below). The minimal cut is preferably used to determine which parts of which output objects (output subcomponents) are error free and to use these error free parts in order to build an object which has reduced errors (if not error free). More preferably a structure tree is used for this method. A node in the tree is covered by a set of output subcomponents if the part of the final object represented by the node is error-free in at least one output subcomponent. The minimal cut preferably defines all parts of the final object according to the most shallow nodes (those closest to the root). The minimal cut exists and is unique if all leaves of the tree are covered by the parts of the subcomponents.

If some leaf is not covered it means that its related part is erroneous in all output subcomponents, in which case either additional subcomponents must be analyzed and the minimal cut re-computed, or the subcomponent can be reconstructed and the process performed again if the subcomponent is erroneous. The correct (error free) parts of the subcomponents may optionally be extracted and used for the recursive construction process according to the minimal cut.

According to optional embodiments of the present invention, a library of a plurality of final objects may optionally undergo error correction separately as described above. Alternatively and preferably, however, each subcomponent of the library, shared and/or variant, is preferably corrected for errors as described above, after which the entire library is constructed from these error free subcomponents.

Non-limiting examples of other building blocks (subcomponents) optionally include synthetic oligonucleotides, preferably constructed in a highly parallel manner on a DNA chip in which each DNA building block on the DNA chip is more preferably individually accessible for use in construction using this method; solid state synthesis; natural DNA fragments or DNA fragments produced according to any other synthetic method (it should be noted that where reference is made herein to DNA that RNA and/or any type of non-natural polynucleotide or oligonucleotide is included). Other non-limiting examples optionally include peptides synthesized according to any synthetic method; naturally produced peptides or proteins; or any type of functional group and/or molecule, preferably including polymeric units for constructing a polymer.

According to preferred embodiments of the present invention, the divide and conquer method determines a "minimal cut" according to which a plurality of potentially or possibly erroneous subcomponents are used to construct at least one error-free final object according to an efficient path. A proof and description of the minimal cut is provided below:

A cut in a tree is a set of nodes that includes a single node on any path from the root to a leaf.

Let T be a recursive construction protocol tree and S a set of subcomponent. It is stated that S covers T if there is a set of subcomponents C such that every subcomponent in C is a sub-subcomponent of some subcomponent in S and C is a cut C of T. In such a case it may be stated that S covers T with C.

Claim: If S covers T, then there is a unique minimal set C such that S covers T with C.

Proof of Error-free reconstruction algorithm: Given an RC protocol T and a set of subcomponents S, find a minimal C such that S covers T with C.

Then C is created and the recursive construction is performed starting with C. Various specific examples are provided below for computing the minimal cut.

Section 1—Polynucleotides and Other Biopolymers

Without wishing to be limited in any way, this Section relates to exemplary, illustrative embodiments of the present invention (method and system) with regard to polynucleotide construction (and also construction of other biopolymers, as the below methods may optionally be used for construction of polypeptides). It should be noted that such polynucleotides may optionally comprise DNA and/or RNA and/or any non-natural and/or modified nucleic acids, and may optionally be double-stranded and/or single-stranded (including within the same molecule). Also wherever reference is made to "DNA" herein, this is for the purpose of explanation only as the polynucleotide may optionally comprise any of the types described above or a combination thereof.

The embodiments described above for general construction of final objects are preferably used for construction of polynucleotide sequences. A more detailed description of exemplary embodiments for methods and systems for use with polynucleotide sequences is provided below.

According to preferred embodiments of the present invention, there is provided a hierarchical, recursive construction process, preferably a modified recursive construction process, for constructing a polynucleotide sequence from a plurality of shorter nucleotide sequences. These shorter nucleotide sequences may optionally be, but are not limited to, oligonucleotides, fragments of natural DNA or RNA, or may optionally be derived by using various techniques, including but not limited to, PCR, cloning and so forth.

According to other preferred embodiments of the present invention, the method of the present invention uses the D&C method to divide the target DNA sequence in silico into fragments short enough to be synthesized by conventional oligonucleotide synthesis, albeit with errors; these error-prone molecules are recursively combined in vitro, forming error-prone target DNA molecules. Error-free parts of these molecules are identified, extracted and used as new, typically longer and more accurate, inputs to another iteration of the recursive construction procedure and the entire process is repeated until an error-free target molecule is formed.

In recursive construction, pairs of smaller elements are composed systematically into ever larger elements until the target element is constructed. According to some embodiments of the present invention, the output of the composition operation is of the same type as its two inputs; however it should be noted that other types of recursion or recursion-like processes may optionally be implemented for the present invention. For these embodiments, there is provided a novel composition reaction that takes two overlapping ssDNA fragments as input and produces an elongated ssDNA molecule as output.

In general, a composite object constructed from error-prone building blocks is expected to have a higher number of errors than each of its building blocks. However, if errors are randomly distributed among the building blocks and occur randomly during construction, and if sufficiently many copies of an object are constructed, it is expected that some of the copies may contain error-free components. If such components could be identified and extracted from the faulty objects, they could be re-used as building blocks for another recursive construction of the object. Since this construction starts from typically larger building blocks that are error-free, the number of errors in the resulting object is expected to decrease, possibly down to zero. Even if the objects produced this way would have errors, they are expected to have fewer errors than their predecessors and hence to have even larger error-free components, which can be used as building blocks for a subsequent corrective recursive construction, until an error-free object is formed. Thus, although the method uses building blocks which are oligonucleotides that may feature errors, the final product is a polynucleotide that is error free. According to preferred embodiments of the present invention, maximal error-free DNA sequences are used as building blocks for another construction attempt. Specifically, the DNA sequences are preferably analyzed to find a minimal cut in the recursive construction tree, defined as follows. A node in the tree is said to be covered by a set of DNA sequences if its sequence occurs error-free in at least one of the DNA sequences. A set of DNA sequences of molecules constructed according to a recursive construction tree induces a minimal cut on the tree, defined to be the set of the most shallow (closest to the root) nodes in the tree that are covered by the DNA sequences. The minimal cut exists and is unique if all leaves of the tree are covered by the DNA sequences. If some leaf is not covered it means that its sequence is erroneous in all DNA sequences, in which case either additional DNA sequences must be analyzed and the minimal cut re-computed, or the oligo can be re-synthesized and the process performed again if the synthetic oligo is erroneous. Since the DNA fragments that constitute the minimal cut occur in the recursive construction tree, their boundaries coincide with boundaries of fragments of the initial recursive construction tree. Therefore, they can be extracted from their respective DNA sequences and be used as building blocks for corrective recursive construction. This is executed by using their respective DNA sequences as input to the composition step in the recursive construction tree that corresponds to that specific fragment, as described in greater detail below.

A node in the tree is said to be covered by a set of DNA sequences if the sequence of the node occurs error-free in at least one of the DNA sequences. A set of DNA sequences of molecules constructed according to a recursive construction tree induces a minimal cut on the tree, defined to be the set of the most shallow (closest to the root) nodes in the tree that are covered by the DNA sequences. The minimal cut exists and is unique if all leaves of the tree are covered by the DNA sequences. If some leaf is not covered it means that its sequence is erroneous in all DNA sequences, in which case either additional DNA sequences must be analyzed and the minimal cut re-computed, or the oligo can be re-synthesized and the process performed again if the synthetic oligo is erroneous. Since the DNA fragments that constitute the minimal cut occur in the recursive construction tree, their boundaries coincide with boundaries of fragments of the initial recursive construction tree. Therefore, they can be extracted from their respective DNA sequences and be used as building blocks for corrective recursive construction. This is executed by using their respective DNA sequences as input to the composition step in the recursive construction tree that corresponds to that specific fragment, as described in greater detail below.

Computing the Minimal Cut:

A recursive approach is used for computing the minimal cut of a protocol tree. Each node in the tree represents a biochemical process with a product and two precursors. The algorithm starts with the root of the tree (target molecule) and for each node checks whether its product sequence exists with no errors in one of the DNA sequences or other sequences being used. It should be noted that for the purposes of explanation only and without wishing to be limiting in any way, this description centers around the use of DNA sequences as building blocks; however, optionally and alternatively, single molecule PCR or any other molecular amplification method (particularly any other single molecule amplification method) could be used for amplifying single DNA molecules. Also, any type of suitable building block could optionally be used. If such a DNA sequence exists this product is marked as a new basic building block for reconstruction of the target molecule and its primer pair and relevant DNA sequence (as template) are registered as its generating PCR reaction. If there is no DNA sequence which contains an error free sequence of the node product the reaction is registered as existing reaction in the new protocol and the algorithm is recursively executed on the two precursors of the product. The output of such a protocol is a tree of reactions which comprises a minimal cut of the original tree. It contains leaves for which error free products exist and that all its internal nodes are have no error free DNA sequence that contain them. An automated program that utilizes these new error free building blocks for recursive construction of the target molecule is generated for the robot.

Computing the required number of DNA sequences (building blocks)

For a fragment of size L under mutation rate R the probability of having an error free fragment in a single DNA sequence is taken from a Poisson distribution with LAMBDA=L*R (The probability to have 0 errors when the expected errors are L*R). To find the smallest number of DNA sequences required to get an error free fragment with probability larger than 95% a binomial distribution is used and the probability of having at least one error free fragment out of N DNA sequences is computed.

In the divide and conquer approach the length of the pure fragment can be reduced to the size of an oligo (~80 bp) at the expense of having to perform more steps during reconstruction. Thus in order to guarantee that there is full error free coverage of the target sequence molecule, the probability of having a pure fragment of size L in N DNA sequences—P Success (L,N) is multiplied by itself, the number of fragment of size L that are required to construct the target molecule (the first part is error free and the second part is error free etc. . . . ). This number is calculated after considering the overlap which reduces the contribution of each oligo to be smaller than its actual size (~55 bp). Then, the smallest number of DNA sequences (building blocks) which satisfies the requirement that the total probability of having a minimal cut will exceed 95% is found.

A brief description of a particular embodiment of an exemplary method according to the present invention is discussed below:

Algorithm
INPUT:
TARGET_SEQUENCE and CONFIGURATION with parameter values.
OUTPUT:
A protocol to construct the target molecule including:
SEQUENCE LIST: a list of all oligos and intermediate target products.
REACTION LIST: a list of reactions each reaction has two sequences from the sequence list as its input and one sequence as its product thus describing the protocol tree.
OLIGOS and PRIMERS list: a list of oligos that are needed to be synthesized as building blocks for the protocols.
1. Pre-processing
1.1. Find best overlap for each point and compute its range of specificity
1.2. Find best primer for each point and compute its range of specificity
2. Dvide&Conquer(TRAGET_SEQUENCE)
2.1. IF TRAGET_SEQUENCE is in Cache THEN return the protocol from cache
2.2. IF TRAGET_SEQUENCE is shorter than MAX_OLIGO_SIZE THEN return the OLIGO as the current protocol
2.3. Set CURRENT_PROTOCOL to NO_PROTOCOL and CURRENT_BEST_COST to Inf
2.4. For each Division Point check the following:
i. Valid overlap exist and comply with overlap constrains
ii. Primers for division exist and comply with Primers constrains
iii. Check Primers dimmers for each sub-target
iv. IF any of the checks 2.3.1-2.3.3 failed THEN continue to next point
v. Compute lower bound on the cost of the protocol IF LOWER_BOUND_COST>CURRENT_BEST_COST continue to next point
vi. Divide&Conquer(LEFT_SUBTRAGET)
vii. Divide&Conquer(RIGHT_SUBTRAGET)
viii. Merge protocols and compute the CURRENT_COST
ix. IF CURRENT_COST<BEST_CURRENT_COST set CURRENT_BEST_PROTOCOL=CURRENT_PROTOCOL (update cache.
2.5. Return CURRENT_BEST_PROTOCOL
Parameters
max_oligo_len: 80 maximal oligo length
min_oligo_len: 30 minimal oligo length
max_primer_Tm: 70 maximal primer melting temperature
min_primer_Tm: 60 minimal overlap melting temperature
min_primer_len: 14 minimal primer length
max_primer_len: 30 maximal primer length
min_overlap_Tm: 60 minimal overlap melting temperature
min_overlap: 15 minimal overlap length
max_overlap: 70 maximal overlap length
levelcost: 50 Cost of additional level in the protocol
reactioncost: 10 Cost of additional reaction in the protocol
oligo_constant_cost: 2 Constant cost for a single Oligo
oligo_nuc_cost: 0.2500 length dependent cost for an Oligo.
primer_ident_nucs_allowed: 15
primer_sequential_ident_nucs_allowed: 8
primer_3p_match_allowed: 5
prim3_len: 6
overlap_ident_nucs_allowed: 10
overlap_sequential_ident_nucs_allowed: 7
overlap_3p_match_allowed: 6
overlap_prim3_len: 7
min_external_fragment: 200
primer_dimer_any: 8
primer_hetrodimer_any: 8
skip_oligo_oligo_primers: 1

Divide & Conquer algorithm for DNA combinatorial library synthesis

The algorithm searches using the divide and conquer approach for a protocol to construct a combinatorial library described by the user with an efficient utilization of the library shared sequences.

General Description:

The algorithm receives a library description with variable regions separated by shared regions. Each variable region may have 2 or more variants of different sequence and size. Using the divide and conquer approach, the algorithm finds the optimal library protocol to construct the library from its shared and variable regions with minimal number of reactions considering that intermediate product may be a multiplication of the sizes of two variable regions. The algorithm then finds a specific valid overlap within the shared regions that is suitable for synthesizing the two adjacent regions with all their variants. The overlap defines the building blocks of the library, both the shared and variant fragments. Each building block is than planned using a Divide & Conquer algorithm for a single sequence (described above). The protocols of the building blocks are merged and additional reactions are added according to the libraries' optimal construction protocol previously calculated.

Non-limiting examples of other building blocks include synthetic oligonucleotides, preferably constructed in a highly parallel manner on a DNA chip in which each DNA building block on the DNA chip is more preferably individually accessible for use in construction using this method; solid state synthesis; natural DNA fragments or any other synthetic method.

The present invention may also optionally be used to build long genes and DNA libraries. Optional embodiments of the present invention with regard to applications in molecular biology and engineering include but are not limited to, discovering new aspects in protein-protein interactions, creation of proteins with new catalytic function; creation of new proteins from folds of known proteins; investigation of transcription modules and many more.

The present invention may optionally be used for a number of different applications, non-limiting examples of which include building DNA libraries that consist of all specific sequences as long as the length of full genes, and the creation of dependencies inside one sequence and between sequences in the library (conditional mutagenesis). Further non-limiting examples include new research possibilities in molecular biology and engineering, including:

1. Discovering new aspects in protein-protein interactions. Point mutation on the surface that is in charge of protein-protein interactions disturbs its protein structure. However conditional mutagenesis can create a few related mutations on both interacting proteins surfaces, allowing preservation of the protein structure.
2. Creation of proteins with new catalytic function: Creating protein libraries consisting of conditional mutations in active sides of known proteins allows creation of new proteins with a high probability that have new catalytic functions. It also helps in finding connections between sequence patterns and three dimensional structures created by those patterns.
3. Creation of new proteins from folds of known proteins: PIE supports the creation new proteins constructing them from folds of known proteins, and predicting their functions and structures with high probability.
4. Investigating transcription modules: Using conditional mutagenesis, new transcription modules can be created, allowing the investigation of interactions between different transcription factors.
5. Exploring RNA evolution: Creating RNA libraries consisting of sequences with conditional dependencies allows exploring molecule evolution and mutual interactions in the RNA soup.
6. Exploring codon usage in different expression systems: PIE allows building of systems that test influence of codon usage on translation and folding of proteins in different expression systems.
7. Parallel gene evolution: Performing evolution of several genes in parallel and assembling them into long operons or viruses.
8. Creation of proteins with new and/or modified binding and/or function(s)
9. creation of antibodies
10. generating modified\new\artificial genomes Non-Natural Nucleic Acids The present invention may optionally be implemented with one or more non-natural nucleic acids. Non-limiting examples of such non-natural nucleic acids include 5-substituted indoles (including but not limited to 5-trifluoromethyl derivatives, 5-trifluoromethoxy derivatives and 5-nitroindole derivatives), 3-nitropyrroles, carbazole bases (including but not limited to 3-nitrocarbazole and 3,6-dinitrocarbazole) and 4-substituted phenyl bases, as well as peptide nucleic acids (PNA), DNA analogs with a neutral, pseudopeptide backbone able to hybridize with a complementary DNA strand, and/or hypoxanthine.

Non-Natural Amino Acids

The below table relates to non-conventional or modified amino acids which can be used with the present invention.

TABLE 1

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-Carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-Carboxylate | Norb | L-N-methylglutamine | Nmgln |
|  |  | L-N-methylglutamic acid | Nmglu |
| Cyclohexylalanine | Chexa | L-N-methylhistidine | Nmhis |
| Cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl)glycine | Nhtrp |
| D-N-methyllysine | Dnmlys | N-methyl-γ-aminobutyrate | Nmgabu |

TABLE 1-continued

| Non-conventional amino acid | Code | Non-conventional amino acid | Code |
|---|---|---|---|
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | Penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | Penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methylvaline | Mtrp | L-α-methyltyrosine | Mtyr |
| L-α-methylleucine | Mval | L-N-methylhomophenylalanine | Nmhpe |
|  | Nnbhm | N-(N-(3,3-diphenylpropyl) | |
| N-(N-(2,2-diphenylethyl) carbamylmethyl-glycine | Nnbhm | Carbamylmethyl(1)glycine | Nnbhe |
| 1-carboxy-1-(2,2-diphenyl ethylamino)cyclopropane | Nmbc |  |  |

It should be noted that although reference is made above to a biopolymer, in fact the present invention may also optionally be used with other types of polymers as well as described in greater detail below in Section 2.

Example 1

D&C Method

This synthetic method supports synthesis of long DNA molecules or combinatorial DNA libraries in an efficient and optionally completely automated manner.

Description of the D&C-DNA Synthesis Process

The D&C-DNA synthesis method allows in-vitro synthesis of long DNA molecules or combinatorial DNA libraries, using the Divide and Conquer (D&C) approach.

D&C is an algorithm design paradigm that works by recursively breaking down a problem into two or more sub-problems of the same type. The sub-problems are optionally and preferably independently solved and their solutions are then combined to give a solution to the original problem. This technique has been applied to many well known problems in computer science. The D&C approach provides at least two potential benefits. First, it can provide a simple approach to solving conceptually difficult problems by reducing the problem size recursively until a trivial base case is reached. Second, in some cases it can substantially reduce the computational cost.

D&C is optionally and preferably applied to long DNA synthesis (or synthesis of long sequences) in the following way. The division of long DNA sequences is done in silico. The computer program processes the sequence and designs the best synthesis protocol. The assembly of the sequence is done in vitro. Short sequences (up to 85 nt) are synthesized directly, whereas longer sequences are synthesized using two shorter sequences, called progenitors, which are produced recursively (FIG. 1). The two progenitors are complementary at the ends so that the long sequence can be synthesized from them via polymerization, optionally in an elongation reaction (although this reaction may optionally not be an elongation reaction).

Figure 2:
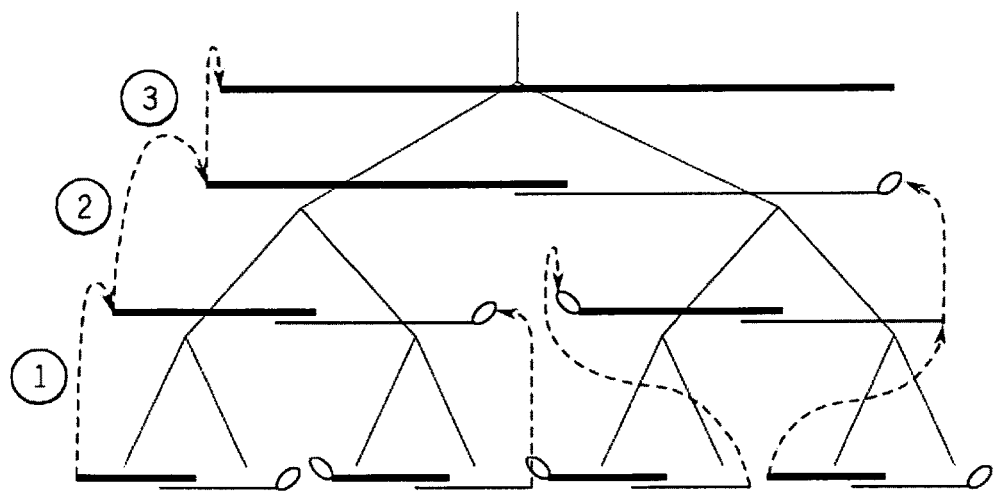
FIG. 2 shows a schematic outline of an exemplary D&C synthesis protocol according to the present invention.
Figure 3:
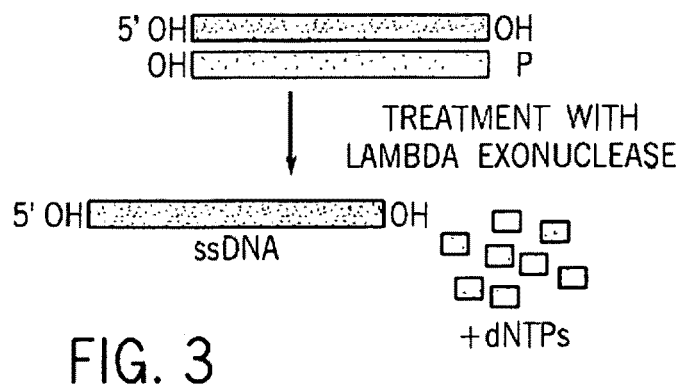
FIG. 3 shows production of ssDNA with lambda exonuclease according to the D&C method.

Design of a synthesis protocol for a long sequence consists of a binary tree, in which each node represents an $^5$intermediate sequence. The internal nodes are created in elongation reactions from their daughter nodes, and the leaves are synthesized directly. After each elongation only one DNA strand passes to the next level in the tree (FIG. 2). According to some embodiments of the present invention, strand selection is performed according to phosphorylation of one of the DNA strands, although of course other types of strand selection may optionally be performed. Preferably, before each elongation step, one of the DNA strands is phosphorylated by Polynucleotide Kinase (PNK). The elongated product is treated by Lambda Exonuclease, which digests only the phosphorylated strand and leaves intact the non-phosphorylated strand (FIG. 3).

Figures 4A, 4B:
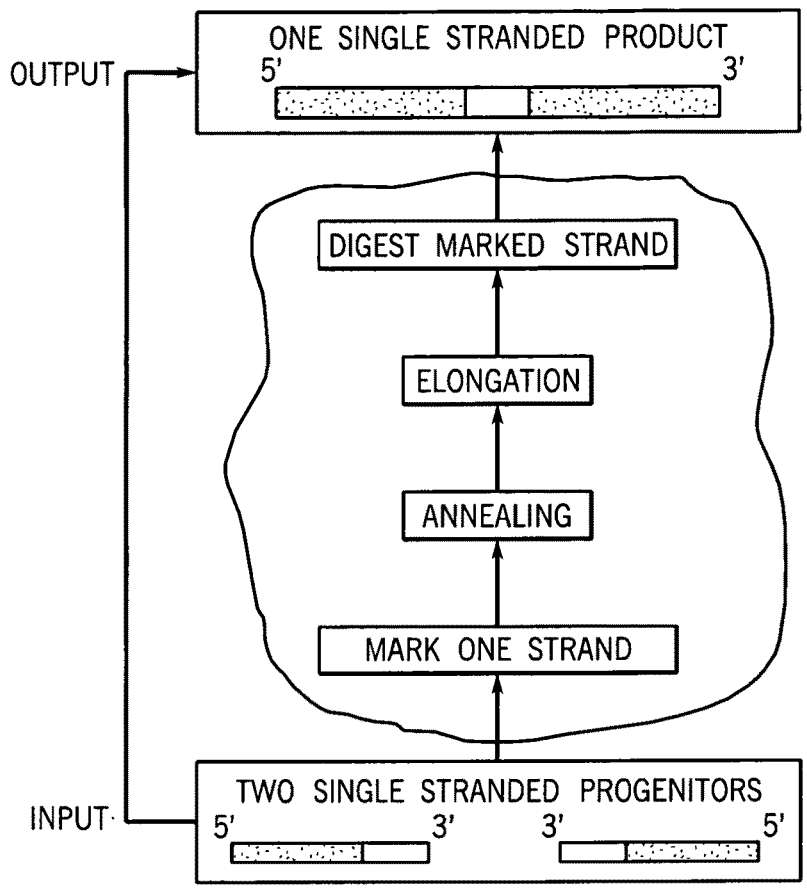

FIG. 4A shows a basic exemplary recursive process for D&C-DNA synthesis:
1. Phosphorylation one of two input strands
2. Annealing of two strands
3. Elongation
4. Production of ssDNA output The figure describes the 'heart' of the D&C-DNA synthesis process and represents the biochemical solution for the recursive procedure. The input of the procedure is composed of two short single stranded DNAs which will yield a long single stranded DNA output.

It should be noted that strand selection can be performed in numerous ways; for the purposes of discussion only and without wishing to be limited, two exemplary, illustrative methods are provided as non-limiting examples. Additionally, the recursive\hierarchal construction protocol can also potentially be realized with no strand selection.

Preferably the above calculations are performed by a computer program that determines the optimal synthesis protocol(s) according to the process outlined in FIG. 4B. The program is based on a mathematical model, in which each possible protocol receives a score corresponding to its cost of production. The program finds minimal cost protocol for generating quantity q of molecule M; in short: $\min(C(M,q))$.

Experimental Results D&C-DNA Synthesis

Some preferred embodiments of D&C-DNA synthesis were described earlier. Two options were considered for performing D&C-DNA synthesis: first, to make the elongation and strand separation on solid support, second, elongation and enzymatic strand selection in solution.

In each elongation step one of the DNA strands is biotinylated. The biotin labeling is performed during oligo synthesis. After elongation all dsDNAs are fished out by streptavidin coated magnetic beads. The strands are separated by 0.1 M NaOH and biotinylated strands heated and disconnected from the beads. One of the DNA strands passes to the next level in the tree according to the synthesis tree.

The efficiency of biotinylated DNA binding to streptavidin magnetic beads and strand separation was examined. Binding efficiency is influenced by oligonucleotide impurities. Not all biotin labeled oligos after synthesis carry biotin. Oligonucleotide (oligo) purification helps to overcome this problem.

Figure 5A:
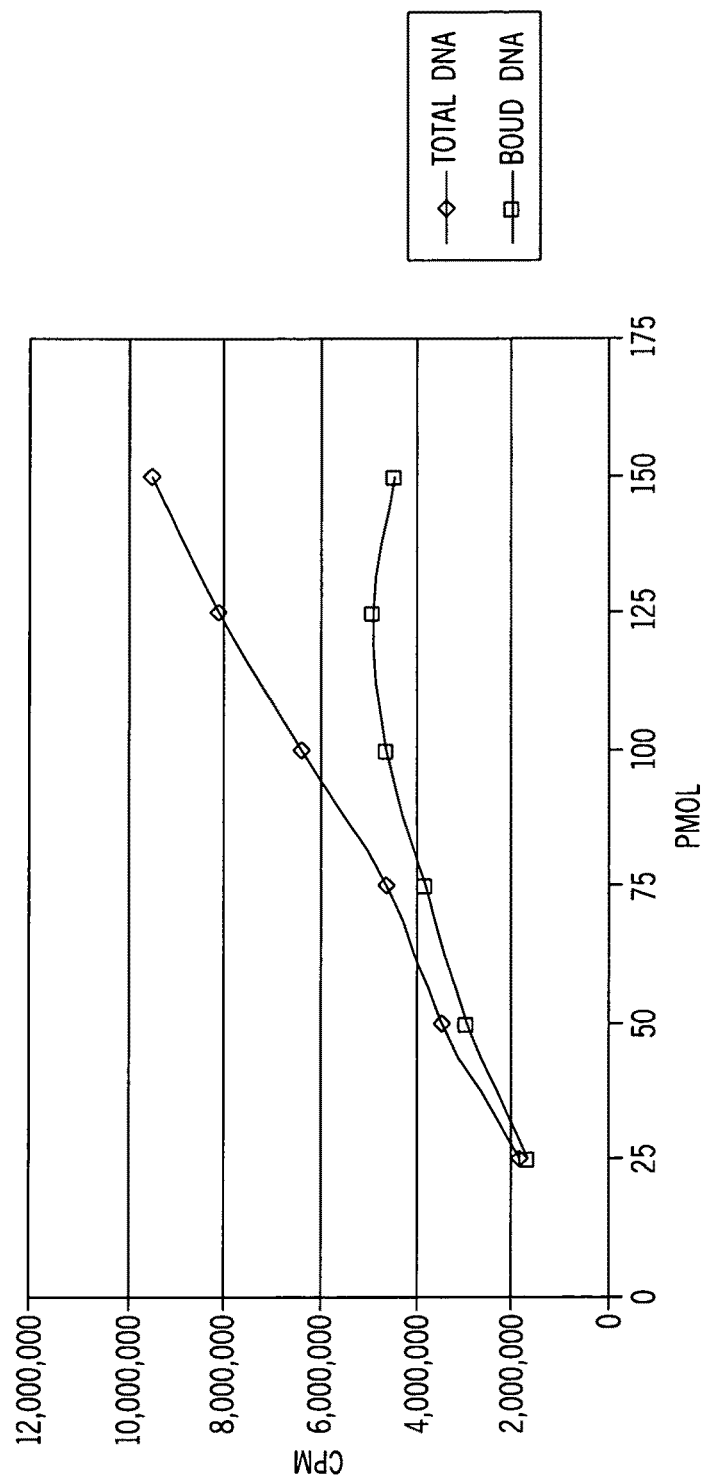
FIG. 5 shows the measurement of binding capacity of biotin labeled ssDNA ((A) Specific binding; (B) Unspecific binding)
Figure 5B:
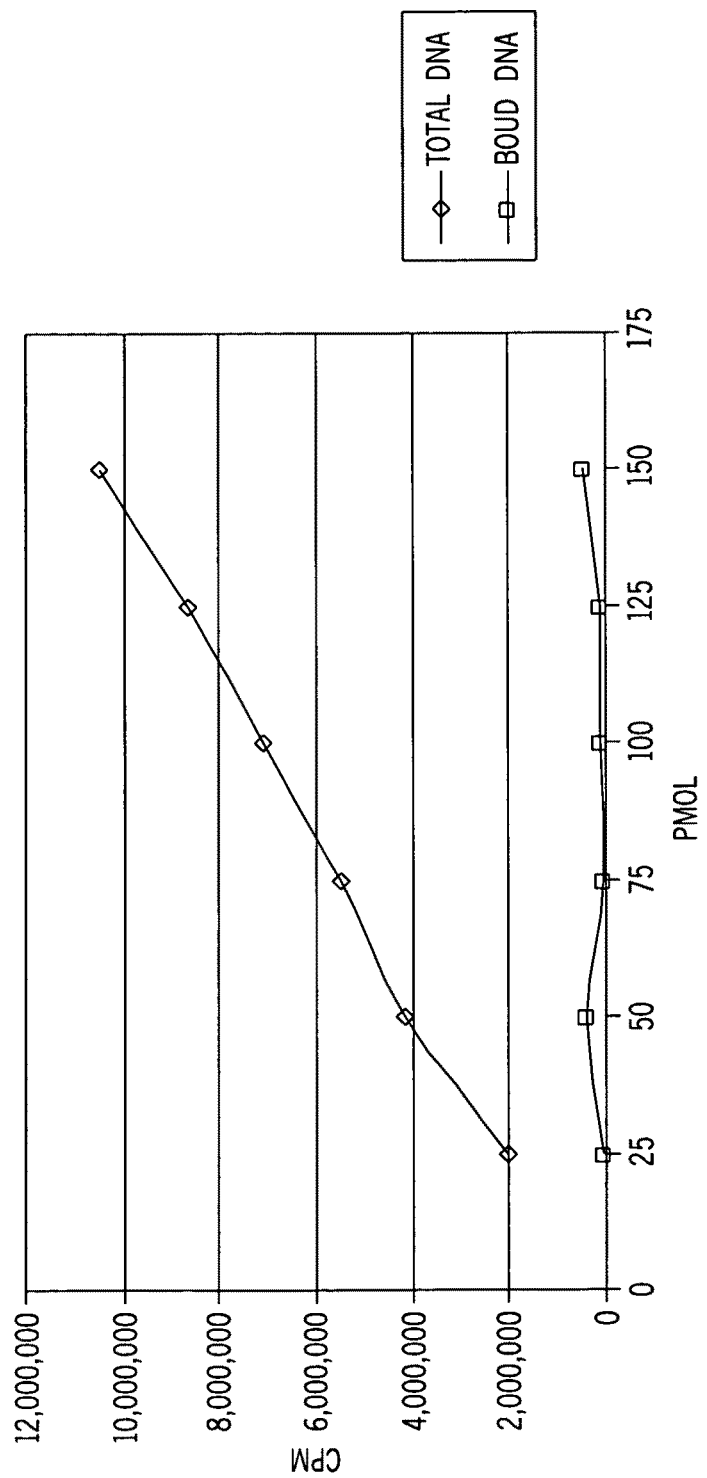

In order to test the binding efficiency of biotinylated oligos to the beads used as well nonbiotinylated oligos of the same length (25 nt), the oligos were labeled with $P^{32}$. The specific and unspecific binding was tested in two experiments. In one 25 pmol of biotinylated oligos were added at each time to a tube containing 10 µg of beads (Dynabeads MyOne Streptavidin) to check the specific binding of the beads (FIG. 5 A). The other experiment was done as above except the oligo added was unbiotinylated which tested the nonspecific binding to the beads (FIG. 5 B). The binding capacity was measured by counting radioactive radiation of oligos in solution and an-bound and coupled to beads. The 25 pmol oligos were incubated in 1×B&W Buffer (5 mM Tris-HCl (pH 7.5); 0.5 mM EDTA; 1.0 M NaCl) with Dynabeads MyOne™ Streptavidin (Dynal) 10 µg 15 min. The beads were separated by magnets, then the beads were washed in 1×B&W Buffer. The radiation level of 1 samples was measured in unbound supernatant and wash solutions. Then the beads were incubated with the next portion of the 25 pmol oligos.

From experimental work it was noted that longer biotinylated DNA had reduced binding ability.

Figure 6:
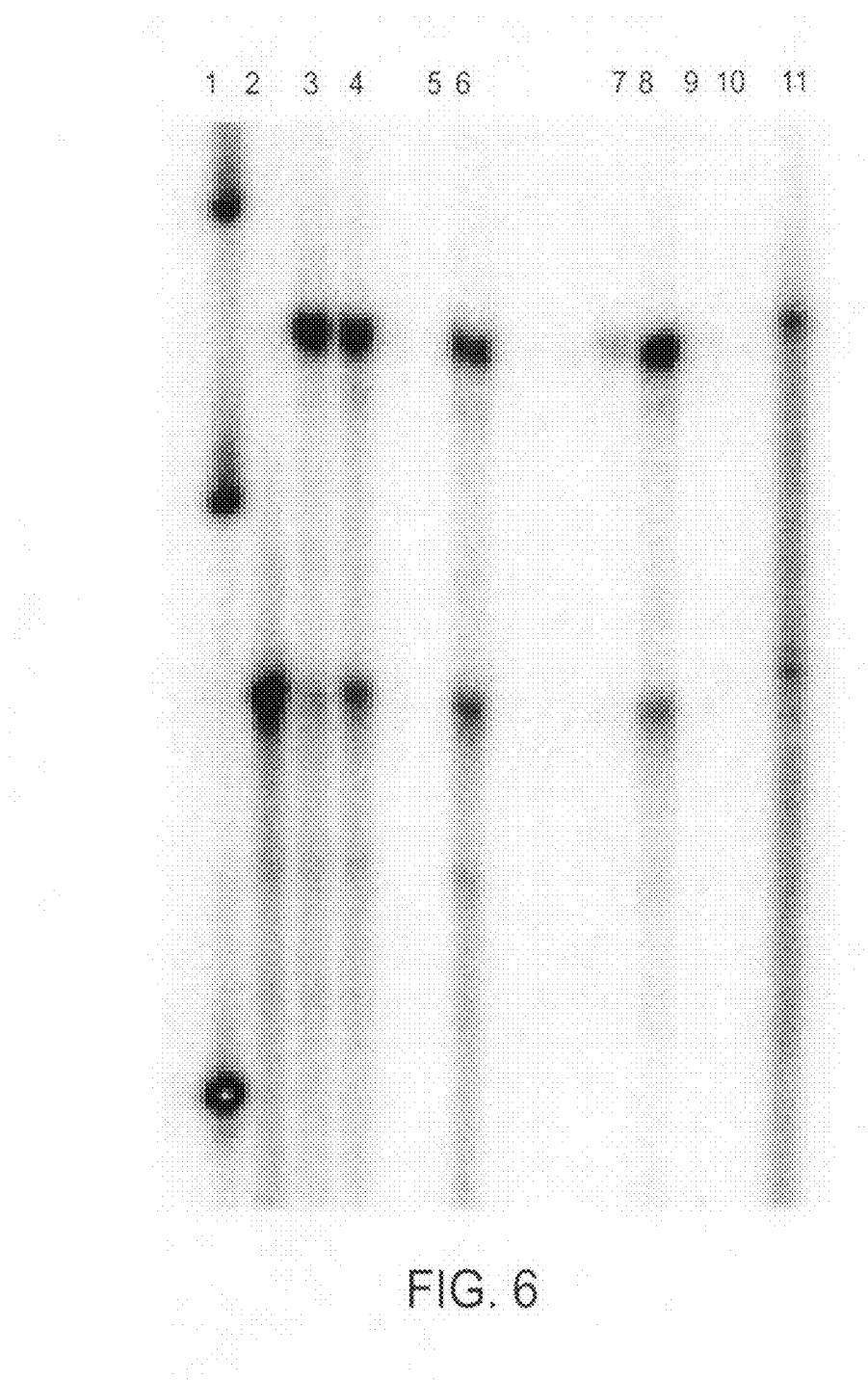
FIG. 6 shows one step elongation, transfer, separation and release, with the following lanes: (1) Marker; (2) Control (non elongated DNA); (3) elongation by T7 Pol; (4) Elongation by Klenow Fragment; (5) Supernatant of Wash 1; (6) unbound sup to beads; (7) Supernatant of Wash 2; (8) Separation by NaON; (9) Supernatant of Wash 3; (10) beads after boiling; (11) released biotinylated strand, P32 labeled.

According to the protocol the elongated dsDNA was fished out using streptavidin magnetic beads. The unbiotinylated strand was released using 0.1 M NaOH and neutralized by 0.1 M HCl. The biotinylated strand was released from beads by boiling. The biotinylated strand was radioactively labeled after releasing for visualization (FIG. 6).

Figure 7:
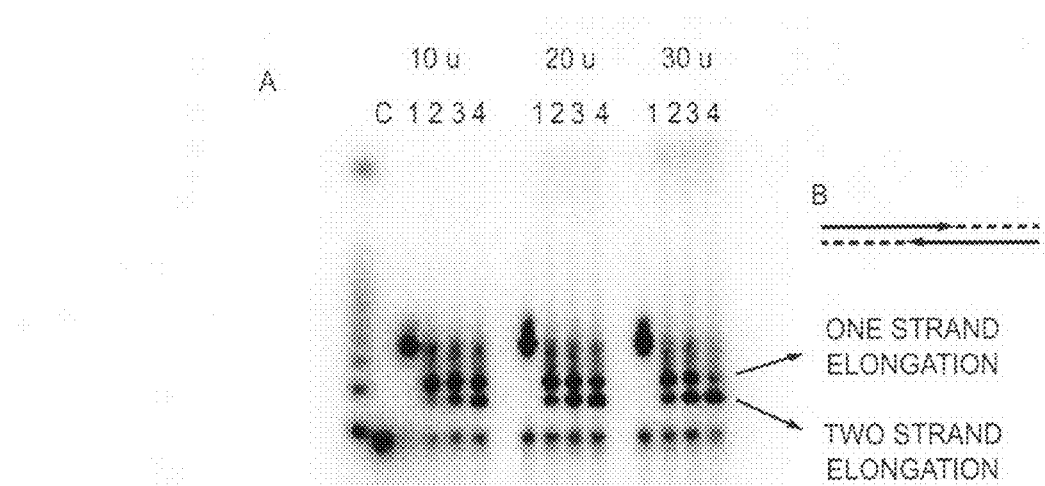
FIG. 7 shows oligo elongation with different quantities of Klenow Fragment (native gel). C, control before elongation. 10 u, 20 u, 30 u total amount of polymerase used for elongation of 50 pmol oligos. Elongations were analyzed after 0, 60, 120 and 180 min.

Elongation of oligonucleotides (50 pmol each) by 10, 20 and 30 units Klenow Fragment was done in 30 µl of 1× buffer (10 mM Tris-HCl, pH 7.5, 5 mM $MgCl_2$, 7.5 mM dithiothreitol; 200 mM dNTPs) for 0, 60, 120 and 180 min at 37° C. FIG. 7 shows that elongation occurs in two phases; as each strand is elongated separately and the elongation is time consuming, each annealed duplex is elongated in two directions. However, this did not occur simultaneously and the speed of elongation is dependent on DNA Polymerase elongation efficiency. It was observed that Klenow Fragment is not the best candidate for elongation because it has low elongation efficiency.

Figure 8:
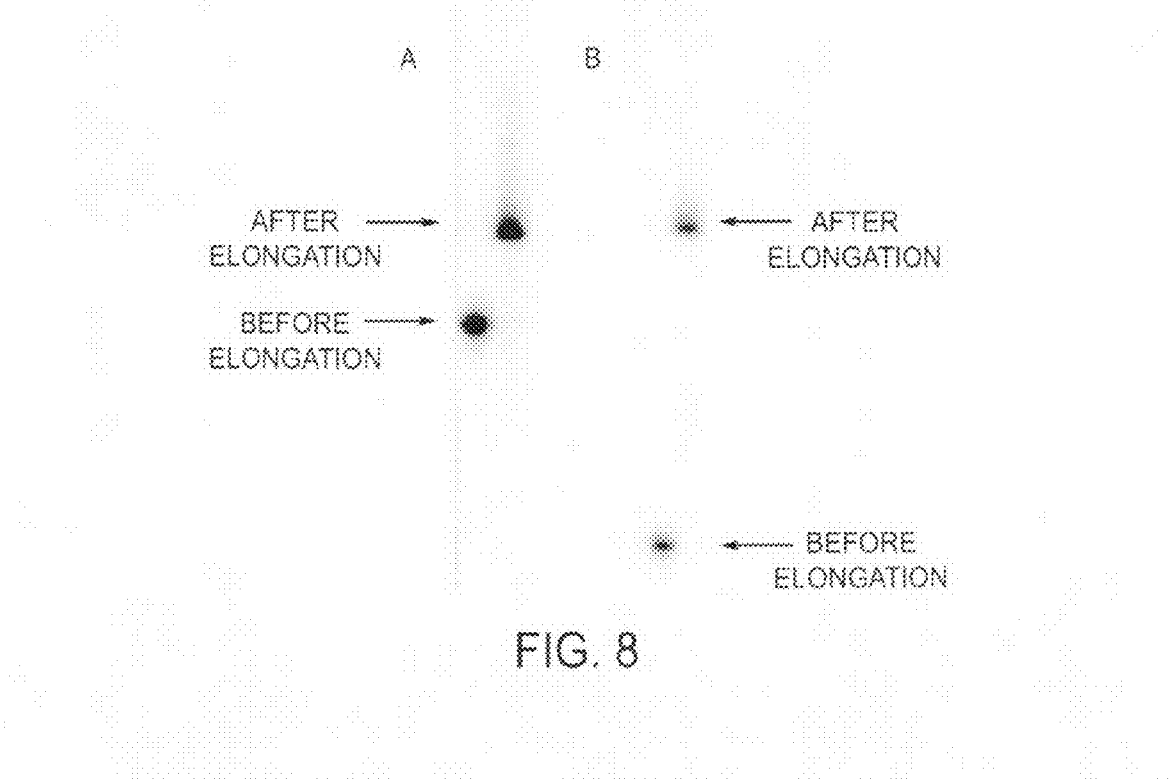
FIG. 8 shows the elongation of two pairs of oligos by Sequenase Version 2.0.
Figures 9, 10:
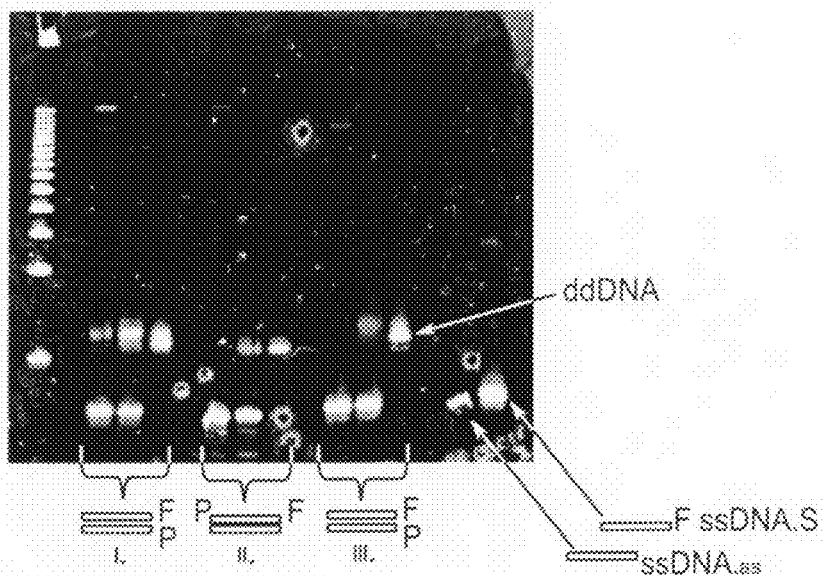
FIG. 9 shows (A) Elongation of 30 pmol DNA by 1.65 u of Sequenase Version 2.0 at different time points. (a) ssDNA before elongation (b) Heterodimer after annealing (c) time points. (B) Elongation of 30 pmol DNA by 1, 4, 8, 16 u of Sequenase Version 2.0 after 30 min.
FIG. 10 shows a test of exonuclease activity of the Lambda Exonuclease. Sense DNA was labeled at 3' by Fluoroscein and antisense DNA was visualized by Ethidium Bromide staining. (I) Digestion of antisense DNA after Chemical Phosphorylation. (II) Digestion of sense DNA after phosphorylation by PNK. (III) Digestion of antisense DNA after phosphorylation by PNK.

As an alternative to Klenow Fragment, Sequenase Version 2.0 was considered. This enzyme has very high elongation efficiency and is very precise. It was developed on the basis of T7 DNA Polymerase. Elongation of oligonucleotides (50 pmol each) by 20 units of Sequenase Version 2.0 was done in 30 µl of 1× buffer (40 mM Tris-HCl, pH 7.5, 20 mM $MgCl_2$, 50 mM NaCl, 5 mM dithiothreitol; 200 mM dNTPs) for 30 mM at 37° C. FIG. 8 shows the elongation of two pairs of oligos by Sequenase Version 2.0. After fine tuning of reaction conditions it was found that for elongation of 30 pmol 1.65 units of this enzyme can be used, and the reaction occurs in 15 mM (FIG. 9).

During the work on improvement of mechanical strand separation and selection on solid support, an alternative simple method was considered, based on enzymatic selective strand labeling and efficient enzymatic selection in solution. The main idea was that before each elongation step one of the DNA strands is phosphorylated by polynucleotide kinase (PNK). The elongated product was treated by Lambda Exonuclease. This Exonuclease digests only the phosphorylated strand and leaves intact the non-phosphorylated strand.

The following figure demonstrates the exonuclease activity of Lambda Exonuclease. Lambda Exonuclease is very specific and has very high exonuclease efficiency (FIG. 10). Enzymatic DNA phosphorylation: of 2000 pmol of DNA was done in 120 µl of 1×PNK Buffer (70 mM Tris-HCl pH 7.6 in 25° C.; 10 mM $MgCl_2$ 5 mM dithiothreitol) containing 1 mM ATP and 80 u of T4 Polynucleotide Kinase (PNK) (NEB) for 60 mM at 37° C. DNA annealing was done in 20 µl of 40 mM Tris-HCl pH 7.5; 20 mM MgCl, 50 mM NaCl by slow cooling from 96° C. to 25° C. in a rate of 0.04° C./sec. Lambda Exonuclease digestion of 60 pmol of dsDNA in which one strand was phosphorylated was done in 50 µl of 67 mM Glycine-KOH (pH 9.4; 5 mM $MgCl_2$; 0.01% Triton X-100 using 10 u of Lambda Exonuclease for 45 mM at 37° C. (Epicentre).

Figure 11:
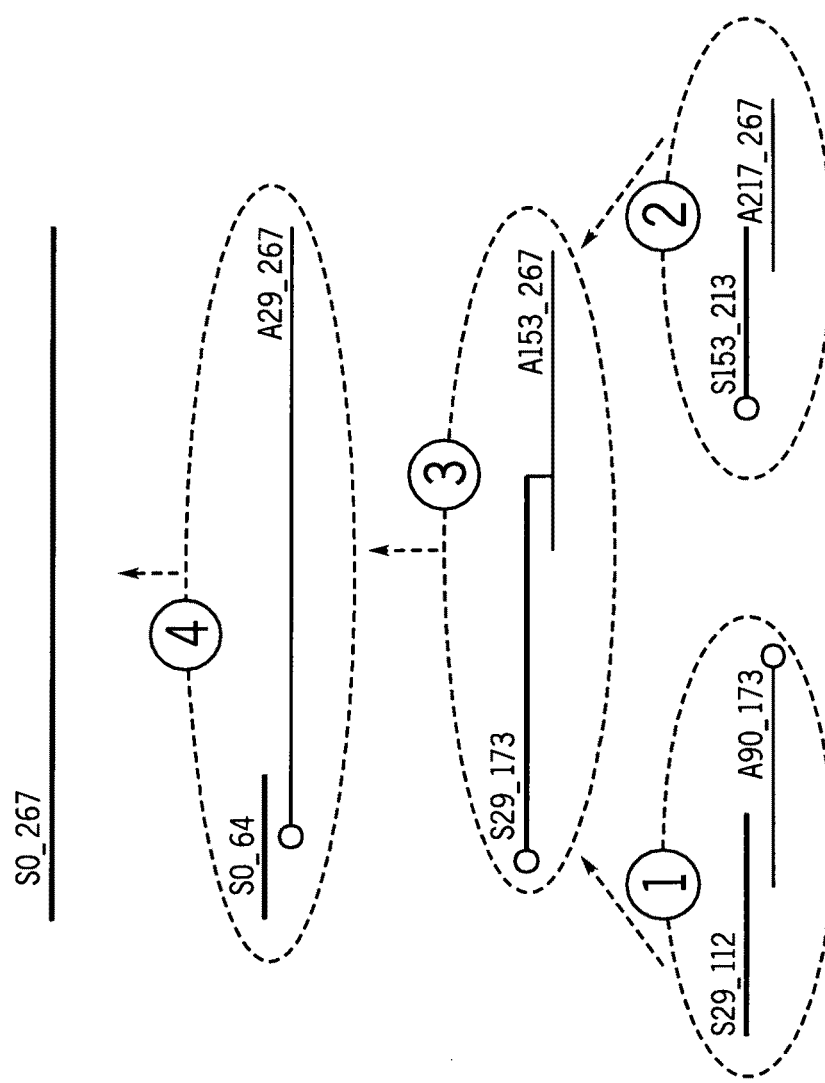
FIG. 11 shows an exemplary D&C tree showing the concept according to the design protocol. Pink circles show the DNA stands that are phosphorylated.

Suitable conditions for all the reactions for one recursion step in DC-DNA synthesis synthesis were determined. Biochemically, the recursive process may optionally be described as follows:

1. Phosphorylation of one of two ssDNA that enter the recursion.
2. Annealing of this two ssDNA.
3. Elongation
4. Stand selection The design of the protocol for the above concept was according to the software developed by the inventors. The program chose the best and cheapest protocol (FIG. 11) according to the scoring function taking into account many parameters such as amounts of oligos synthesis and their cost, amounts of intermediate products, hybridization yield of the desired heterodimer in each step in the protocol, rate of success in each step and reaction cost.

For realization of this protocol, 5 oligos were synthesized. The names of oligos and of intermediates products are: S, sense; A, antisense; numbers show the sequence location in the final product.

(SEQ ID NO: 18)
S0_64 (65 nt)
ACCGGTCATGAGATTATCAAAAAGGATCTTCACCTAGATCCTTTTAAATT
AAAAATGAAGTTTTA (SEQ ID NO: 19)
S29_112 (84 nt)
TCACCTAGATCCTTTTAAATTAAAAATGAAGTTTTAAATCAATCTAAAGT
ATATATGAGTAAACTTGGTCTGACAGTTACCAAT (SEQ ID NO: 20)
A90_173 (84 nt)
CAGGCAACTATGGATGAACGAAATAGACAGATCGCTGAGATAGGTGCCTC
ACTGATTAAGCATTGGTAACTGTCAGACCAAGTT (SEQ ID NO: 21)
S153_231 (79 nt)
TCGTTCATCCATAGTTGCCTGACTGCCCGTCGTGTAGATAACTACGATAC
GGGAGGGCTTACCATCTGGCCCCAGTGCT (SEQ ID NO: 22)
A217_267 (51 nt)
GAAACGATTCCGGTCGAGACCTTGCGGTATCATTGCAGCACTGGGCCAG
A

The following table shows the parameters of all hybridization reactions according to the nearest neighborhood algorithm[vi].

| Hetedidimer | Overlap (bp) | $T_M$(° C.) | $\Delta G°_{37.0}$ (kcal/mol) | $\Delta H°$ (kcal/mol) | $\Delta S$ (eu) |
|---|---|---|---|---|---|
| S29_112 A90_173 | 23 | 68.7 | −24.92 | −172.4 | −475.51 |
| S153_213 A217_267 | 15 | 70.0 | −19.98 | −114.8 | −305.72 |
| S29_173 A153_267 | 21 | 67.7 | −23.93 | −116.6 | −460.00 |
| S0_64 29_267 | 36 | 67.2 | −32.92 | −270.6 | −766.34 |

The below description relates to one iteration protocol.
One Step Protocol
1. Phosphorylation of ssDNA(-P) strand according to the protocol

| Phosphorylation Name | const. Reaction vol. (50 ul), Enzyme q (10 u), DNA vol(36 ul) | | | |
|---|---|---|---|---|
| | Initial Conc. | Dilution X | Volume [ul] | Final Conc.] |
| Buffer A | 10 X | 10 | 5 | 1 X |
| ATP | 100 mM | 100 | 0.5 | 1 mM |
| DTT | 100 mM | 20 | 2.5 | 5 mM |
| Enzyme A - PNK | 10 u/ul | 50 | 1 | 0.2 u/ul |
| H20 | — | — | 5 | — |
| ssDNA(-P) | 3.0 pmol/ul | 1.39 | 36 | 2 pmol/ul |
| Total Volume | | | 50 | |

2. Incubation for 30 min at 37° C.
3. Inactivation for 10 min at 75° C.
4. Purification of ssDNA by gel filtration
5. Annealing of Phosphorylated and non Phosphorylated strands

| Annealing | const. Reaction vol. (110 ul), DNA vol(36, 50 ul) | | | |
|---|---|---|---|---|
| Name | Initial Conc. | Dilution X | Volume [ul] | Final Conc. |
| Buffer B | 5 X | 5 | 22 | 1 X |
| H20 | — | — | 2 | — |
| ssDNA | 3.0 pmol/ul | 3 | 36 | 1.0 pmol/ul |
| ssDNA(+P) | 2 pmol/ul | 2.2 | 50 | 1.0 pmol/ul |
| Total Volume | | | 110 | |

6. Hybridization by slow cooling 95° C.→25° C. 0.04° C./sec
7. Elongation of hybridized strands

| Elongation Name | const. Reaction vol. (125 ul) | | | |
|---|---|---|---|---|
| | Initial Conc. | Dilution X | Volume [ul] | Final Conc. |
| Buffer B | 5 X | 5.0 | 3.8 | 1 X |
| dNTP | 25 mM each | 85.91 | 1.5 | 0.3 mM each |
| DTT | 100 mM | 20.0 | 6 | 5 mM |
| Enzyme B - Seq II | 1.63 u/ul | 76.9 | 2.52 | 0.02 u/ul |
| H20 | — | — | 4.97 | |
| Annealed DNA | 0.98 pmol/ul | 1.18 | 106 | pmol/ul |
| Total Volume | | | 125 | |

8. Incubation for 30 min at 37° C.

9. Inactivation for 10 min at 75° C. and slow cooling 80° C.→25° C. 0.1° C./sec

10. Purification of dsDNA by PCR purification kit. Elution in 30 µl

11. Degradation of the Phosphorylated strand

| Exonucleation Name | const. Enzyme q (20 u), DNA vol (30 ul) | | | |
|---|---|---|---|---|
| | Initial Conc. | Dilution X | Volume [ul] | Final Conc. |
| Buffer C | 10 X | 10 | 3.8 | 1 X |
| DTT | 100 mM | 20 | 1.9 | 5 mM |
| Enzyme C - Lam. Exo | 10 u/ul | 19.0 | 2 | 0.53 u/ul |
| H20 | — | — | 0.3 | |
| Elongated DNA | 3.4 pmol/ul | 1.3 | 30 | 2.65 pmol/ul |
| | | Total Volume | 38 | |

12. Incubation for 30 min at 37° C.

13. Inactivation for 10 min at 75° C.

14. Purification of ssDNA by gel filtration

DNA Samples are Ready for the Next Iteration Step.

Figure 12:
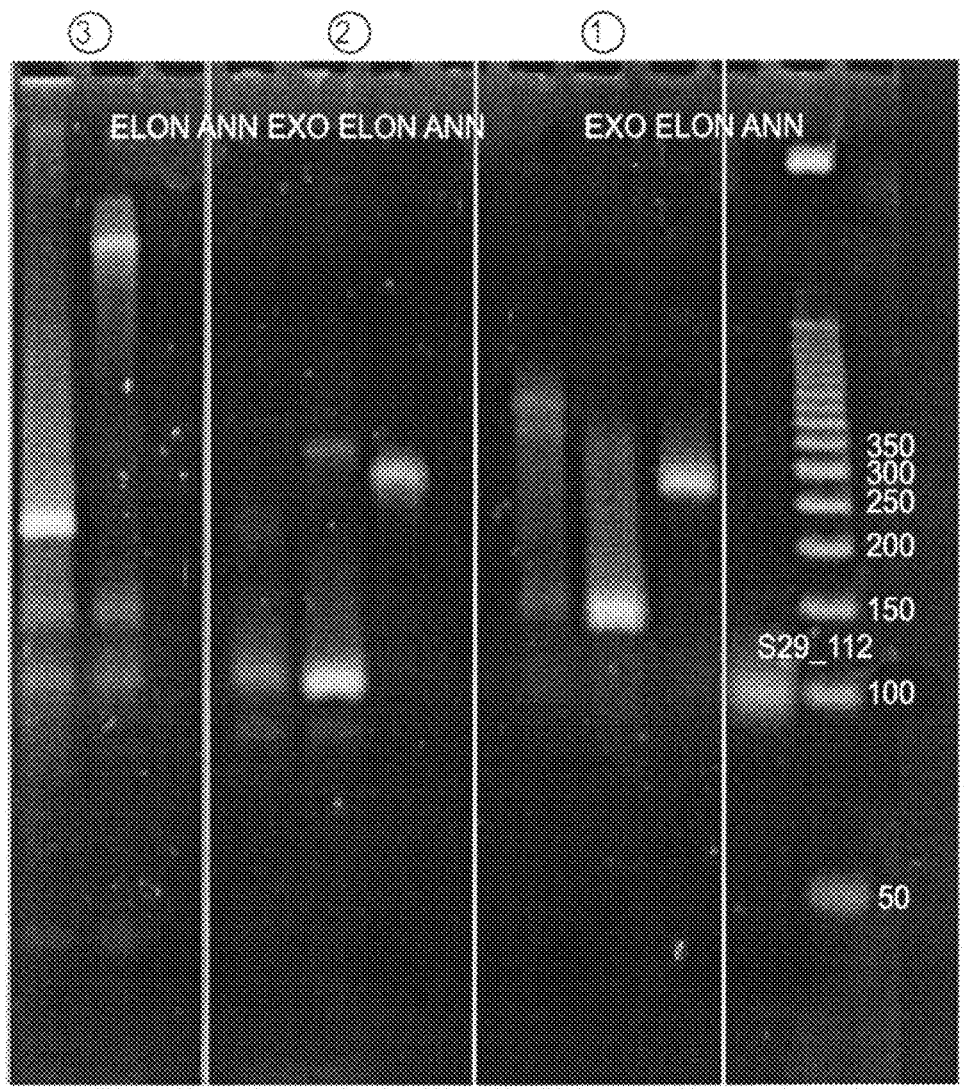
FIG. 12 shows progress of two levels of synthesis. S29_112 oligo labeled by Cy5 at 5'(red). Ethidium-Bromide staining is green. (1), (2) and (3) are reaction steps according to the protocol. In each reaction: Annealing (Ann), Elongation (Elon), strand selection (Exo).

FIG. 12 shows progress of two levels of synthesis. In this experiment S29_112 oligo was labeled by Cy5 at 5'. All of the other oligos were not labeled. It can be seen that at the end of elongation the dsDNA product has the expected length.

Figure 13:
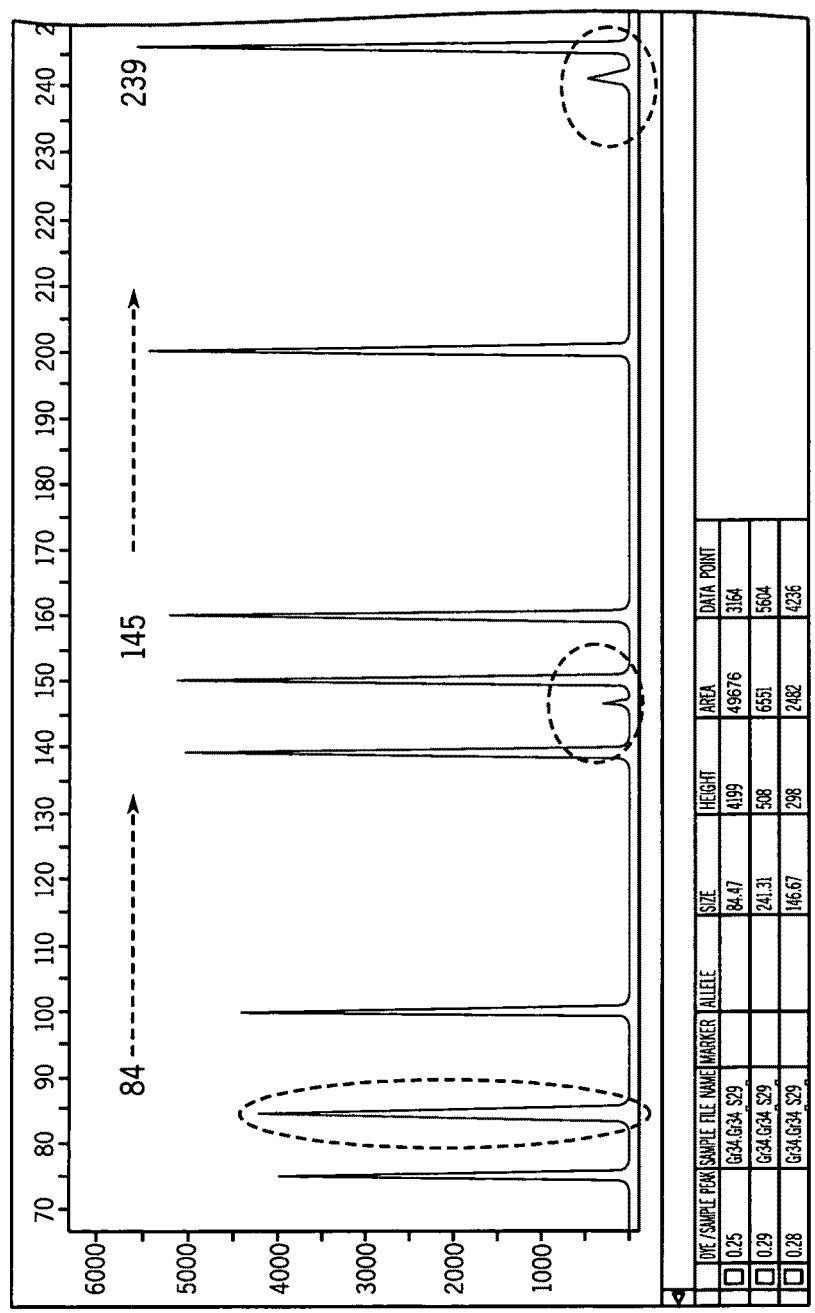
FIG. 13 shows capillary electrophoresis. Summary of two step synthesis 84 nt→145 nt and 145 nt→239 nt; Orange sample was labeled by Cy5. Marker is Orange labeled by Liz.

The products were tested after each synthesis step by Capillary electrophoresis. Two fluorescent label markers VIC and Cy5 were used. The DNA molecules are elongated from step to step. The differences in size after each step between the two dyes are result of shift that caused by the dyes (FIG. 13).

Figure 14:
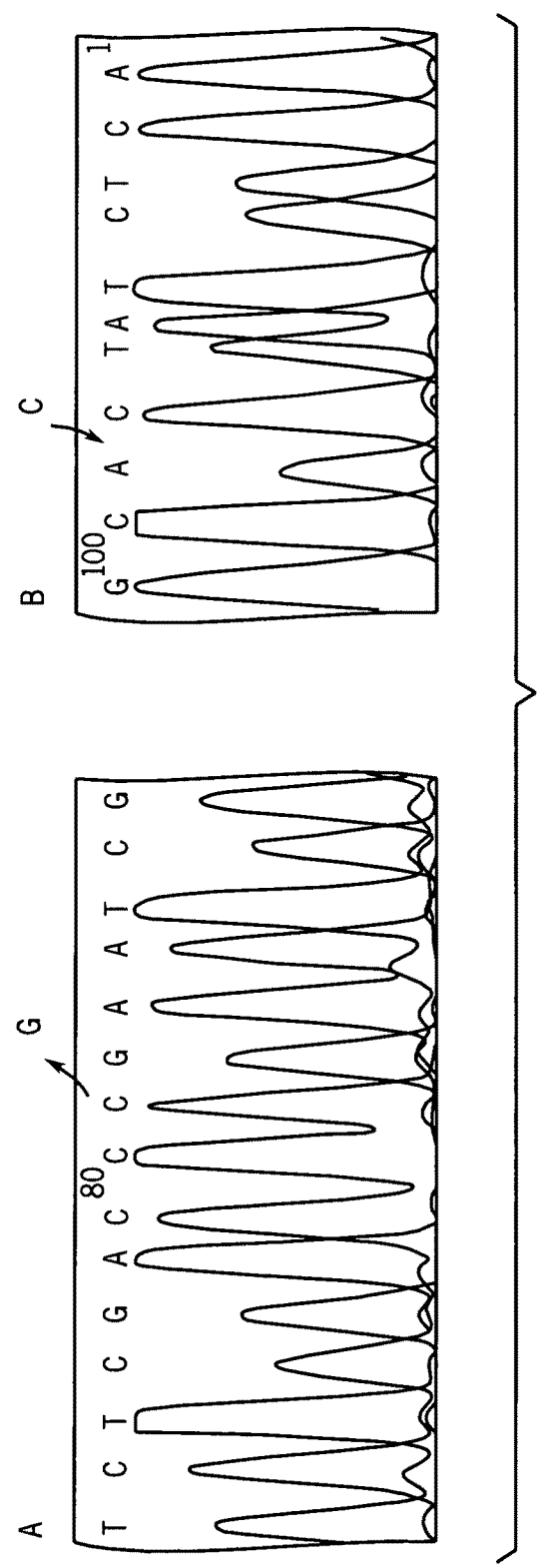
FIG. 14 shows errors in the sequence. (A) substitution of "C" instead of "G". (B) deletion of "C".

The products in both directions after each elongation step were sequenced. Some errors were found. One substitution and one deletion are shown in FIG. 14. After analysis of the possibility of sources of these errors, it was found that part of the errors resulted during the synthesis of the oligonucleotides and part resulted during the elongation. These issues are addressed below.

Figure 15:
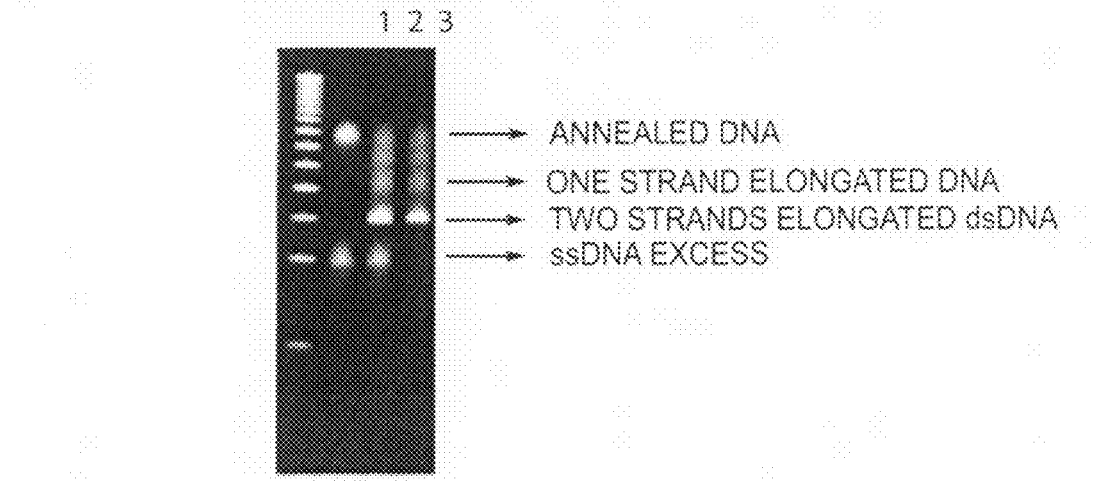
FIG. 15 shows digestion of ssDNA excess by Exonuclease I; lane 1 shows annealing of two strands; lane 2 shows elongation by DNA polymerase; line 3 digestion of ssDNA excess by Exonuclease I.
Figure 16:
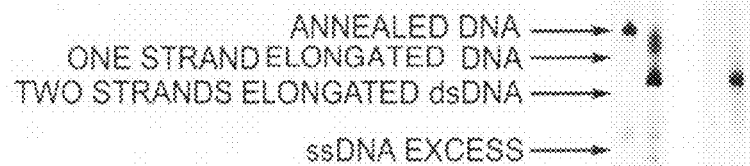
FIG. 16 shows purification by Mung Bean Nuclease at 80° C. 30 min. lane A shows annealing; lane E shows elongation; line MB shows cleaning by Mung Bean Nuclease.

In the synthesis process two points that can cause error accumulation are: strand annealing and elongation. During the annealing not all molecules find their couples because of some measurement errors of DNA concentrations and pipetting. In this case some ssDNA molecules create self loops. This secondary structure has elongation potential. Sometimes during elongation not all two hybridized strands are elongated, in some cases only one strand is elongated. To eliminate the error accumulation, methods for specific DNA selection according to its properties were considered. In FIG. 15 post elongation cleaning of dsDNA elongated product from ssDNA excess by Exonuclease I (30 mM at 37° C.) is shown. Exonuclease I has 3'→5' ssDNA specific exonuclease activity. This enzyme has very specific and high exonuclease activity and can work directly in elongation buffer. But from the experiments it was determined that the enzyme could not progress on strong secondary structures. The samples were heated to open the secondary structure, but Exonuclease I was inactivated at 65° C. The other solution for specific DNA cleaning was to use Mung Bean nuclease. It has 3'→5', 5'→3' ssDNA nuclease activity and ssDNA endonuclease activity. This enzyme has thermostable properties. FIG. 16 shows its activity after 30 mM in 80° C. Mung Bean nuclease cleaned both ssDNA excess and one strand elongated DNA. Reaction conditions are 30 mM sodium acetate (pH 4.6), 50 mM sodium chloride, 1 mM zinc acetate, and 0.01% Triton X-100, Mung Bean nuclease 10 units (Epicentre) and DNA 10-70 pmol after elongation reaction. This is a very important tool for "garbage DNA" collection, as it is able to eliminate molecules that should not be present after the end of each synthesis cycle.

Proof of Concept with Natural Sequences.

Figure 17:
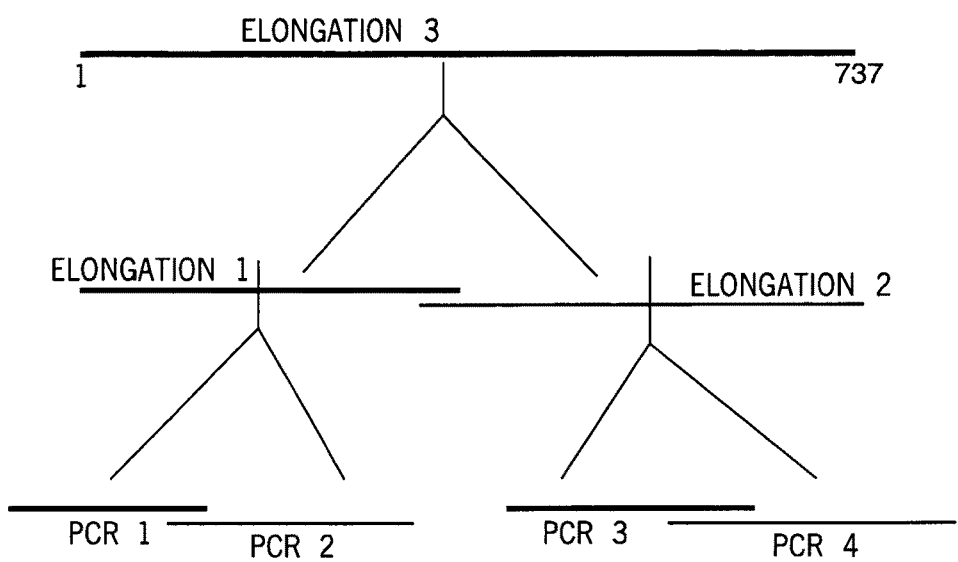
FIG. 17 shows a proof of concept with natural sequences describing the D&C synthesis protocol for a 737 bp long DNA polynucleotide.

Proof of concept was performed by using a known sequence taken from the pBK plasmid. A sequence of 737 bp was used to create a D&C-DNA synthesis protocol for it with minimal length of approximately 200 bp. The protocol is presented in FIG. 17.

The sequences of the leaves of the D&C protocol tree were obtained by four individual PCR reactions (in 50 µl of 10 mM Tris-HCl, pH 8.3, 50 mM KCl, 1.1 mM MgCl$_2$, 0.01% Gelatin, 200 mM dNTPs, 0.5 µM of each primer and 0.04 nM pGEM plasmid; 25 cycles). In each PCR reaction one of the primers was phosphorylated and before the elongation synthesis process the phosphorylated strand was digested by lambda exonuclease I. To obtain the final product (elongation 3), a two level recursive synthesis procedure was applied. In the first level of the synthesis elongation 1 and 2 were obtained. Elongation 1 was obtained from PCR 1 and 2 and elongation 2 was obtained from PCR 3 and 4. In the second level of synthesis, a product corresponding to elongation 3 was obtained from elongation 1 and 2. The sequences of the progenitors and products obtained in each step were confirmed by sequencing. Perfect matches have been seen with the expected sequences.

FIG. 18 shows the complete sequence of the 737 bp DNA structure that was produced by the present inventors, termed Amp_PCR1-PCR4; Elon3F-Prm1F represents the sequence of the final product from its beginning; E3-F represents the sequence of the final product from its middle.

Figure 19:
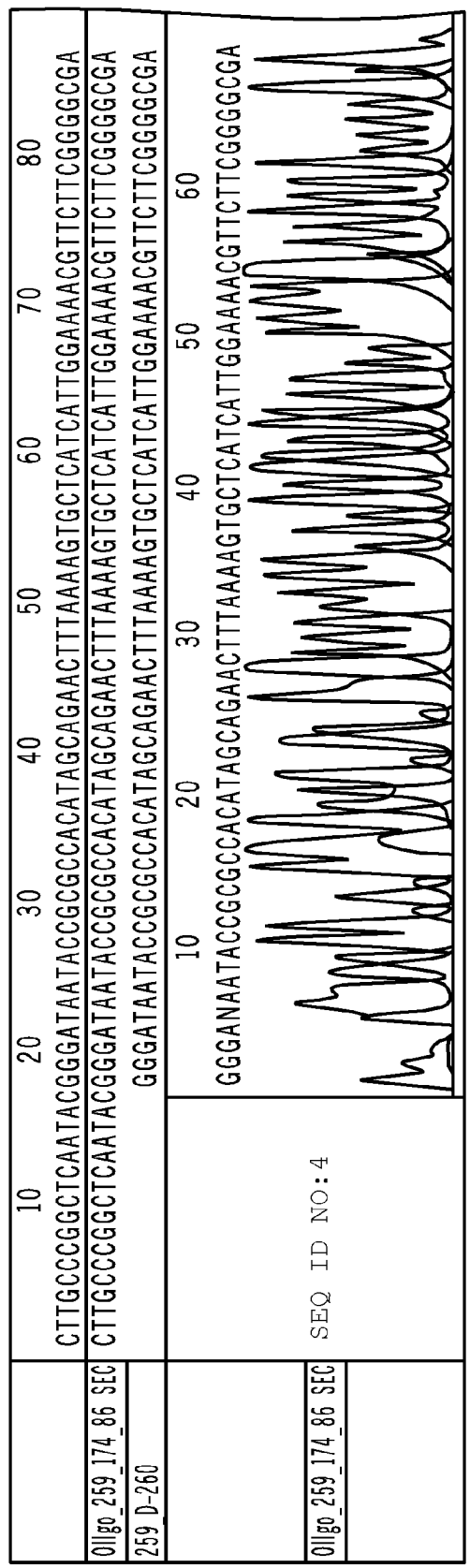
FIG. 19 shows the sequence of the PCR product of an oligonucleotide, including the following sequence: Oligo_259_174_86 (SEQ ID NO:4)
Figure 20:
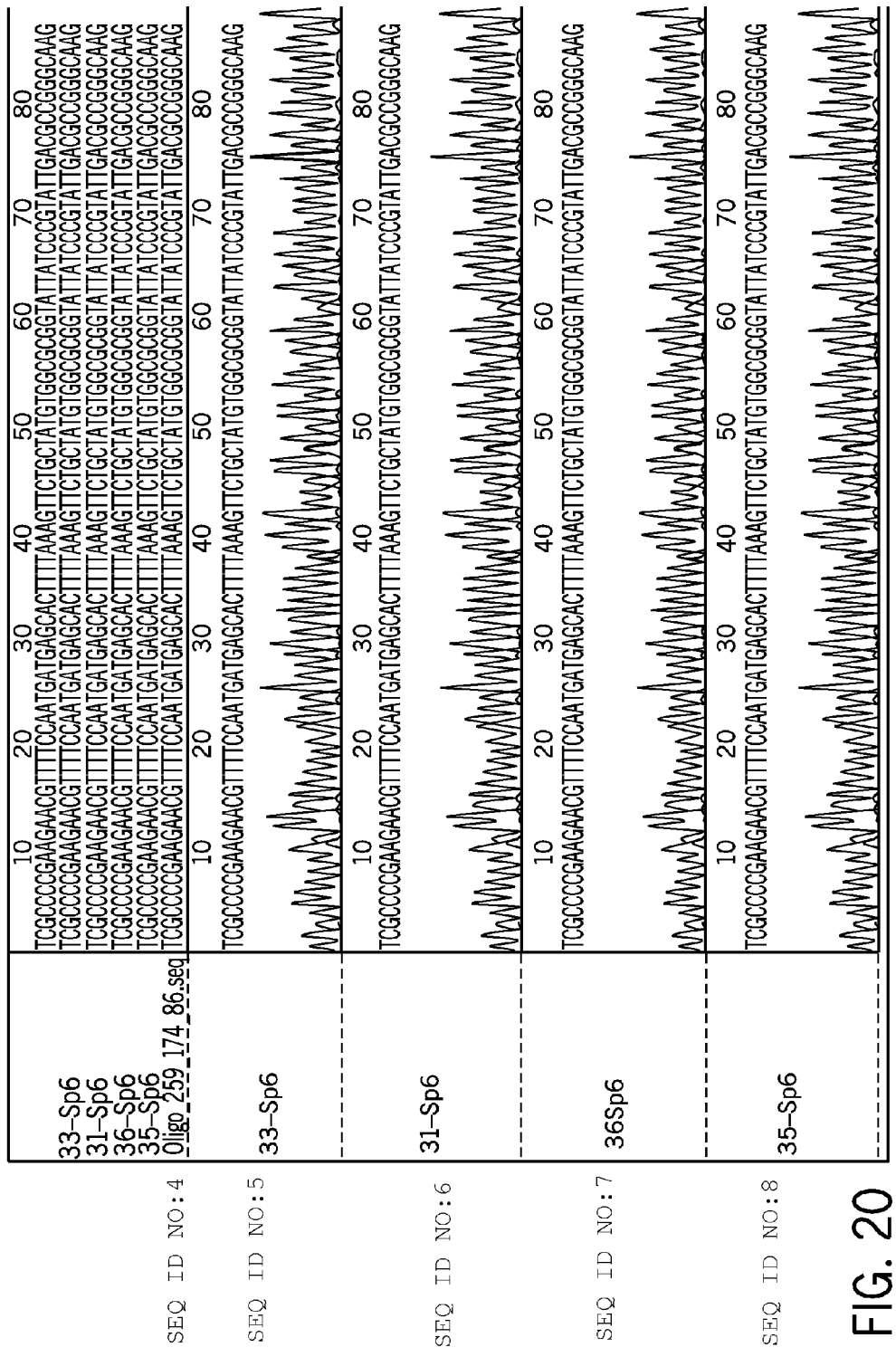
FIG. 20 shows alignment of sequences of PCR products obtained after cloning, including the following sequences: Oligo_259_174_86 (SEQ ID NO:4), 33-Sp6 (SEQ ID NO:5), 31-Sp6 (SEQ ID NO:6) and 36Sp6 (SEQ ID NO:7), 35-Sp6 (SEQ ID NO:8)

In order to resolve the problem of error rates during elongation while working with synthetic oligonucleotides, PCR was performed on these oligonucleotides using two primers for each oligonucleotide (one of them phosphorylated). The results obtained showed that it is possible to sequence the PCR product of the oligonucleotides (in contrast to the oligonucleotide itself which can't be sequenced). In order to evaluate the rate of errors the oligonucleotide PCR products were cloned and sequenced. FIG. 19 shows the sequence of the PCR product of an oligonucleotide. The oligonucleotide PCRs were cloned into pGEM-T easy vector. Few positive clones were sequenced. The sequences obtained were all identical and revealed no mistakes (FIG. 20).

Figure 21:
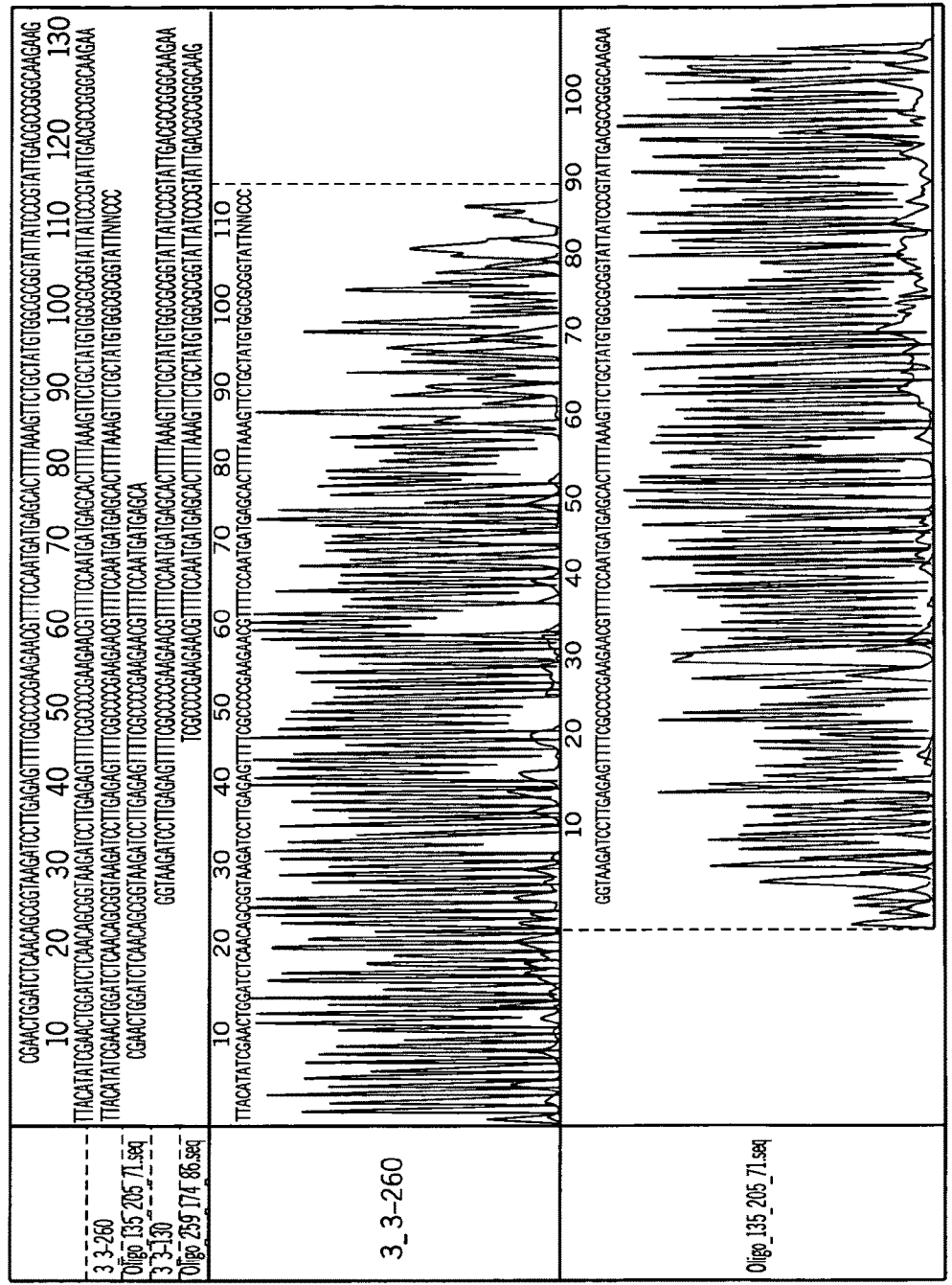
FIG. 21 shows one step elongation from two oligonucleotide PCR products before cloning, including the following sequences: 3_3-260 (SEQ ID NO:9), Oligo_135_205_71.seq (SEQ ID NO:10), and 3_3-130 (SEQ ID NO:11).
Figure 22B:
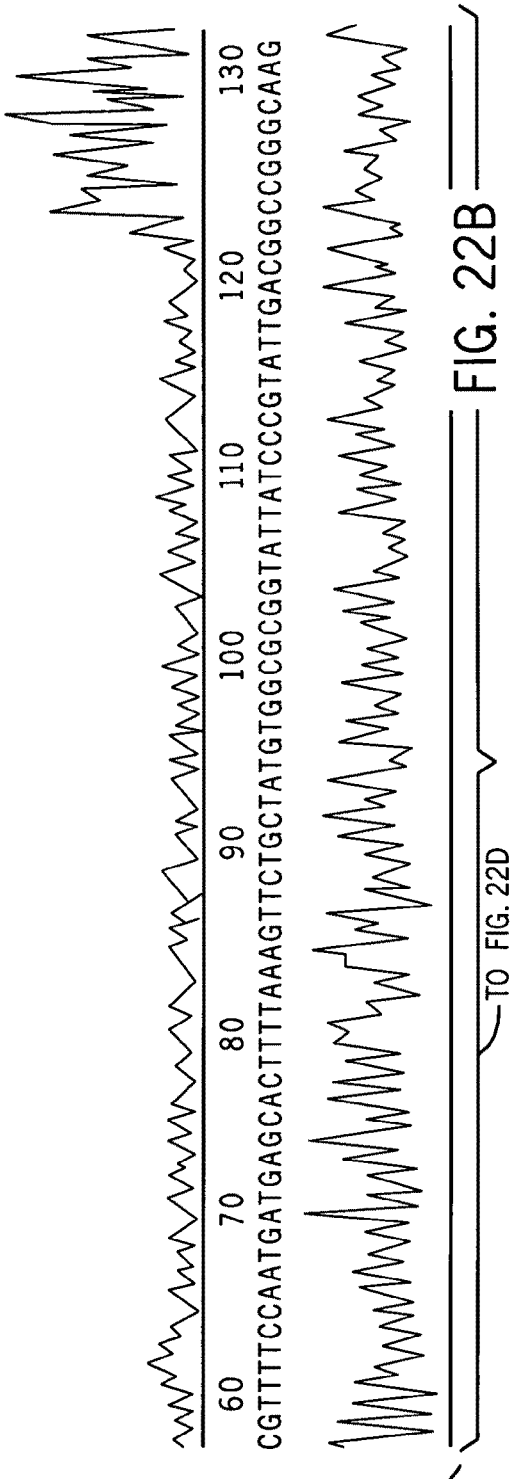
FIG. 22 shows an alignment of cloned sequences of one step elongation from 2 oligonucleotide PCR products, including the following sequences: 45-Sp6 (SEQ ID NO:12), 48-Sp6 (SEQ ID NO:13), 46-Sp6 (SEQ ID NO:14), 44-Sp6 (SEQ ID NO:15), 43-Sp6 (SEQ ID NO:16), 47-Sp6 (SEQ ID NO:17) and Oligo_135_205_71.seq (SEQ ID NO: 10)
Figure 22C:
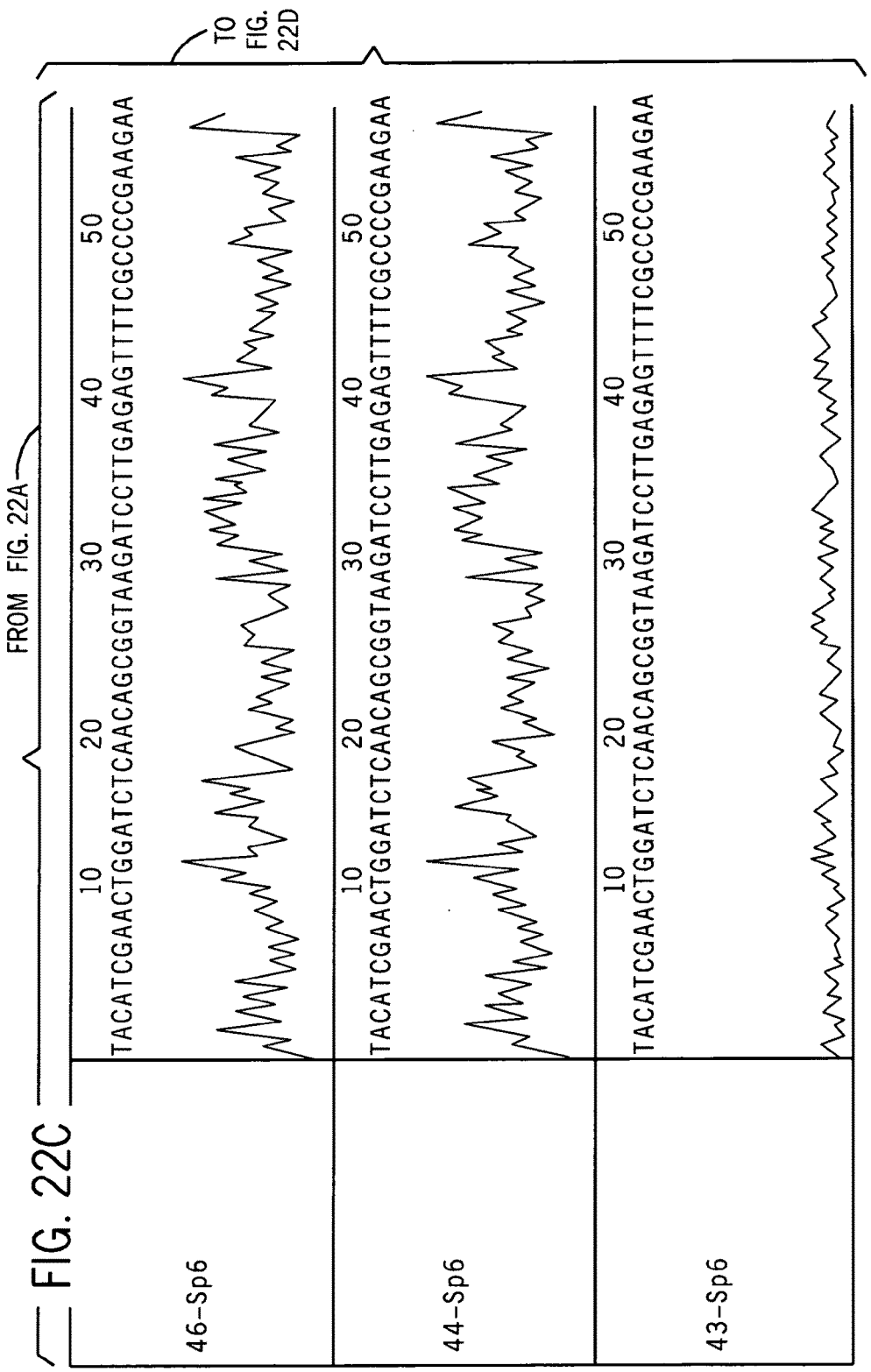
Figure 22D:
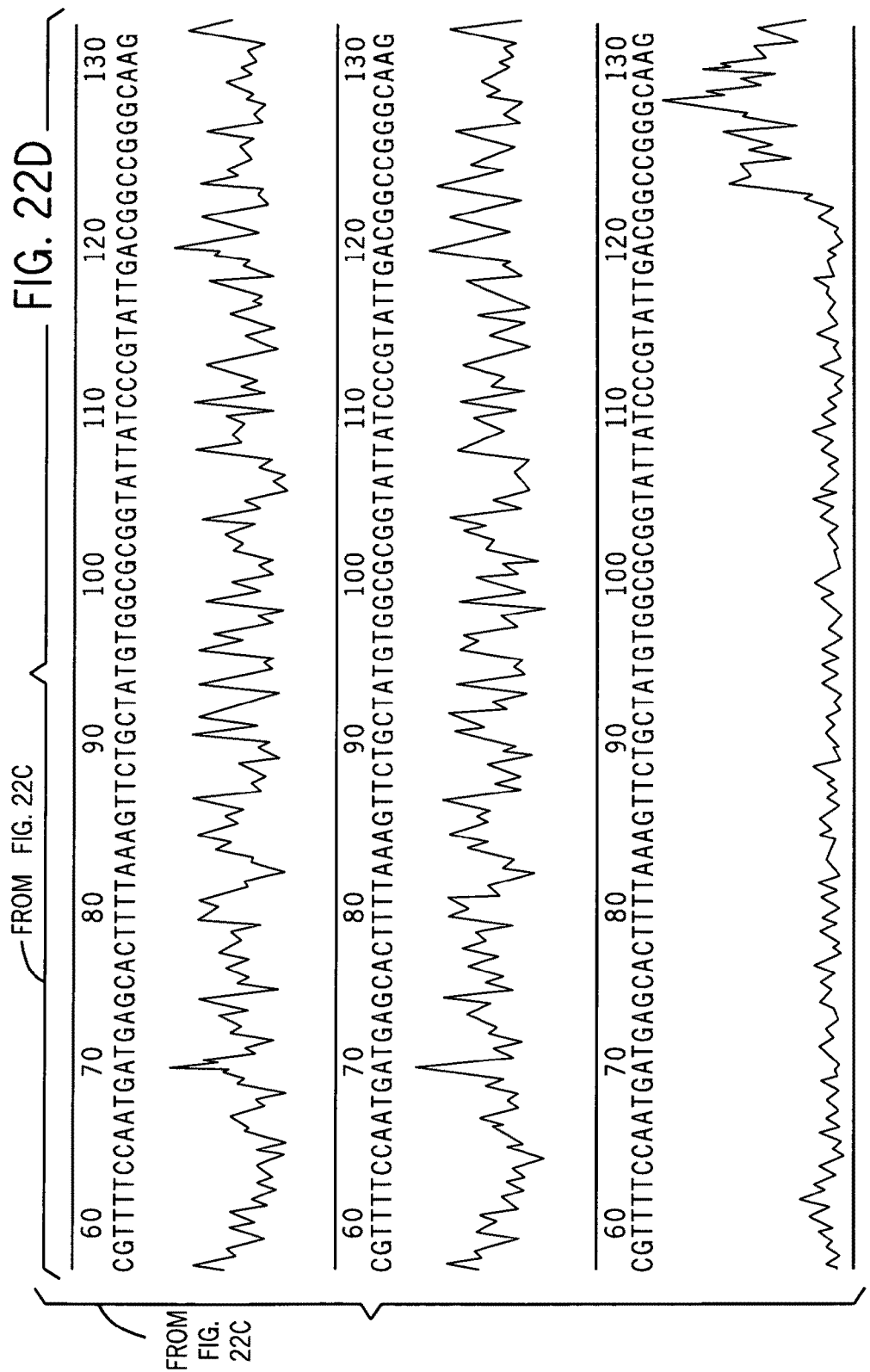
Figure 23:
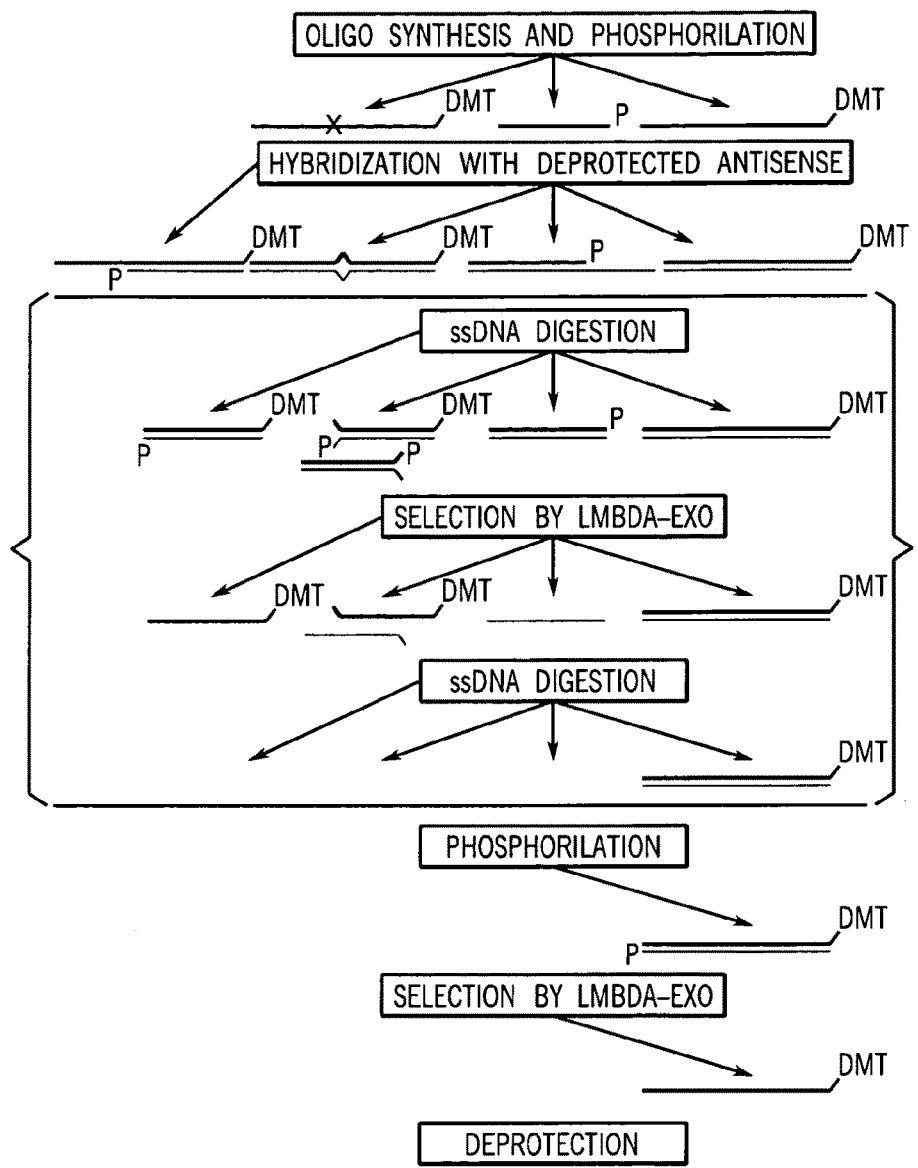
FIG. 23 shows oligonucleotide selection and purification.
Figure 24:
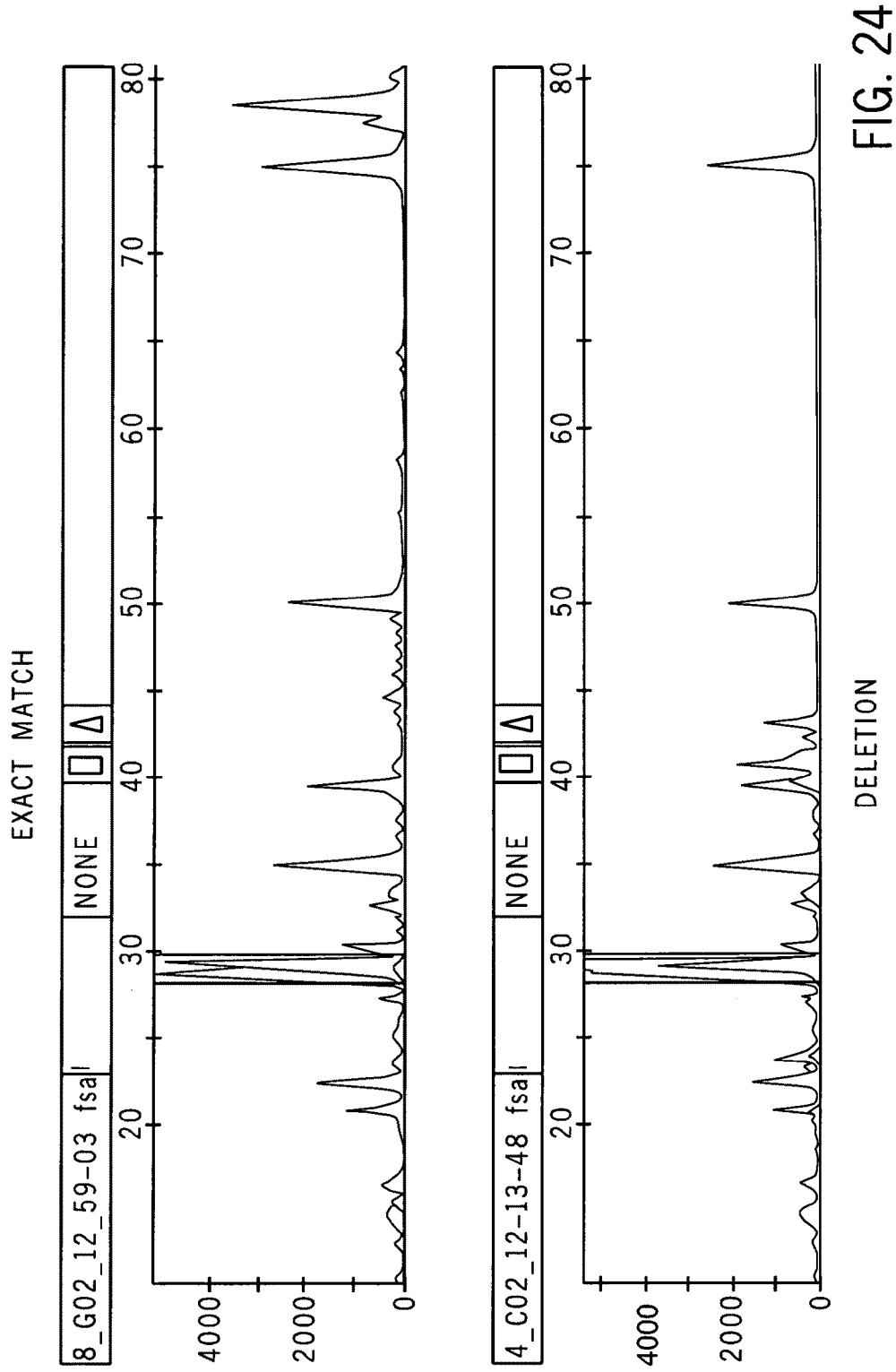
FIG. 24 shows experimental results of enzymatic mismatch cleavage by T7 Endonuclease; only upon a mismatch, there is digestion of the DNA duplex by the endonuclease. The orange color represents the marker, the green color represents the DNA substrate.

The elongated products obtained from the oligonucleotide PCRs were sequenced and found to be correct (FIG. 21). In addition the elongated products were cloned and sequenced. The cloned sequences were all correct and identical to the expected ones (FIG. 22).

All the data received so far has opened the way for the realization of this method on fully automatic platform and start to work on synthesis of specifically defined combinatorial libraries. A laboratory liquid handling robot is currently being used (Tecan Freedom 2000). A program was developed that translates the D&C-DNA synthesis protocol to the script language of robot. The robot performs all liquid handing operations, reaction incubation, and sample collection for quality control.

Enzymatic Oligo Nucleotide Purification—

The present invention provides a method and system for optionally and preferably using synthetic oligonucleotides (also referred to herein as "oligos") for constructing much longer molecules. Such molecules have properties and characteristics to be considered for implementing the present invention.

For example, during oligo synthesis, each coupling step has an efficiency of 98 to 99%. The 1-2% of oligos that do not couple at each step are inactivated and remain in the final synthesis product; these are called n-minus products. In long oligos, the amount of n-material can be significant. As an example, consider a 75-mer synthesized with 99% efficiency at each step. The amount of full length product will be (0.99) 75=47%. The remaining 53% of the final synthesized product consists of n-products. Because synthesis proceeds from 3' to 5', the n-products consist of deletions from the 5' end. Additionally methods for generating oligonucleotides have some level of errors. There are a few basic methods of purification of oligonucleotides, including but not limited to Reverse-phase cartridge purification, HPLC Purification, PAGE purification.

The principle of Reverse-phase cartridge purification is based on the selection of full length product with the DMT group. The n−1 oligo without the DMT group will not be selected when the oligo is passed through the column.

HPLC purification removes most truncated oligo sequences. The ion exchange HPLC is used to separate the oligo sequences on the basis of charge.

PAGE separates the oligos on the basis of charge and molecular weight. PAGE purification is performed on a denaturing polyacrylamide gel containing urea. The oligo is detected through UV shadowing. The full-length product is excised and eluted from the gel.

These techniques purify the oligos from n-products but they do not solve the problem of errors and are not automated.

Experimental Results—Error Correction

As noted above, one problem of any type of oligonucleotide synthesis is the occurrence of errors. All such synthetic methods produce oligonucleotides with errors in the sequence of various types, including missed nucleotides, incorrect nucleotides, added nucleotides, premature truncation and the like. According to preferred embodiments of the present invention, there is provided a method for reducing if not eliminating such errors, preferably through an iterative error elimination process. Such a process is preferably performed as part of a recursive process of oligonucleotide construction. Recursive construction with iterative error elimination improves on previous approaches to DNA synthesis by enabling rapid, fully-automated and error-free construction of long DNA molecules. Such a method may also optionally be used to combine synthetic and natural DNA segments. Furthermore, such a method optionally enables efficient design, synthesis and error correction of combinatorial DNA libraries with shared and variant components and optionally enables synthesis of building blocks for genomes. Thus, the present invention provides a novel foundation for the study and design of synthetic biological molecules and organisms.

Figure 25:
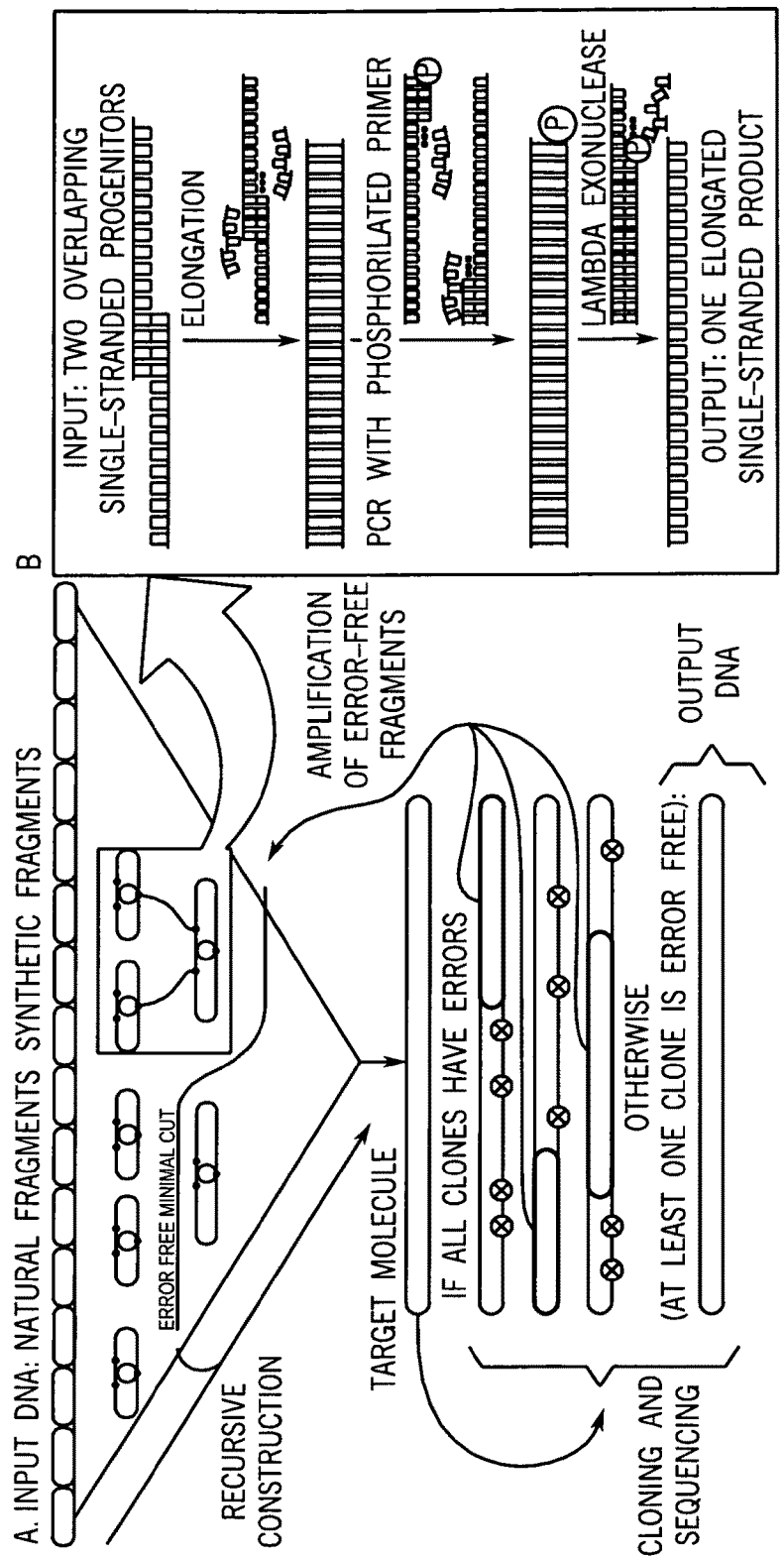
FIG. 25 shows an exemplary method with error correction according to the present invention.

According to some embodiments of the present invention, recursive construction is performed by combining pairs of smaller elements into ever larger elements until a sufficiently large element is constructed, as shown in FIG. 25A. As shown, overlapping DNA fragments from any source can be used as input for recursive construction (top). A mixture of natural and synthetic fragments is shown for the purpose of description and without any intention of being limiting, as only natural or only synthetic fragments may optionally be used. ssDNA fragments are recursively combined to form the target molecule (center), which is cloned and sequenced. If there is an error-free clone, then this clone forms the output of the process and the process terminates (bottom). Otherwise a set of error-free fragments of the clones that constitute a minimal cut of the recursive construction tree are used as inputs to the next iteration of the construction process, which is typically shorter and produces an output with no or at least fewer errors than the previous iteration.

An exemplary but preferred embodiment of the inner stages of the process of recursive construction is shown in FIG. 25B. To enable recursion, the composition operation is designed so that its output is of the same type as its two inputs. For example, a composition reaction that takes two overlapping ssDNA fragments as input and produces the corresponding elongated dsDNA molecule as output cannot be used recursively, since the output dsDNA molecule is not a proper input for the next composition reaction. For the same reason, a reaction that takes two overlapping dsDNA molecules as input and produces as output a mixture of the input molecules and some elongated dsDNA molecules cannot be used recursively, since, by definition, such a mixture is not a legal input to the composition reaction. To address this core requirement of recursive construction, a novel composition reaction is used that takes two overlapping ssDNA fragments as input and produces an elongated ssDNA molecule as output, shown in FIG. 25B.

As shown, two input overlapping ssDNA fragments hybridize and prime each other for an elongation reaction to form a dsDNA fragment, which is amplified by PCR with one of the two primers phosphorylated at its 5'-end. The phosphate-labeled PCR strand is then degraded with Lambda exonuclease, yielding an elongated ssDNA fragment as output. The process of recursive construction then continues as described.

The output of a recursive construction process may contain faults, or errors, which may optionally have been present already in the input elements and/or introduced by the construction process itself. This problem is solved by the present invention through exploiting the specific nature of DNA. The constructed molecule (constructed according to the process of FIG. 25) is cloned and sequenced, as in other DNA construction protocols known in the art. If one of the clones is error free, it is the output of the process. Otherwise, the error-free fragments of the clones are preferably identified and are preferably used to compute a minimal cut as described above through the recursive construction tree. The minimal cut is a set of maximal-length error-free fragments of the clones, with boundaries that coincide with boundaries of fragments of the initial recursive construction tree, that can serve as better (longer and more accurate) inputs to the next iteration of the construction process. This sharing of boundaries assures that minimal-cut fragments can be "lifted" from clones with PCR utilizing the same primers as in the corresponding composition step (FIG. 25B) of the recursive construction process.

Unless otherwise stated, the below examples relate to methods of recursive construction as described herein, for example with regard to the D&C protocols and other protocols as described herein.

Example

GFP Synthesis

The process of recursive construction of a particular molecule, the 783 nt-long gene GFP and its iterative error correction is shown in FIG. 26. More detailed materials and methods are given below.

Figure 26A:
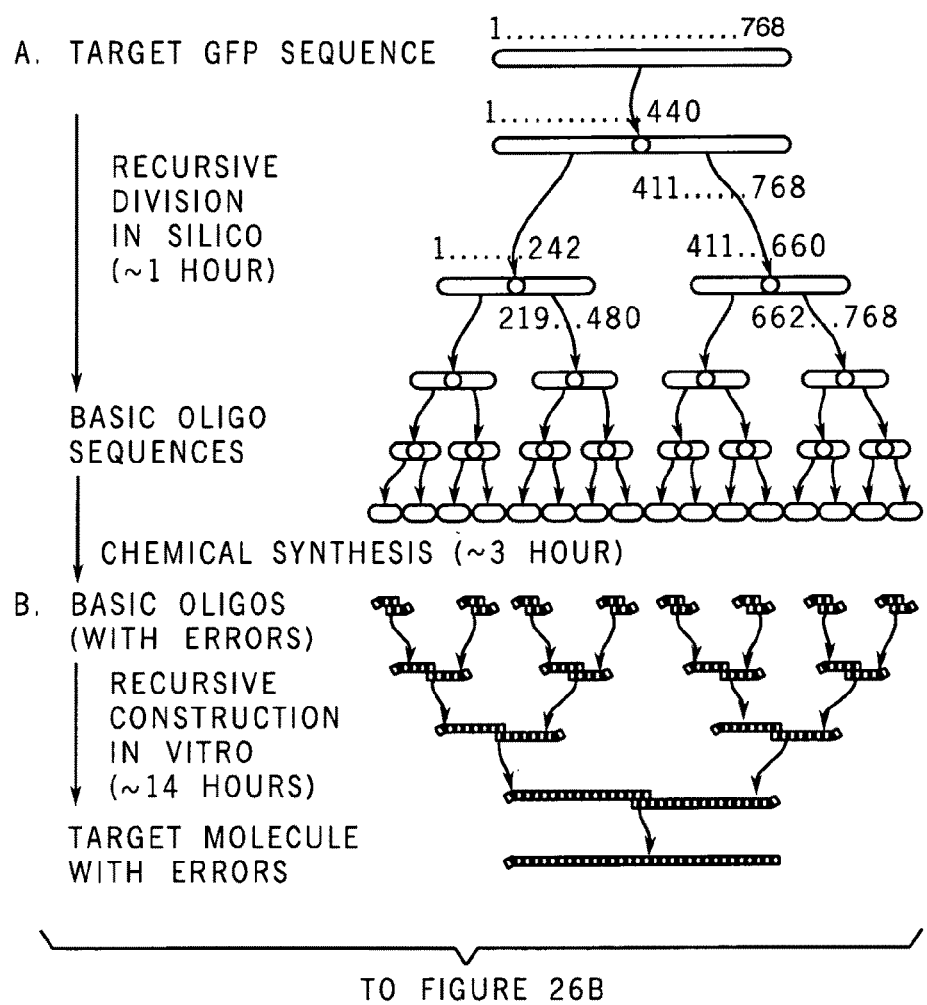
FIG. 26 shows an exemplary method for synthesis of the GFP gene.

The target GFP sequence was recursively divided in silico into basic oligo sequences using D&C (FIG. 26A). The target sequence is fed into a construction-protocol-generating algorithm that recursively divides the target sequence into basic overlapping oligos using D&C, a process as described herein.

The algorithm finds an optimal solution for DNA construction according to thermodynamic constraints (affinity, specificity etc), construction tree topology and a cost function (number of oligos, overlap length etc). Each node in the tree of the divided GFP sequence represents two overlapping DNA sequences, with overlaps delimited in the center of each node.

Basic DNA building blocks from in silico division were made (with errors) by conventional oligonucleotide synthesis and used as inputs for recursive construction in vitro (FIG. 26B). If any fragment of the target sequence is available as natural DNA (for example in a plasmid), then the algorithm can take this information into account and use this natural fragment in the construction instead of synthesizing it from basic oligonucleotides (see FIGS. 25A, 26B).

Figure 27A:
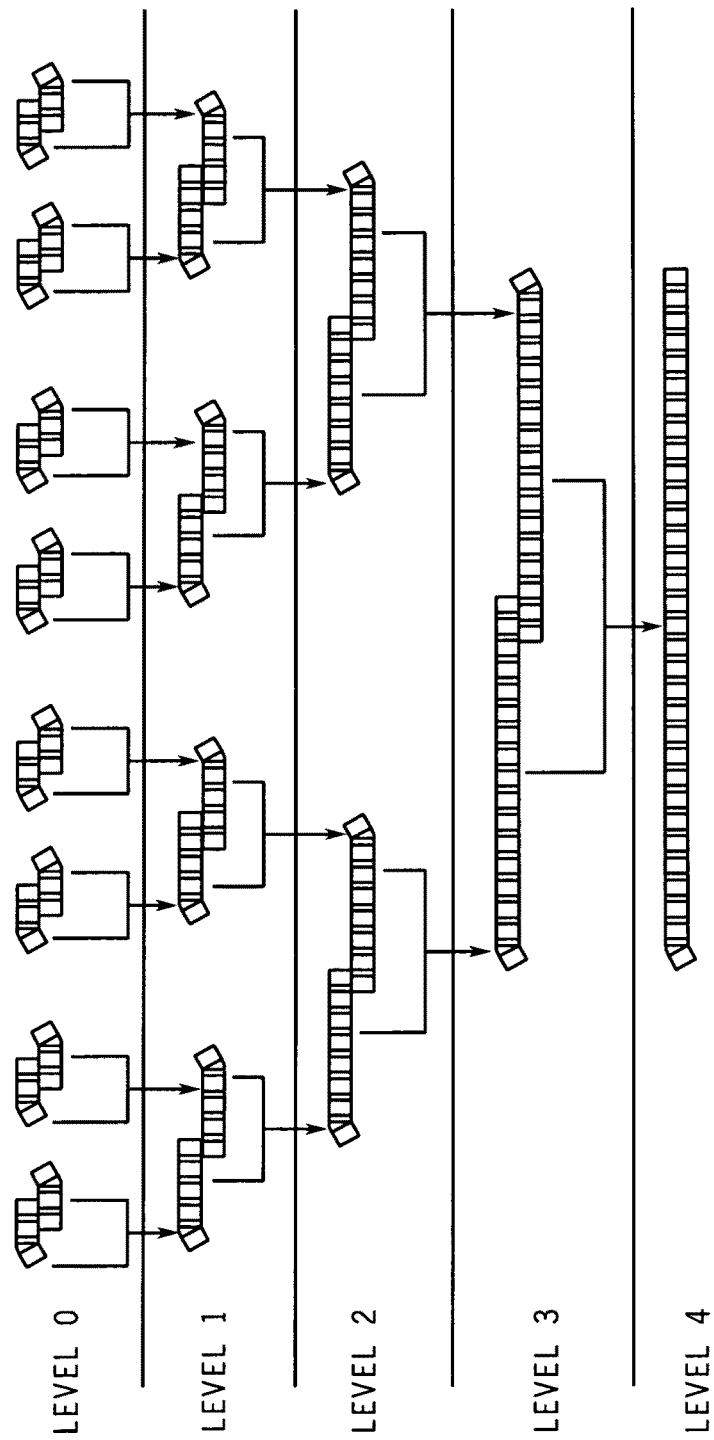
FIG. 27A-E shows the C.E fragment analysis after PCR reactions during the construction of GFP.
Figure 27B:
Figure 27B:
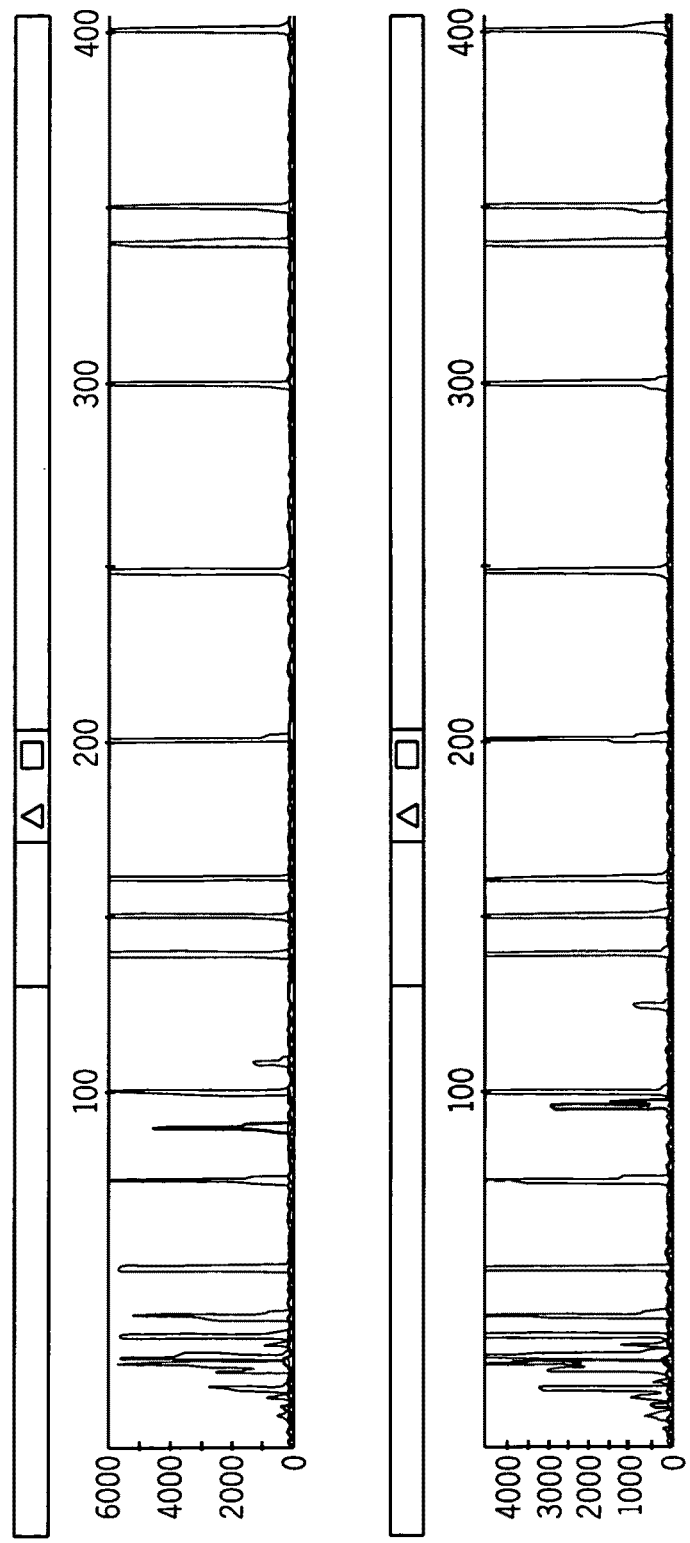
Figure 27C:
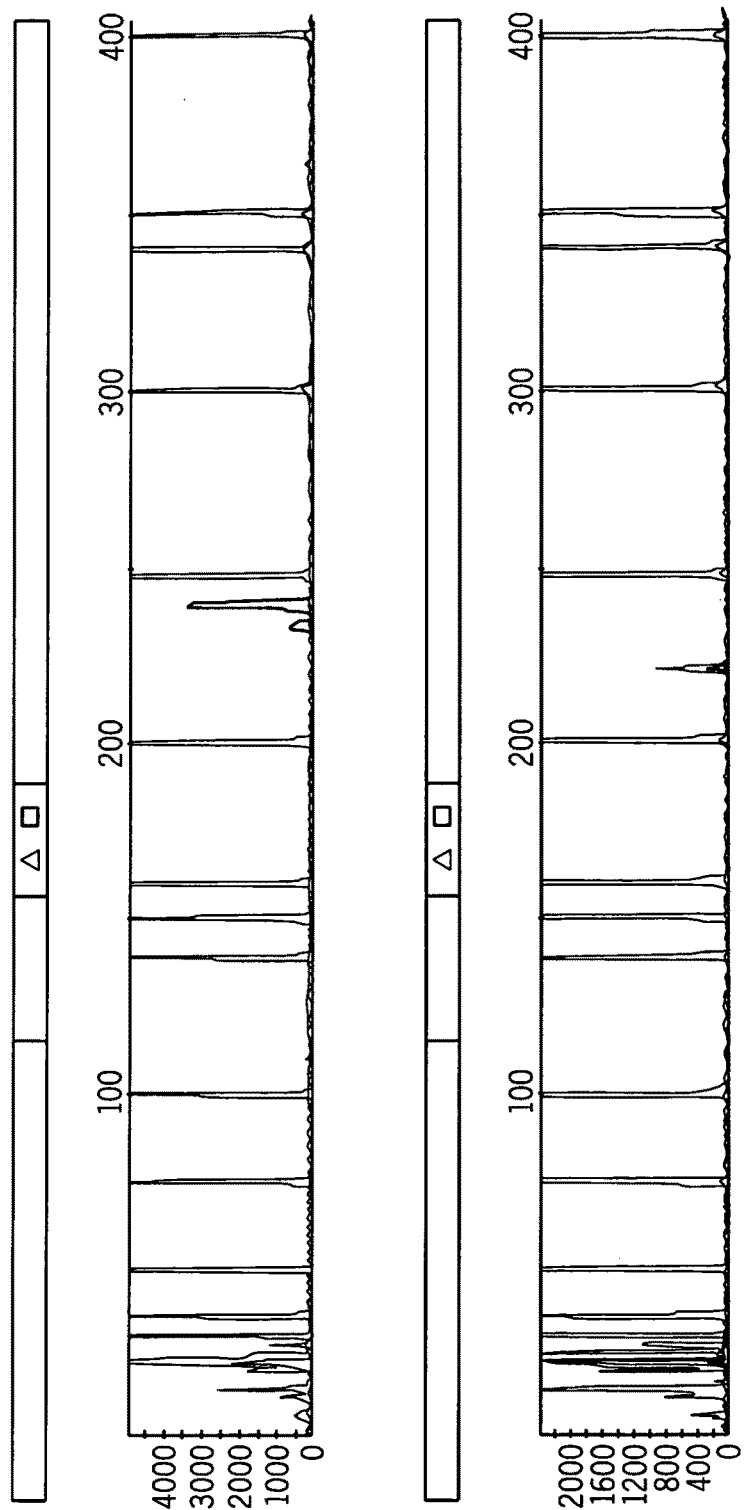
Figure 27C:
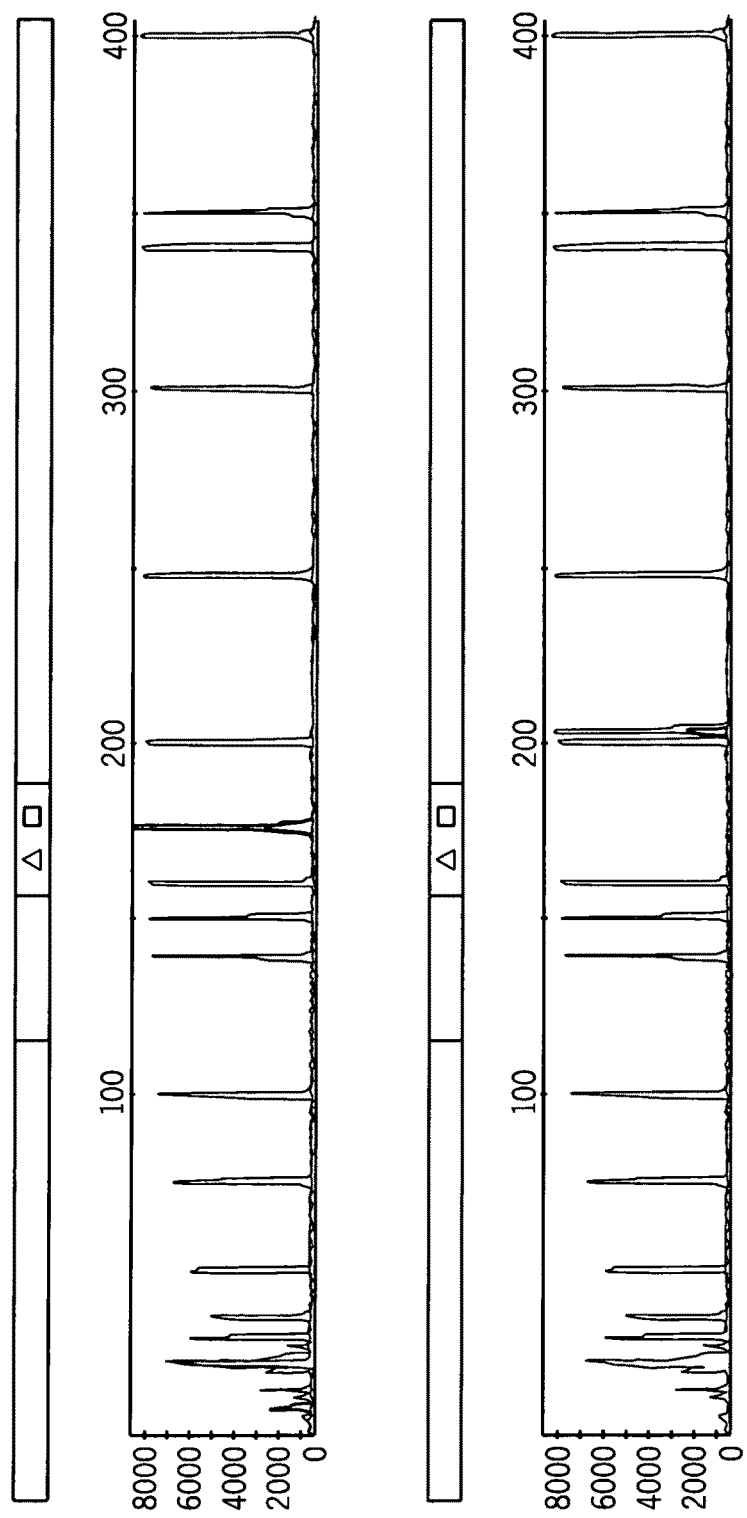
Figure 27D:
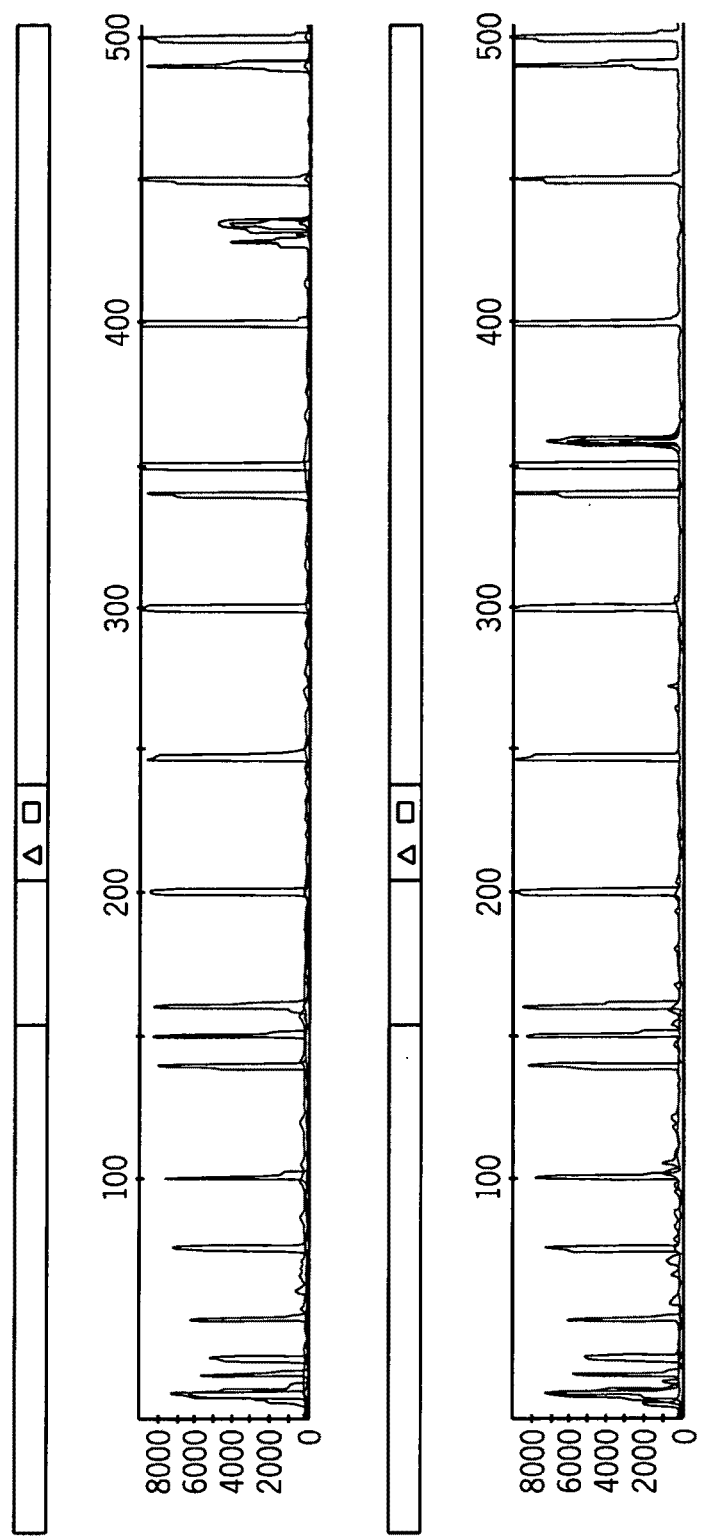
Figure 27E:
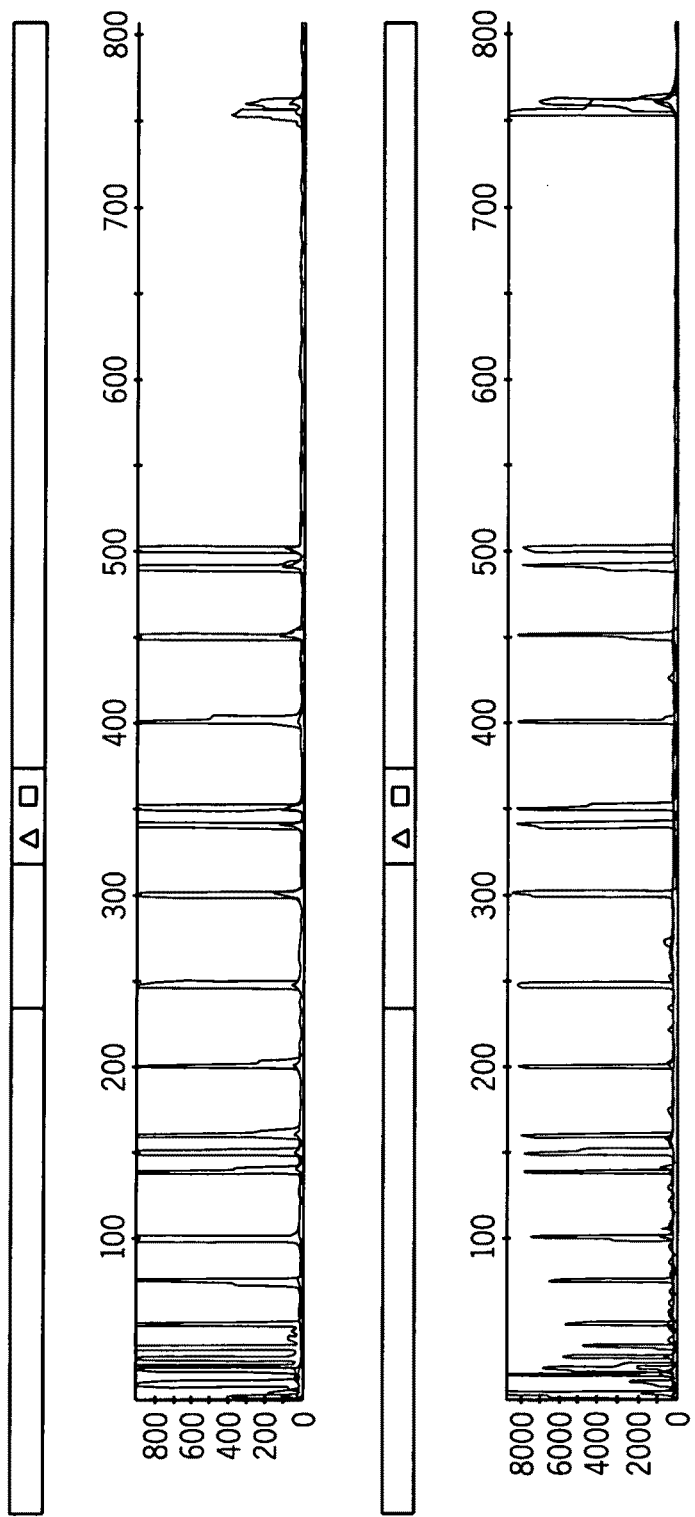
Figure 28A:
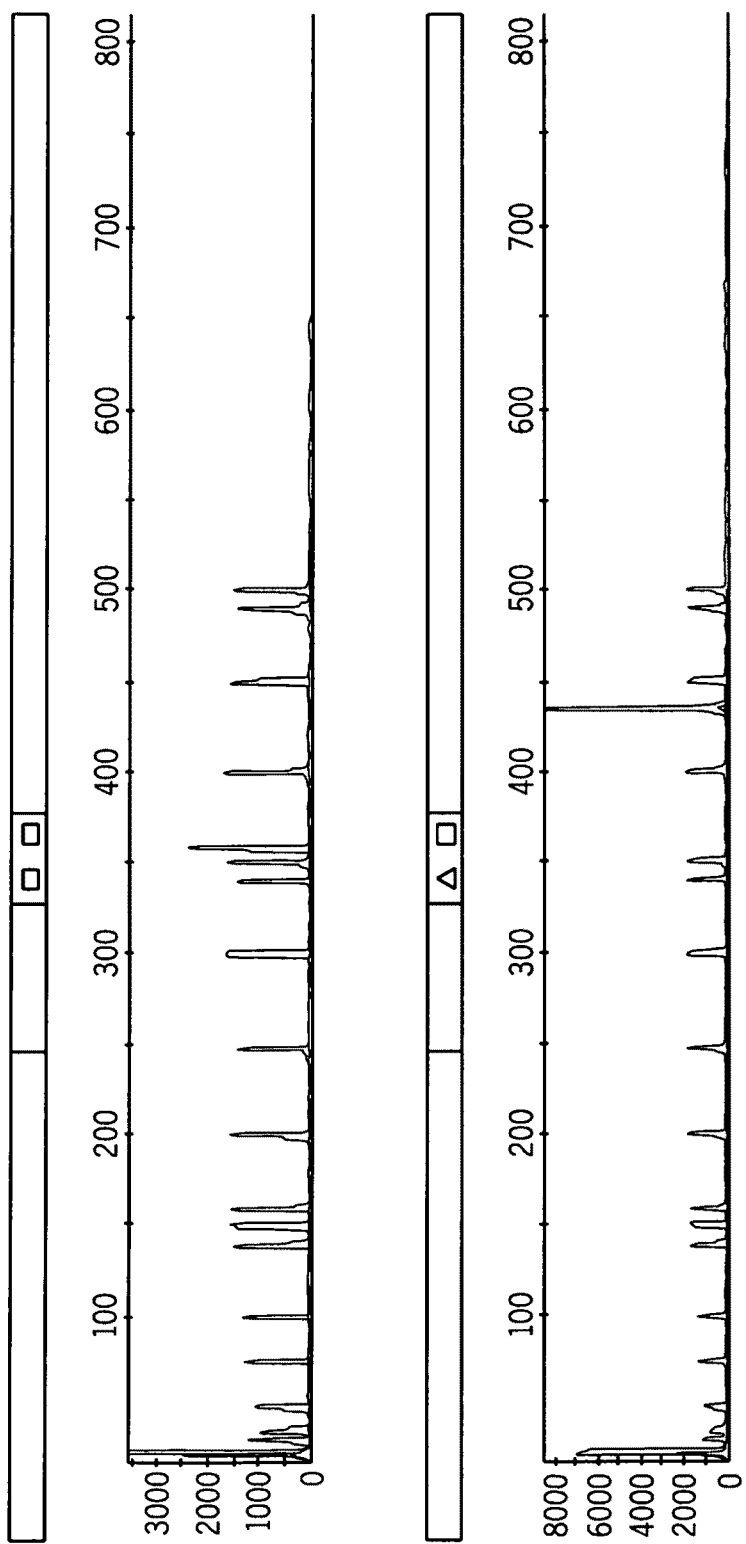
FIG. 28A-B shows the C.E fragment analysis after PCR reactions during the construction of GFP from two fragments.
Figure 28B:
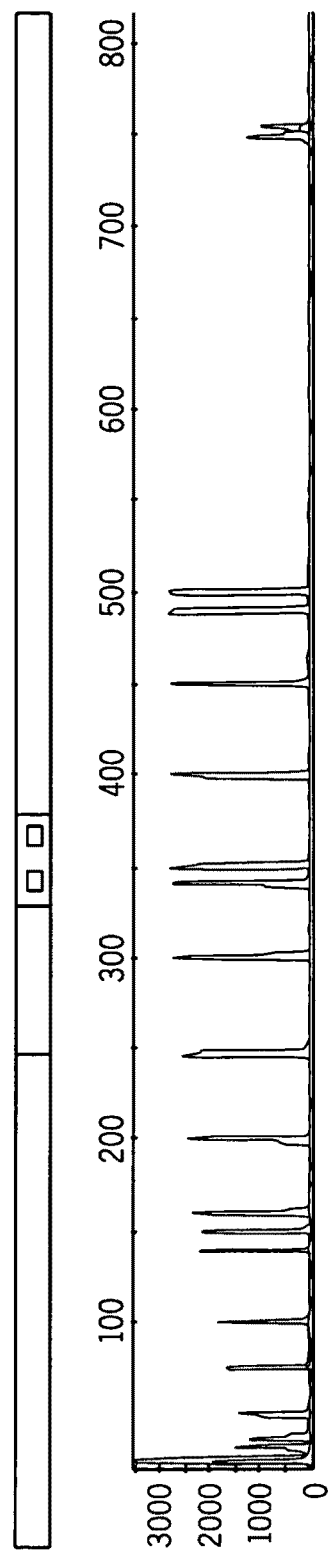
Figure 29:
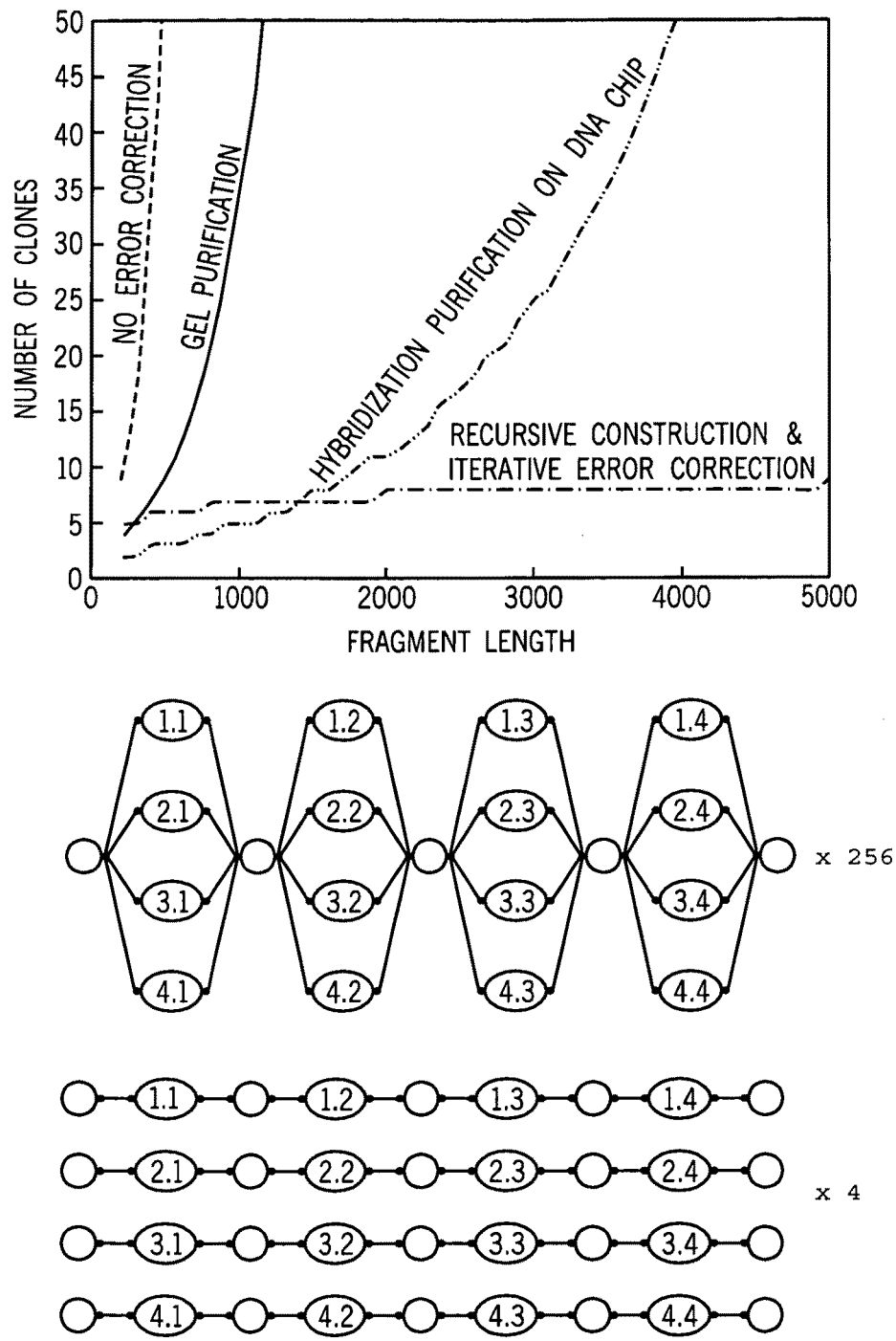
FIG. 29 shows errors vs. target length for clones.

Recursive construction was performed, using these oligonucleotides, until full length GFP molecules (expected to be erroneous) were formed (see FIGS. 27-29 for results, as described below). The algorithm of FIG. 26B also generates a liquid-handling robot control program, using a language developed by the inventors, that executes the construction protocol (see FIG. 25B). The program instructs the robot to automatically construct the GFP gene using standard off-the-shelf reagents. The protocol actually used in the experiments includes procedures that were performed manually due to limitations of the laboratory equipment but which could be optionally performed automatically (see materials and methods). Light and dark blue correspond to sense and antisense strands of recursively combined DNA. Erroneous target GFP molecules were cloned, sequenced and errors (marked with red) were identified (FIG. 26C). A minimal cut from error free sequences (non-faded, below minimal cut line) of the original construction process was computed in silico from an ensemble of three error prone clones. Fragments constituting this minimal cut (black brackets on clones) were amplified from the clones and used as inputs to recursive reconstruction in vitro according to the minimal cut. This resulted in a target GFP clone with no errors (FIG. 26D).

Recursive construction of a 3 Kb DNA fragment was carried out using this synthetic GFP construct and DNA from a natural (bacterial plasmid) source as inputs for the recursive construction process. This yielded an error free target 3 Kb molecule (FIG. 26E).

Materials and Methods—

A more detailed description of the Materials and Methods is provided in this section.

Phosphorylation:

300 pmol of 5' DNA termini in a 50 μl reaction containing 70 mM Tris-HCl, 10 mM MgCl$_2$, 7 mM dithiothreitol, pH 7.6 at 37° C., 1 mM ATP, 10 units T4 Polynucleotide Kinase (NEB). Incubation is at 37° C. for 30 min, inactivation 65° C. for 20 min.

Elongation (ABgene):

1-5 pmol of 5' DNA termini of each progenitor in a reaction containing 25 mM TAPS pH 9.3 at 25° C., 2 mM MgCl$_2$, 50 mM KCl, 1 mM β-mercaptoethanol 200 μM each of dNTP, 4 units Thermo-Start DNA Polymerase (ABgene). Thermal Cycler program is: Enzyme activation at 95° C. 15 min, slow annealing 0.1° C./sec from 95° C. to 62° C., elongation at 72° C. for 10 min.

Elongation (BioLINE):

1-5 pmol of 5' DNA termini of each progenitor in a reaction containing 60 mM Tris-HCl pH 8.3 at 25° C., 6 mM (NH$_4$)$_2$SO$_4$, 10 mM KCl, 2 mM MgSO$_4$, 200 μM each of dNTP, 5 units AccuSure DNA Polymerase (BioLINE). Thermal Cycler program is: Enzyme activation at 95° C. 10 min, slow annealing 0.1° C./sec from 95° C. to 62° C., elongation at 72° C. for 10 min.

PCR (ABgene):

1-0.1 fmol template, 10 pmol of each primer in a 25 μl reaction containing 25 mM TAPS pH 9.3 at 25° C., 2 mM MgCl$_2$, 50 mM KCl, 1 mM β-mercaptoethanol 200 μM each of dNTP, 0.9 units Thermo-Start DNA Polymerase (ABgene). Thermal Cycler program is: Enzyme activation at 95° C. 15 mM, Denaturation 95° C., Annealing at Tm of primers, Extention 72° C. 1 min per kb to be amplified 20 cycles.

PCR (BioLINE):

1-0.1 fmol template, 10 pmol of each primer in a 25 μl reaction containing 25 mM TAPS pH 9.3 at 25° C., 2 mM MgCl$_2$, 50 mM KCl, 1 mM β-mercaptoethanol 200 μM each of dNTP, 1.9 units AccuSure DNA Polymerase (BioLINE). Thermal Cycler program is: Enzyme activation at 95° C. 10 min, Denaturation 95° C., Annealing at Tm of primers, Extention 72° C. 1.5 min per kb to be amplified 20 cycles.

Lambda Exonuclease:

1-5 pmol of 5' phosphorylated DNA termini in a reaction containing 25 mM TAPS pH 9.3 at 25° C., 2 mM MgCl$_2$, 50 mM KCl, 1 mM β-mercaptoethanol 5 mM 1,4-Dithiothreitol, 5 units Lambda Exonuclease (Epicentre). Thermal Cycler program is 37° C. 15 min, 42° C. 2 min, Enzyme inactivation at 70° C. 10 min.

Automated DNA Purification:

Automated DNA Purification was performed with QIAGEN's QIAquik 96 well PCR purification kit using standard protocol that was adapted to work with Tecan freedom 200 and a vacuum manifold.

Protocol Automation

Automated protocol was performed as described herein by a Tecan Freedom 2000 robot.

DNA Purification:

Manual DNA Purification was performed with QIAGEN's MinElute PCR purification kit using standard procedures.

Cloning

Fragments were cloned into the pGEM T easy Vector System I from PROMEGA using standard procedures. Vectors containing cloned fragments were transformed into JM109 competent cells from PROMEGA1 using standard procedures.

Results—

FIG. 27 shows the C.E fragment analysis after PCR reactions during the construction of GFP. FIG. 27A shows the overall construction protocol of GFP molecule divided to levels of construction. FIG. 27B shows that at GFP construction level 1, each C.E. contain two fragments that will be elongated together in the next level. FIGS. 27C and 27D show the results of GFP construction levels 2 and 3, respectively. FIG. 27E shows the results of GFP construction level 4 and control PCR on pGFP-N1.

The first iteration of the recursive construction process resulted in target clones with an error rate of 1\160 (FIG. 29A), reflecting the known error rate of their oligonucleotide building blocks. Given that errors are distributed randomly with a known rate, the minimal number of clones needed to obtain an error-free minimal cut may be calculated with high probability as described above (>95%).

The minimal cut for the GFP sequence was computed using three clones (FIG. 26). The error-free fragments constituting the minimal cut were lifted by PCR and used as input for a second iteration of recursive construction, which resulted in an error-free clone. From the clones produced in the first iteration it would have been possible to choose only a pair of clones for reconstruction, one for each half of the target molecule, but three were chosen, one contributing about a half and two contributing about a quarter each of the target molecule, for illustrative purpose. The clones produced in the second iteration show an error rate of <1/5000.

The recursive construction protocol can be used for multi-kilobase constructions and can also integrate DNA from any source and at any stage into the construction process. To illustrate this, a ~3 Kb long molecule was recursively constructed from the 768 nt-long previously constructed synthetic GFP molecule and two fragments lifted from a natural plasmid, one 700 nt-long and the other 1700 nt-long (FIG. 26E). Since the input fragments were error-free, the 3 Kb clones were also error-free, such that further error-correction was not needed. Results are shown with regard to FIG. 27 (FIG. 27A shows the results after the first level of construction while FIG. 27B shows the results after the second level of construction).

Example

Combinatorial Library Construction

Advances in de novo DNA construction hold great promise for biopolymer engineering. DNA libraries are an important source from which molecules encoding novel genetic sequences can be selected. These in turn may encode novel polymers for use in medicine, research and industry. Numerous methods for constructing large libraries, mostly by random recombining and mutagenesis of DNA have been developed for directed evolution. On the other hand, in the computation-intensive practice of rational design only a small number of non-random pre-specified constructs, typically generated by site directed mutagenesis are investigated experimentally. The exemplary DNA construction method of the present invention can potentially and optionally be extended to produce large-scale rationally-designed combinatorial DNA libraries with pre-specified members.

Figure 30B:
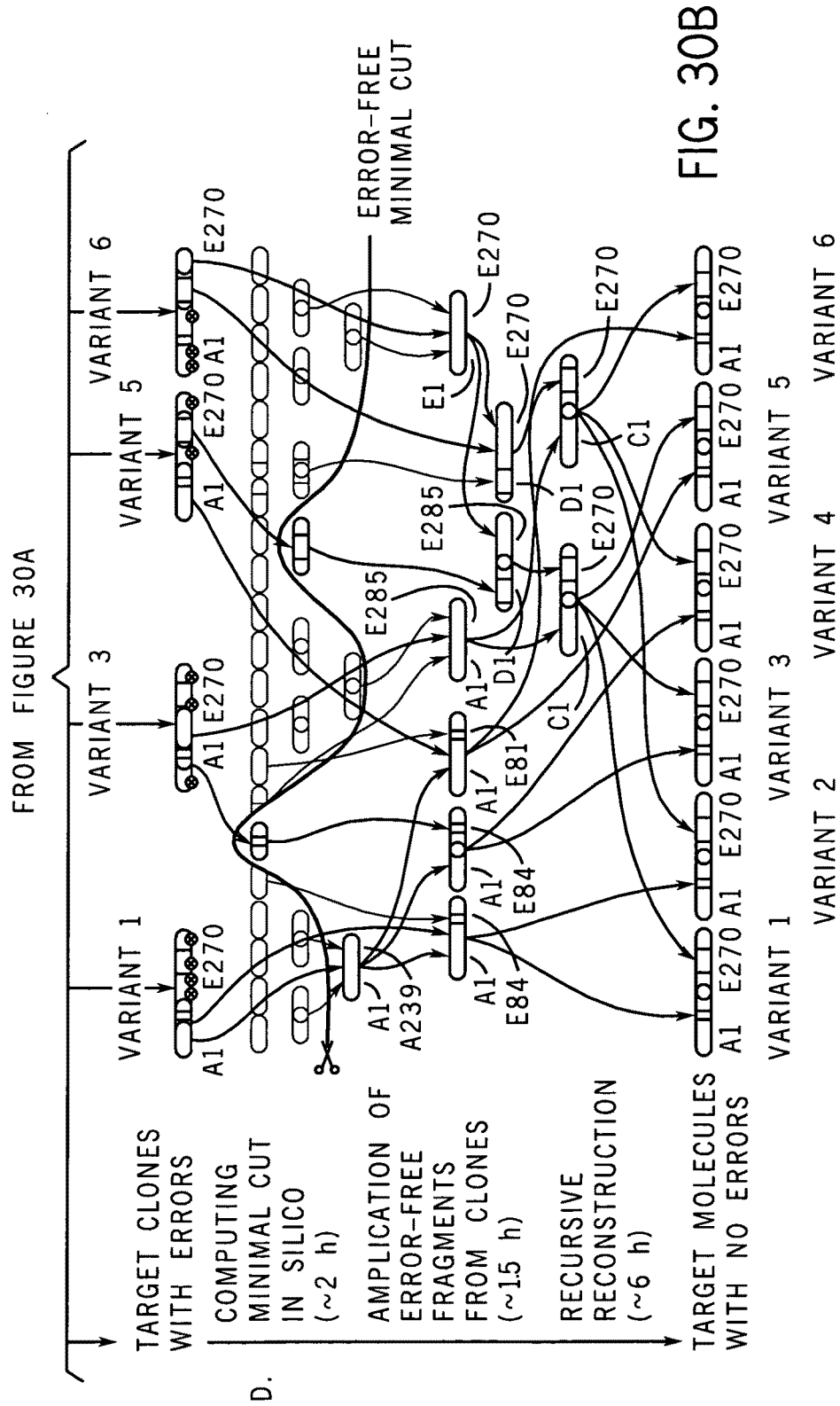
FIG. 30, part A, shown in FIG. 30A shows six predefined variants of the p53 gene (shared (gray) and unique (colored) components of the p53 combinatorial DNA library are shown)

An example of construction of a library is given herein with regard to FIGS. 30A and 30B. The library contains six pre-defined variants of the p53 gene, specified in FIG. 30A, part A, (shared (gray) and unique (colored) components of the p53 combinatorial DNA library are shown). FIG. 30A, parts B and C, and FIG. 30B, part D, show a graph depicting the library construction process corresponding to D&C based in silico division.

The process was performed as follows. First, target library DNA sequences were analyzed in silico and unique segments shared between library members were identified. These segments were further divided into overlapping oligonucleotides (FIG. 30B). The recursive division algorithm searched for an optimal library construction protocol based on chemical constraints and a cost function, in order to minimize the number of components and reactions needed to construct the entire library (FIG. 30B).

All six different p53 genes were recursively constructed from basic oligos (FIG. 30B top), and the resulting molecules were cloned and sequenced (FIG. 30B bottom). An error-free minimal cut of the entire library was computed from only four clones, and a second iteration of the process using fragments constituting this minimal cut produced error-free clones of all six library members. It is worth noting that the error-rate of the clones in the first iteration was, as expected, 1\160, and that error-free fragments totaling 1000 nt were sufficient to generate in the second iteration a complete error-free library with about 5200 nt (FIG. 30A, part C and FIG. 30B, part D).

The clones produced in the second iteration showed an error rate better than 1/5800, computed over 86,000 nt of sequenced clones.

Figure 31A:
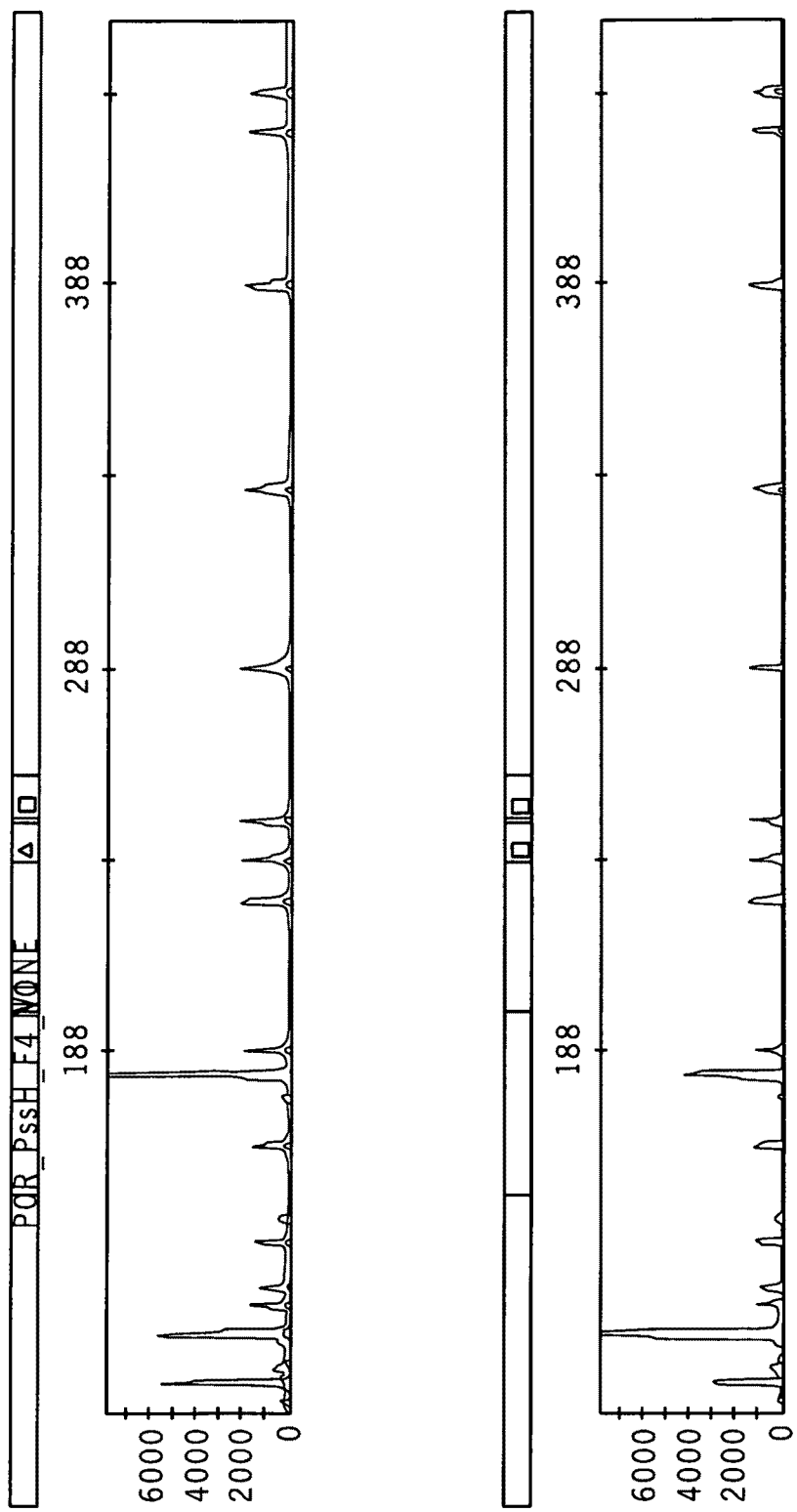
FIGS. 31Aa-Fb shows C.E fragment analysis after PCR reactions during the P53 library construction method as performed above.
Figure 31A:
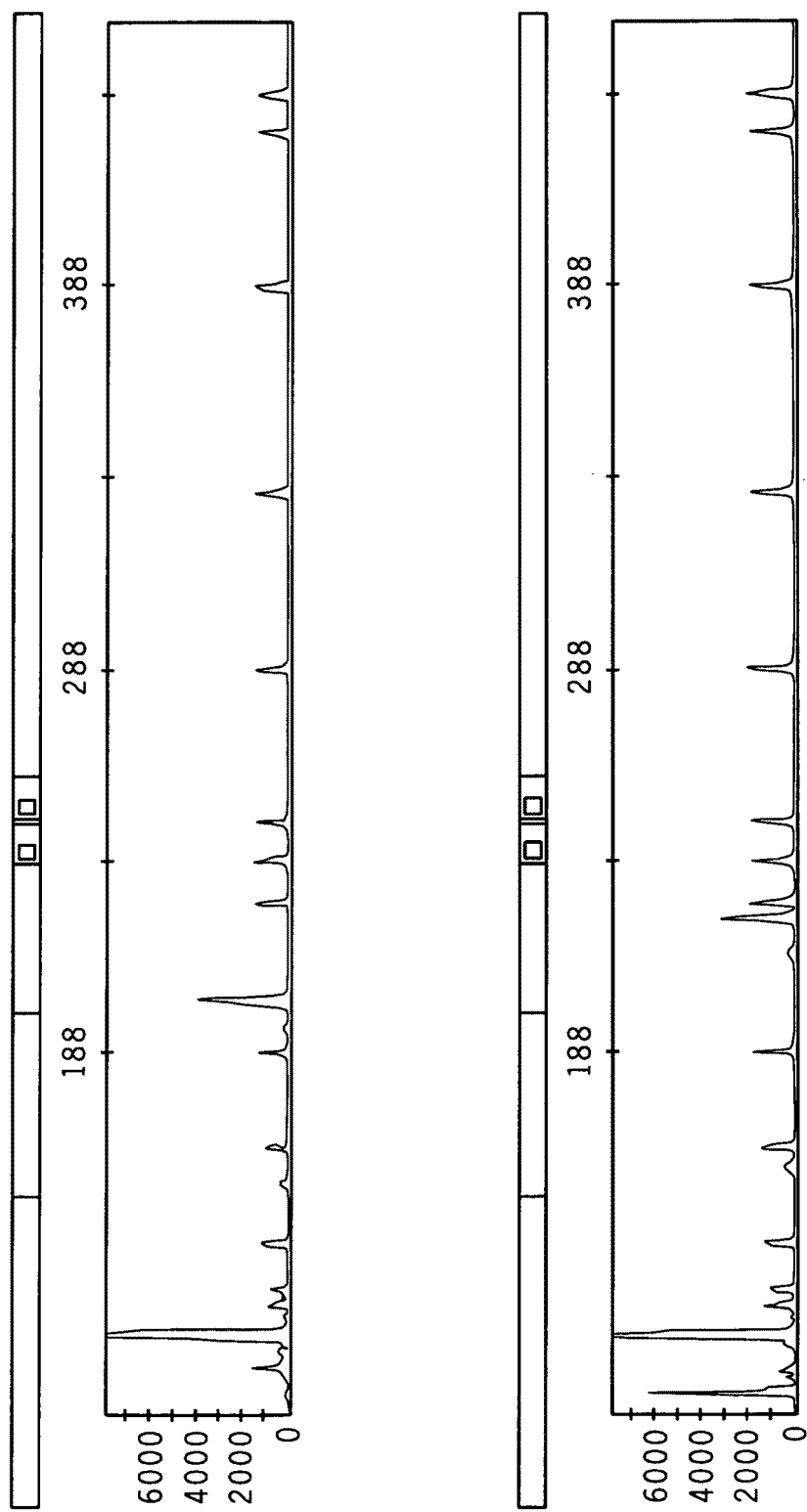
Figure 31A:
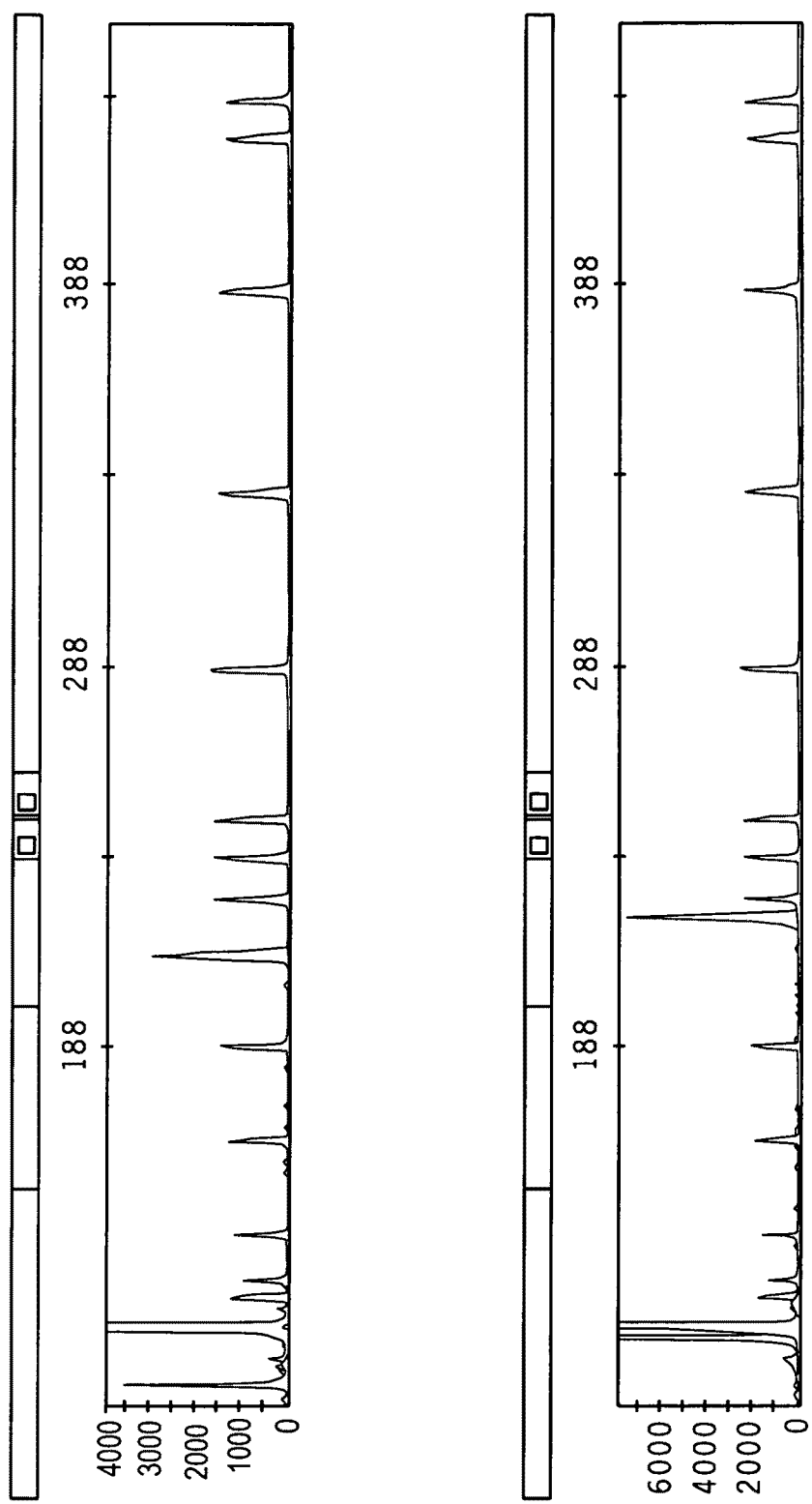
Figure 31B:
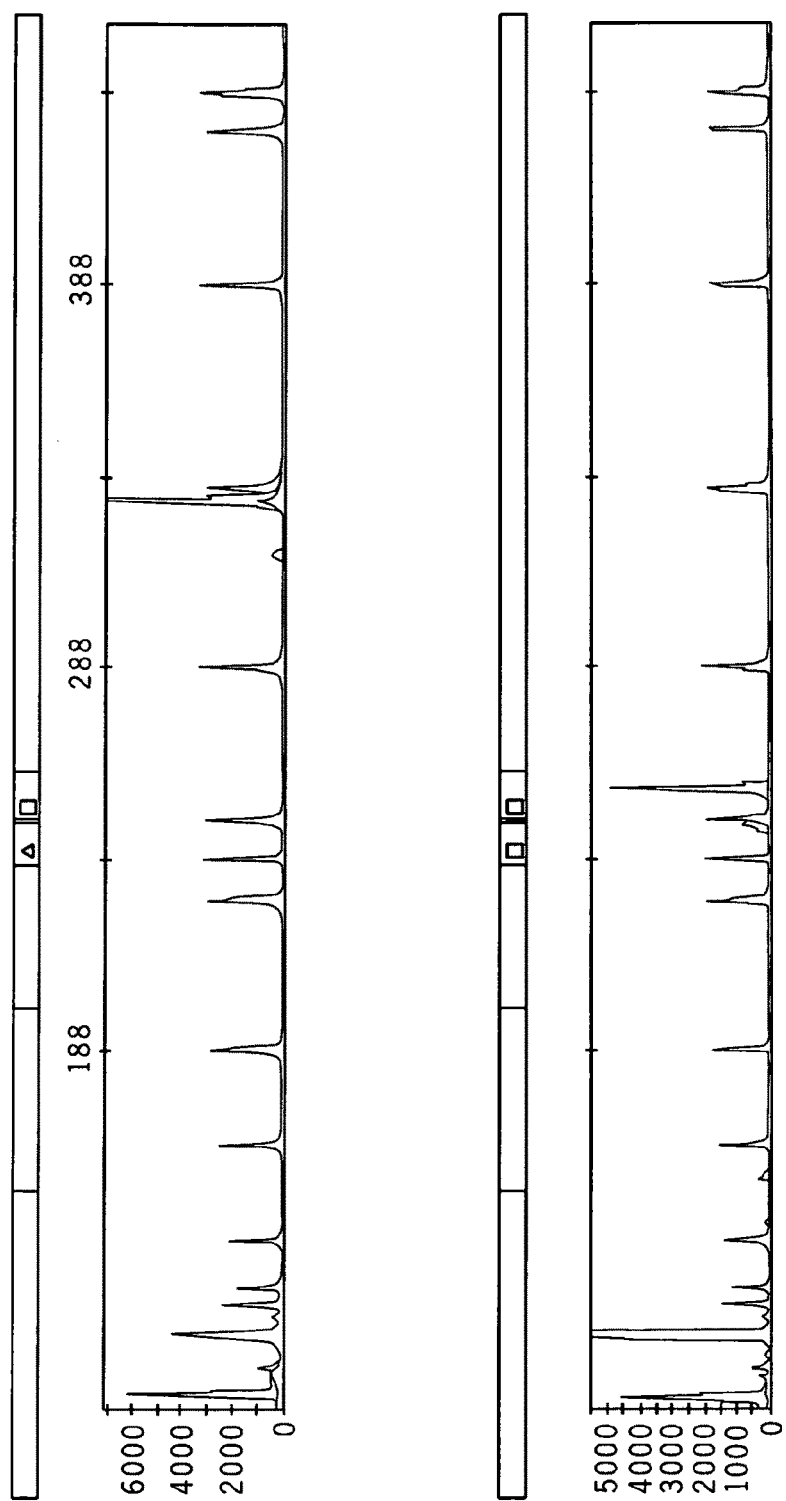
Figure 31B:
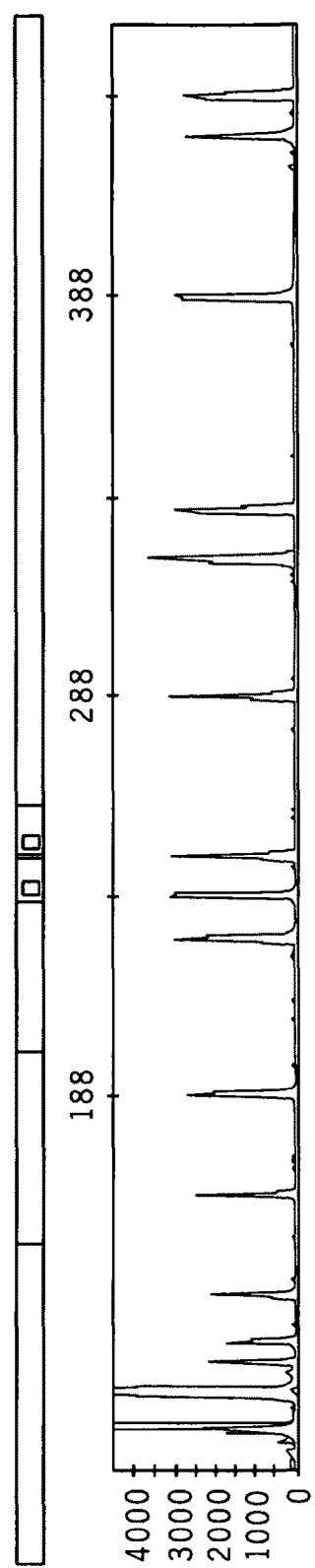
Figure 31C:
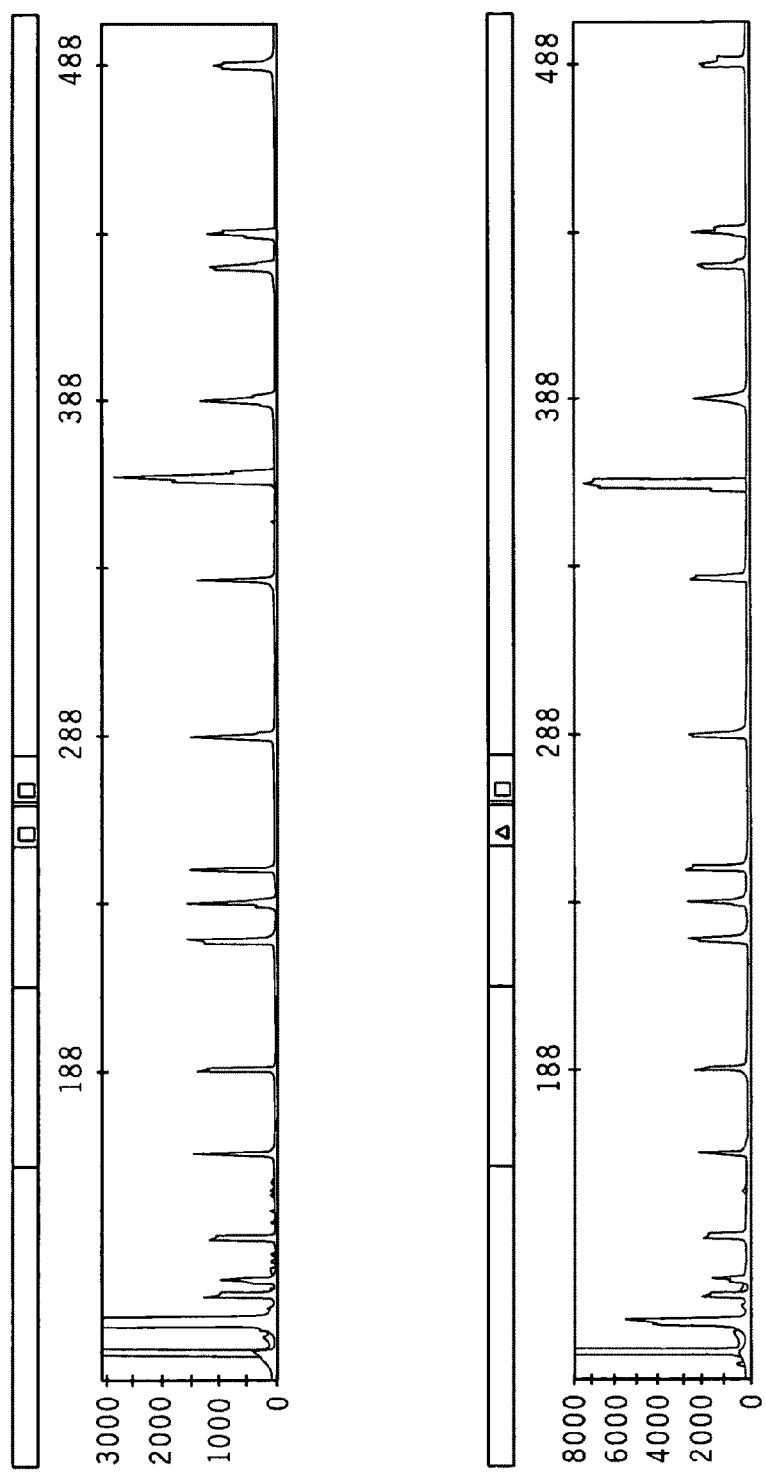
Figure 31C:
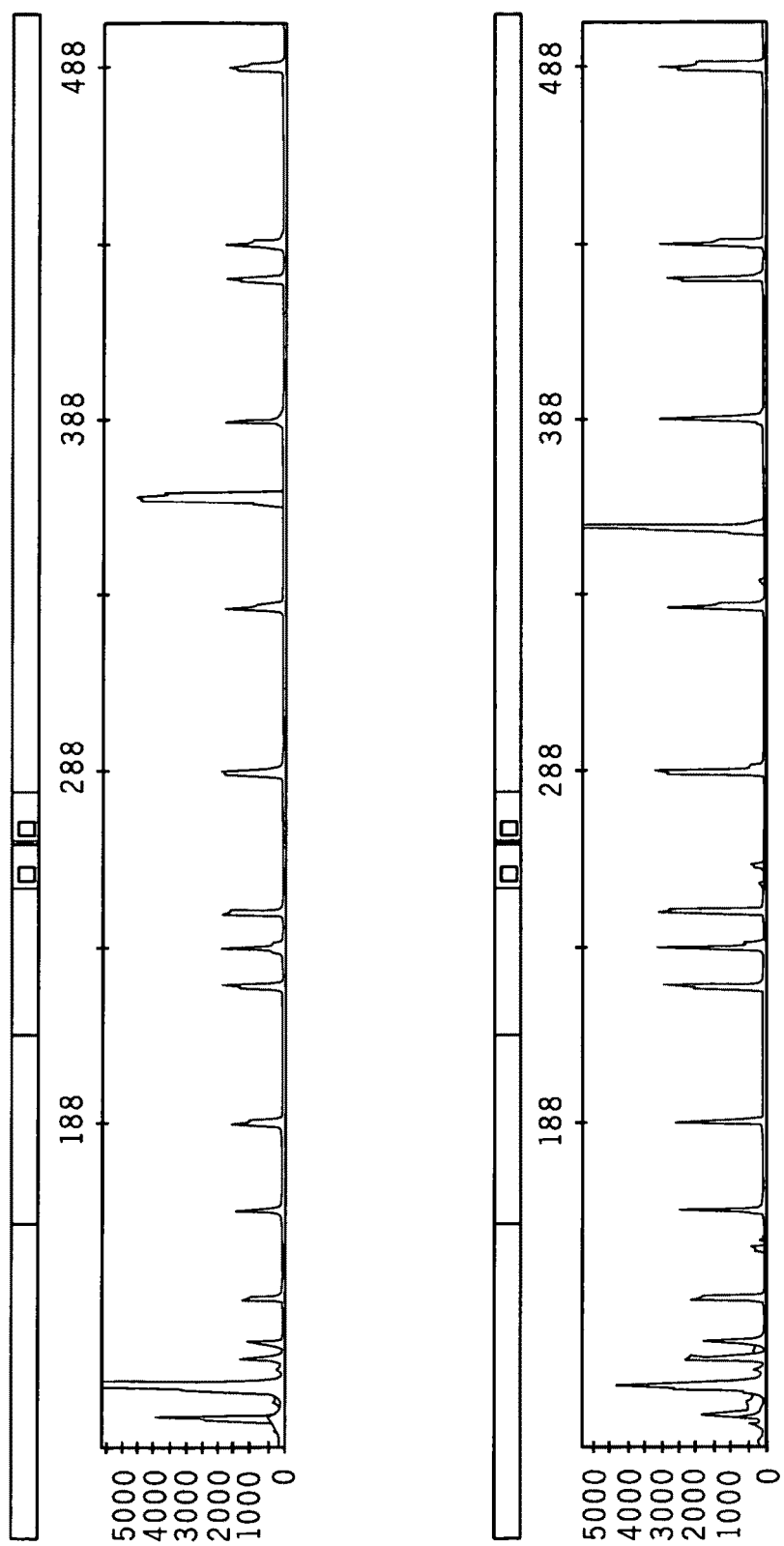
Figure 31D:
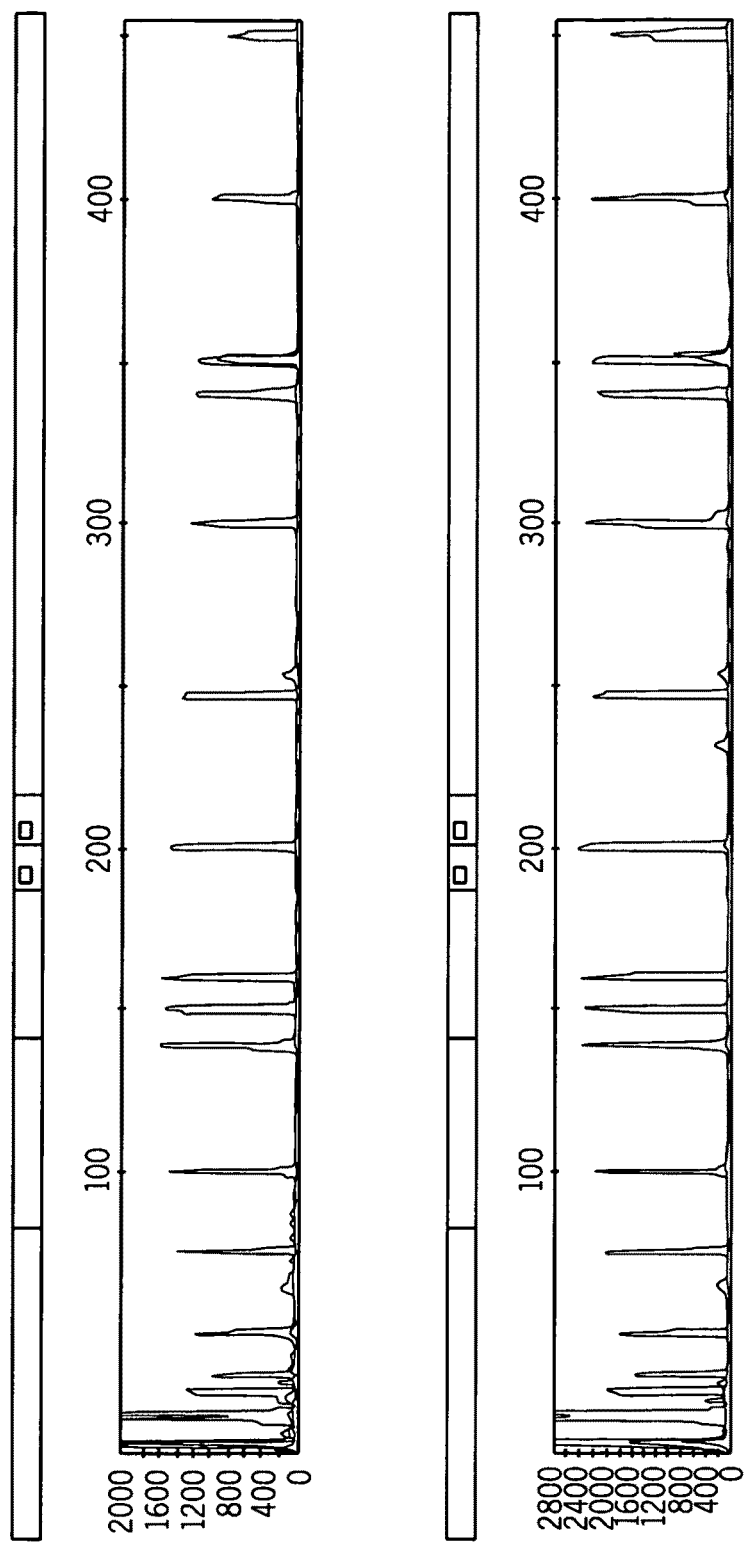
Figure 31E:
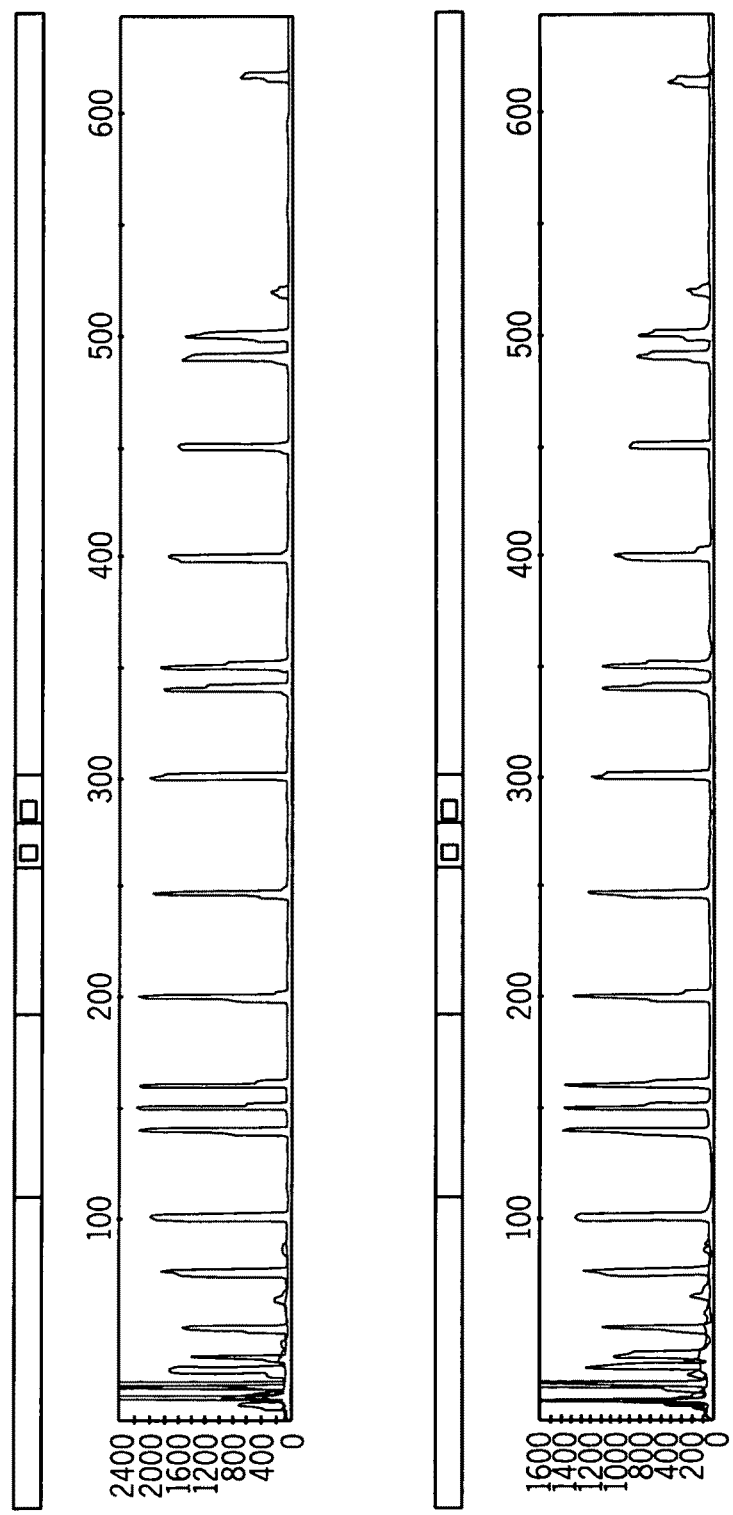
Figure 31F:
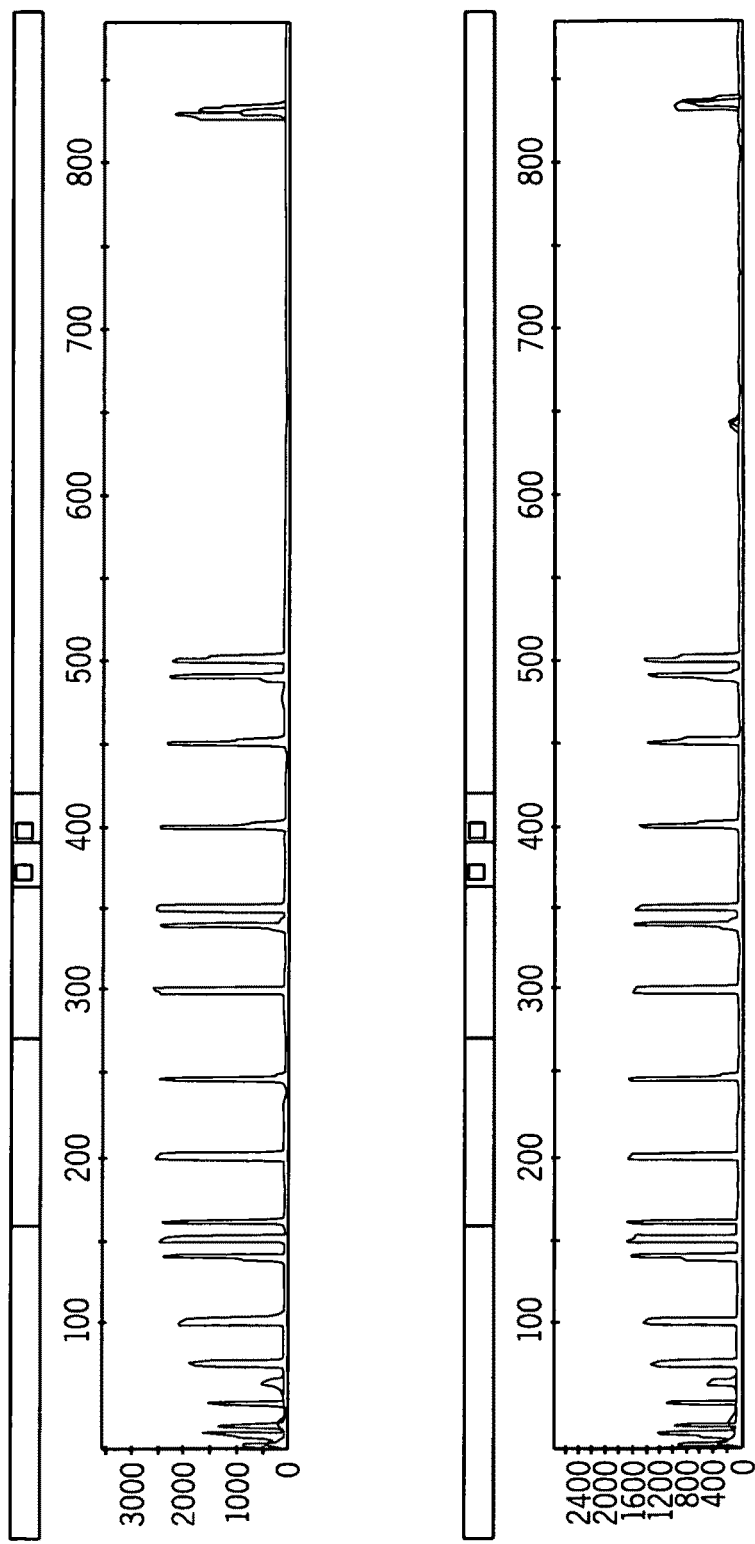
Figure 31F:
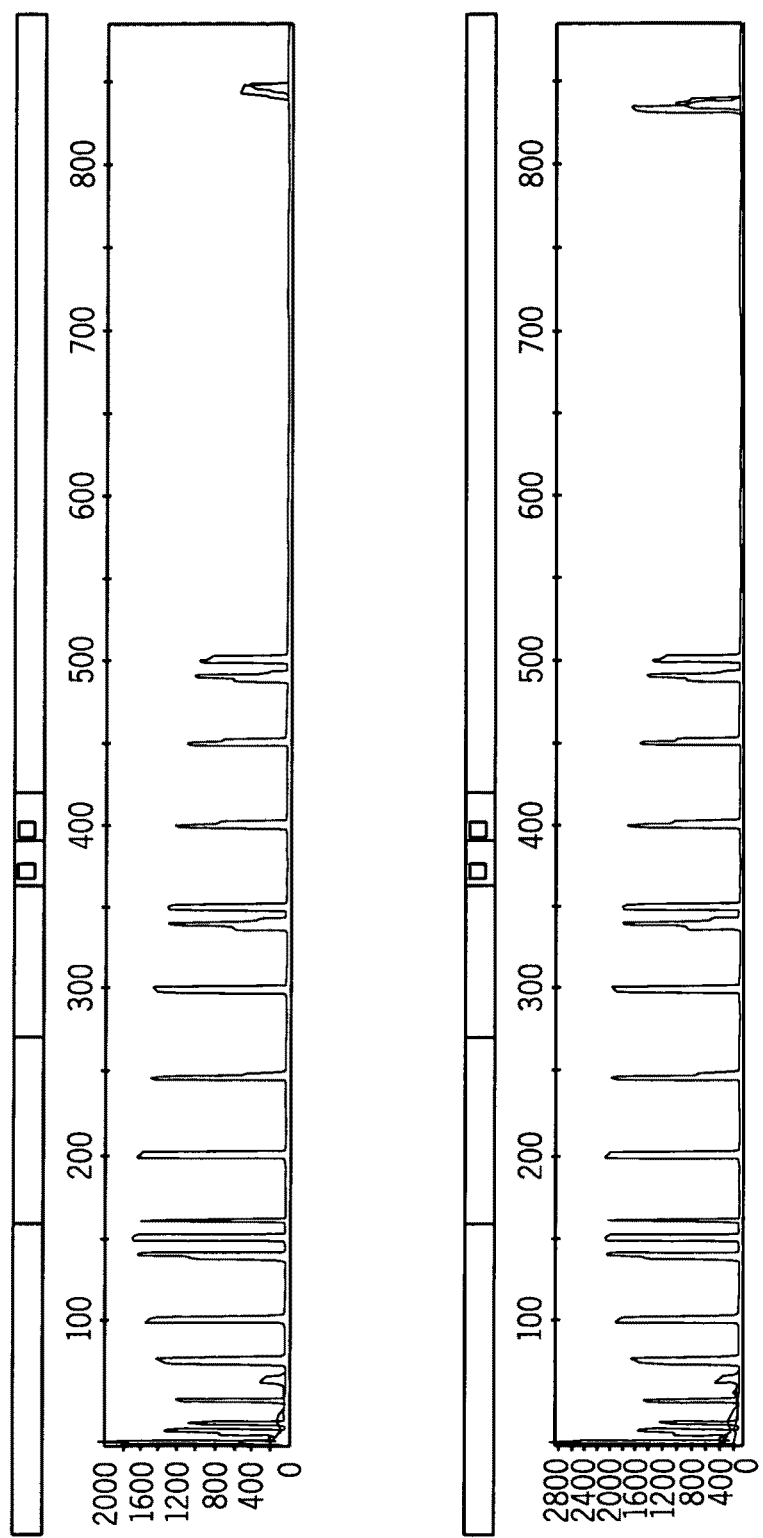

FIGS. 31Aa-Fb shows C.E fragment analysis after PCR reactions during the P53 library construction method as performed above. FIGS. 31Aa-Ad show the results with regard to P53 library construction level 1, while FIGS. 31Ba-E show the results with regard to levels 2-5, respectively. FIGS. 31Fa-Fb show P53 library construction level 6 with all 6 variants of the P53 library completed.

Error correction of libraries can be further economized. For example, in the construction of a library with 256 members (FIG. 29A above) a subset of only four clones containing all library components (FIG. 29B above) can be constructed and error corrected. Then, all 256 members of the library are constructed from these four error-free corrected clones.

Materials and methods were as described above for GFP synthesis.

Figure 32A:
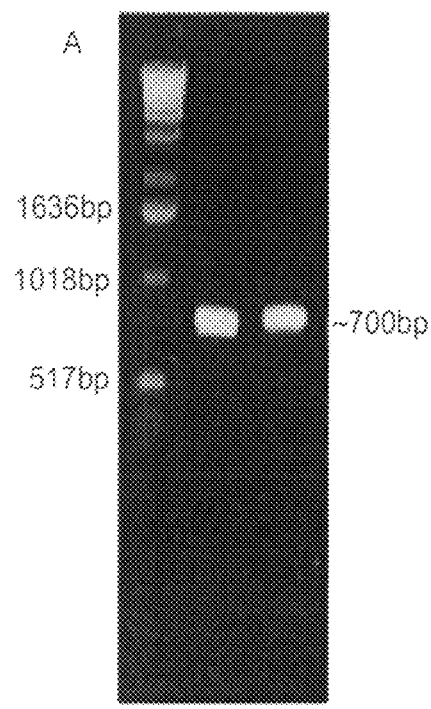
FIG. 32A-C shows a gel analysis after PCR reactions.
Figure 32B:
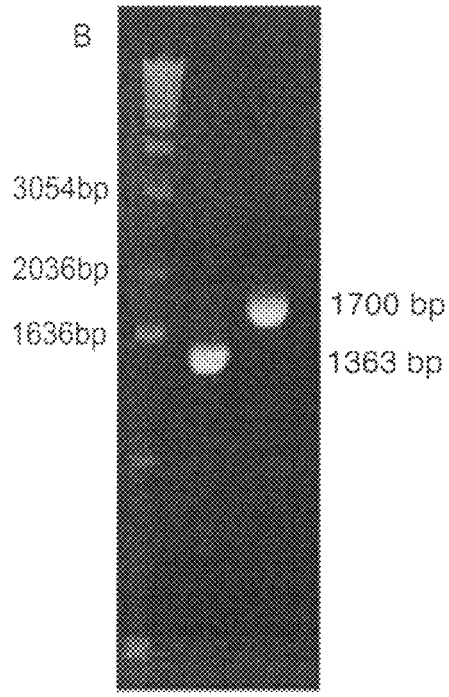
Figure 32C:
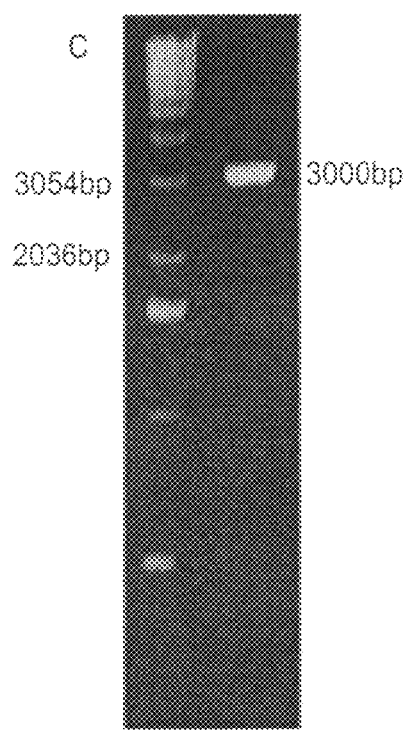

FIG. 32 shows composition of natural and synthetic fragments. FIG. 32A shows a PCR product of two 700 bp fragments. FIG. 32B shows a PCR product of 1363 bp composed of the fragments from A & a 1700 bp fragment from a natural plasmid. FIG. 32C shows a PCR product of a 3000 bp fragment composed of the fragments from B.

Figure 33:
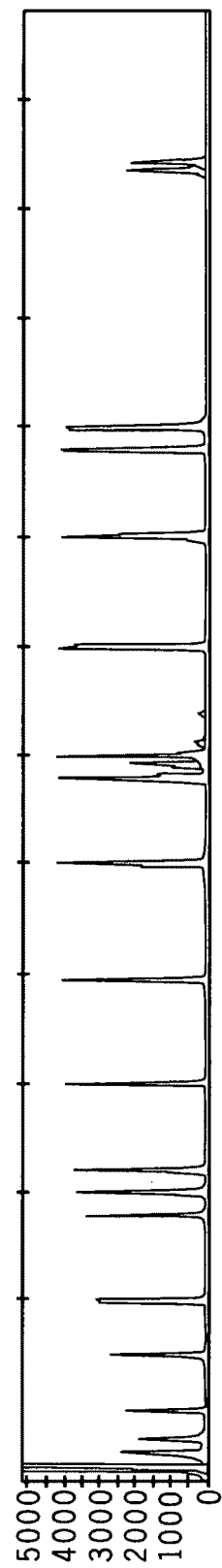
FIG. 33 shows C.E. fragment analysis of an example of an elongation reaction.

FIG. 33 shows C.E. fragment analysis of an example of an elongation reaction. One strand is labeled by HEX (green) and second by FAM (blue). The elongated product is thus labeled by two fluorophores (far right). An excess of the strand labelled by HEX (green peak on the left) does not elongate.

Figure 34:
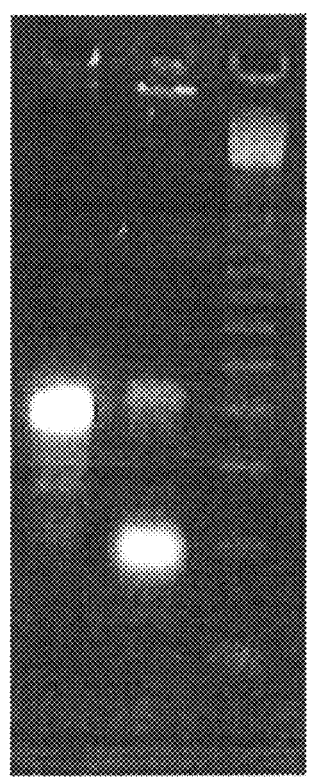
FIG. 34 shows an example of a lambda exonuclease reaction, generating ssDNA from dsDNA by lambda exonuclease.

FIG. 34 shows an example of a lambda exonuclease reaction, generating ssDNA from dsDNA by lambda exonuclease. Lane 1 shows dsDNA labelled with a 5' phosphate; while lane 2 shows the same DNA after treatment with lambda exonuclease, with a lower ssDNA band.

Example

Single Molecule PCR

In the process of error correction according to exemplary embodiments of the method of the present invention, the isolation and amplification of single DNA molecules can be performed with cloning into cells. Additionally, this can also be performed with single molecule PCR as described in this Example.

Single molecule PCR was performed by diluting the original template, which has one or more errors, to a concentration of less than one molecule per PCR reaction. Then a real time single molecule PCR reaction was performed as described in the methods section of the previous example for GFP synthesis (for PCR reactions using the BioLine machine), except that more thermal cycles are used for amplification (50 cycles). The number of single molecule amplifications required to achieve a minimal cut wa then calculated. The resulting PCR fragments were sequenced and error corrected according to the error correction method of the present invention.

Preparation of the DNA template for smPCR (single molecule PCR) was performed as follows. It is essential to avoid the annealing of DNA strands with different sequences since smPCR performed on such populations results in two populations of amplified DNA instead of one. This is the outcome of stationary phase annealing. Real-time PCR was used in order to monitor the amplification process and stop the template generating PCR from reaching the stationary phase (results are shown below). This provides assurance that both strands of a dsDNA molecule from this reaction have the same sequence. For experiments in which this method was not used, the sequencing results after amplification showed that the chromatogram converts from that of a single population to that of more than one population at the same base pair (data not shown). This means that at the insertion site of the populations were no longer synchronized, but rather shifted by one base pair. This result is obtained because the two strands comprising the dsDNA molecule, that was amplified and then sequenced, were not identical in sequence.

Figure 35:
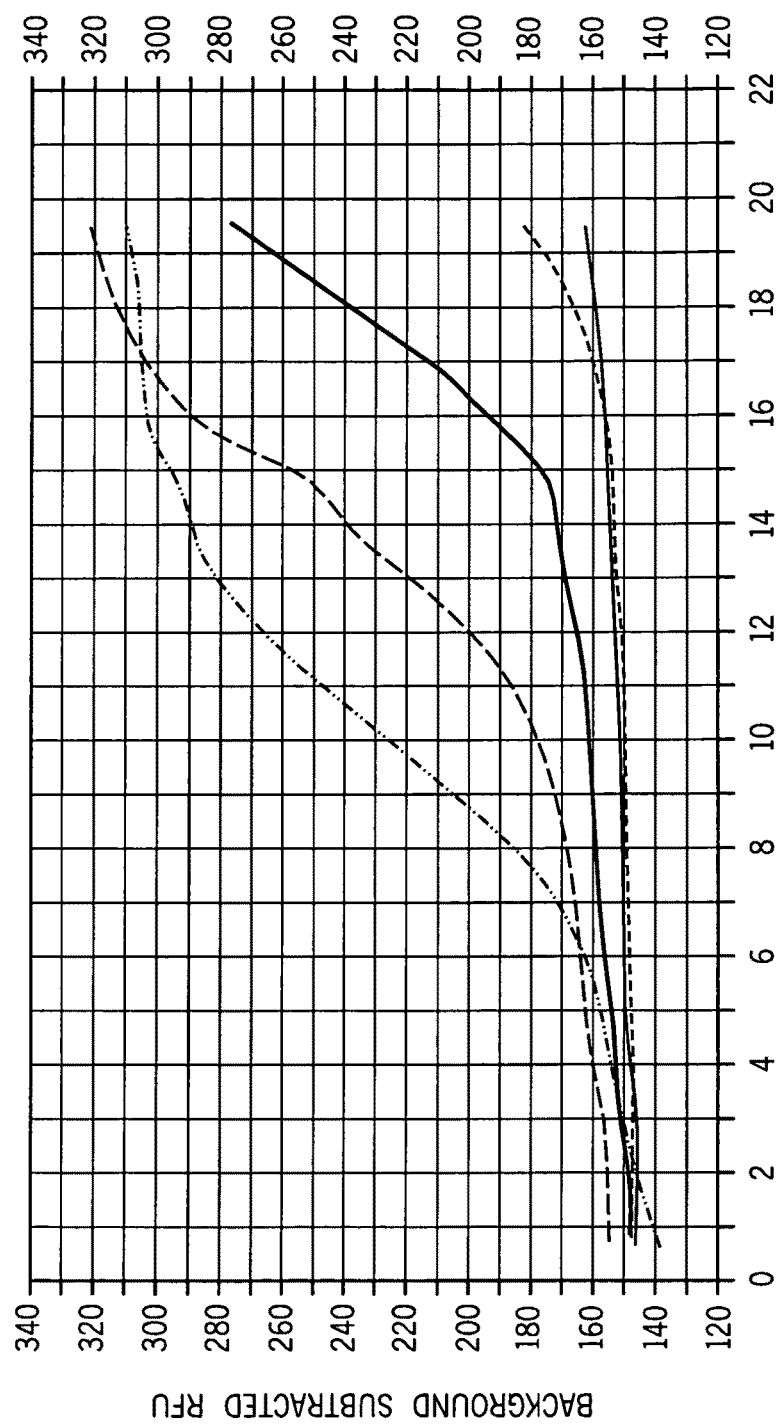
FIG. 35 relates to real time monitoring of the PCR amplification process showing that a single population is used for the smPCR.

FIG. 35 relates to real time monitoring of the PCR amplification process showing that a single population is used for the smPCR.

Figure 36:
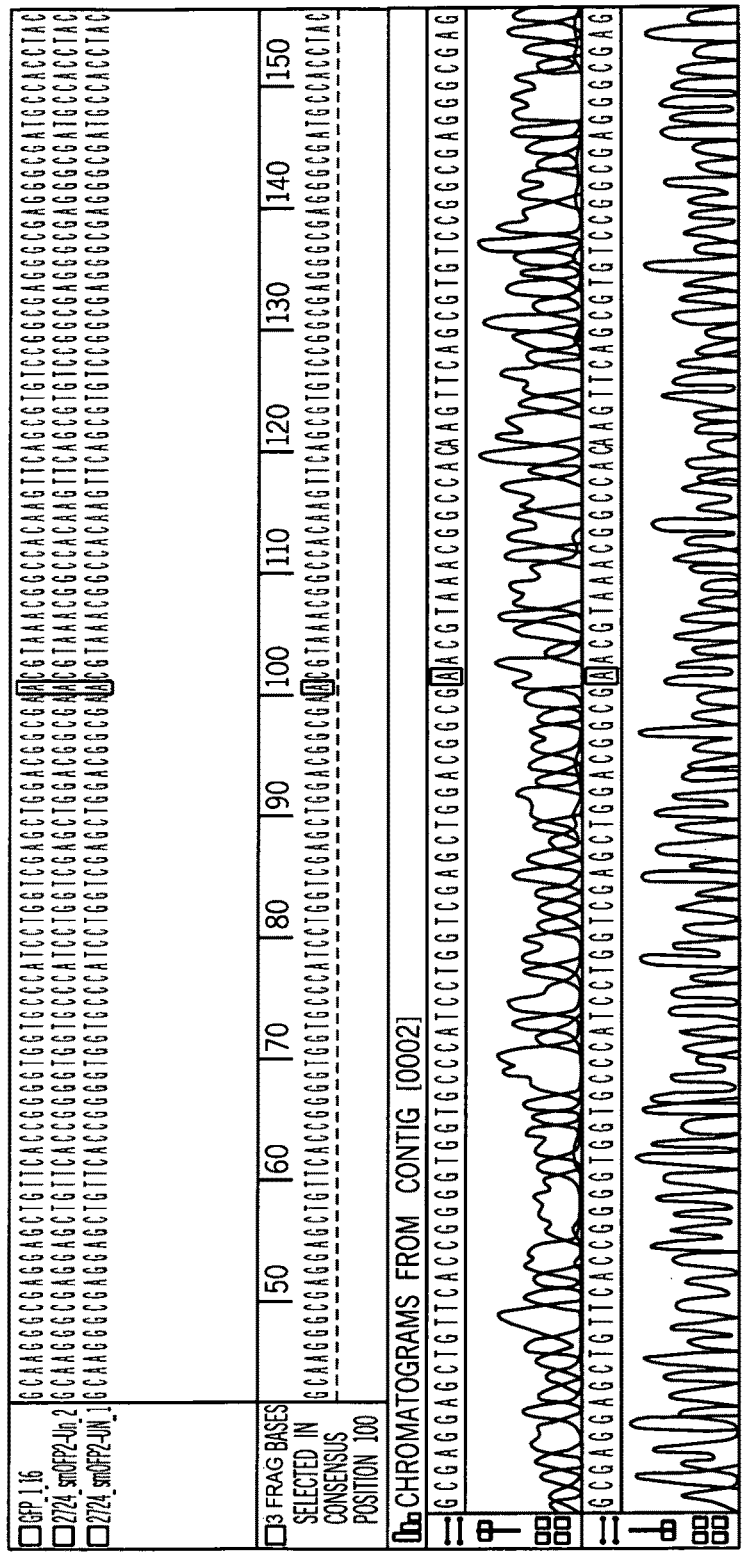
FIG. 36 relates to sequencing of a PCR reaction that started from one template DNA molecule with one sequence.

FIG. 36 relates to sequencing of a PCR reaction that started from one template DNA molecule with one sequence. Upper and lower sequences are reverse and forward sequencing reactions of the same template. Notice that although the sequence does contain a mutation (insertion of A) compared to the original sequence, both strands continue to exhibit a normal sequencing chromatogram. This result is obtained because the PCR reaction started with one template DNA molecule and therefore all of the DNA molecules sequenced have the same sequence.

Figure 37A:
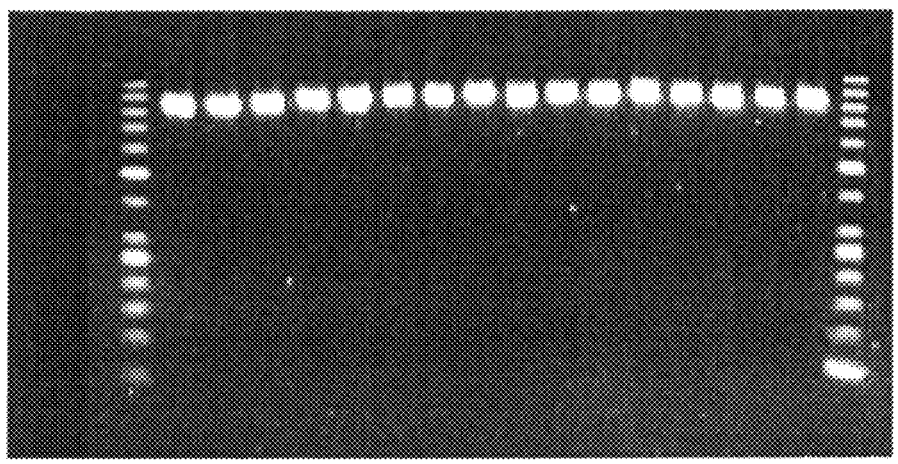
FIG. 37A shows a positive control containing more that one molecule per reaction.
Figure 37B:
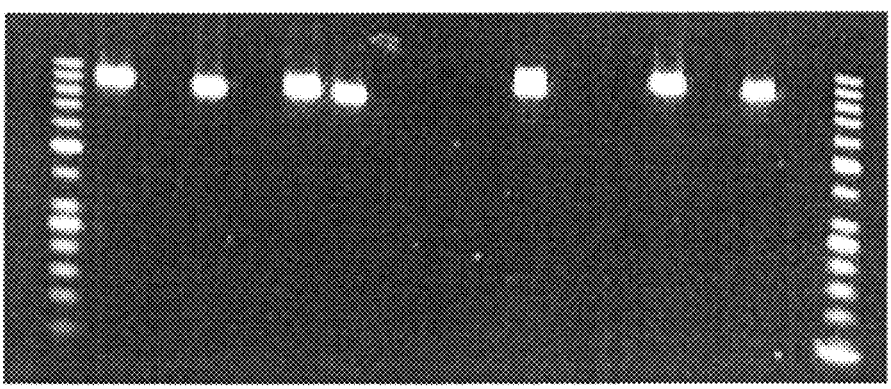
FIG. 37B shows PCR of the GFP gene with a concentration of 0.5 molecules per PCR reaction.

FIG. 37 shows gel electrophoresis of DNA from single molecule PCR with recursively constructed synthetic gene that codes for GFP as template. FIG. 37A shows a positive control containing more that one molecule per reaction. FIG. 37B shows PCR of the GFP gene with a concentration of 0.5 molecules per PCR reaction.

Example

DNA Synthesis on a Chip

DNA synthesized on chips may optionally be used as building blocks in some embodiments of the construction protocol according to the present invention. Release of DNA building blocks from the chip in a controlled manner, such that each and every sequence on the chip can be removed or copied from the chip individually is essential. This can be done by creating a specific "address" for every sequence on the chip. This can be done in different ways, including but not limited to, photo-cleavable moieties on the DNA can be activated and cleaved by light directed to a specific DNA sequence on the chip; chemical cleavage of cleavable moieties on the DNA with directed by printing technology to a specific DNA sequence on the chip; and specific DNA sequences on the chip can be amplified by using a combination of PCR primers that specifically amplify only that sequence from all the sequences present on the chip. Of course any of the above methods could optionally be performed as is known in the art.

Section 2—Polymers

Without wishing to be limited in any way, this Section relates to exemplary, illustrative embodiments of the present invention (method and system) with regard to construction of polymers other than biopolymers. It should be noted that the embodiments of the present invention described above with regard to biopolymers may optionally and preferably be extended to polymers, with the only changes required being in the type of reactions required for the synthetic chemistry. A complete description and definition of many different types of polymeric reactions and definitions of polymers is provided in K. Horie et al, Pure Appl. Chem. 76(4), 889-906, 2004, hereby incorporated by reference as if fully set forth herein. Briefly, some types of polymeric chemical reactions include but are not limited to, chemical amplification and cross-linking. Chemical polymeric units can for example be reacted together in order to form longer polymeric chains under defined chemical conditions. The recursive construction method according to the present invention may optionally be used by starting with shorter polymeric building blocks and recursively constructing longer polymers. Optionally chemical modification of the resultant polymer and/or portions thereof may be performed as well, as is known in the art.

Apparatus known for large scale chemical synthesis may also optionally be used with the present invention; for example U.S. Pat. No. 5,529,756 (which is hereby incorporated by reference as if fully set forth herein) describes a method for large scale chemical synthesis by using an array. U.S. Pat. No. 6,045,755 (which is hereby incorporated by reference as if fully set forth herein) describes a method for combinatorial chemical synthesis, which could optionally be combined with the methods of the present invention for synthesizing a polymer library for example.

Section 3—Apparatus for the System and Method of the Presnet Invention

Figure 38:
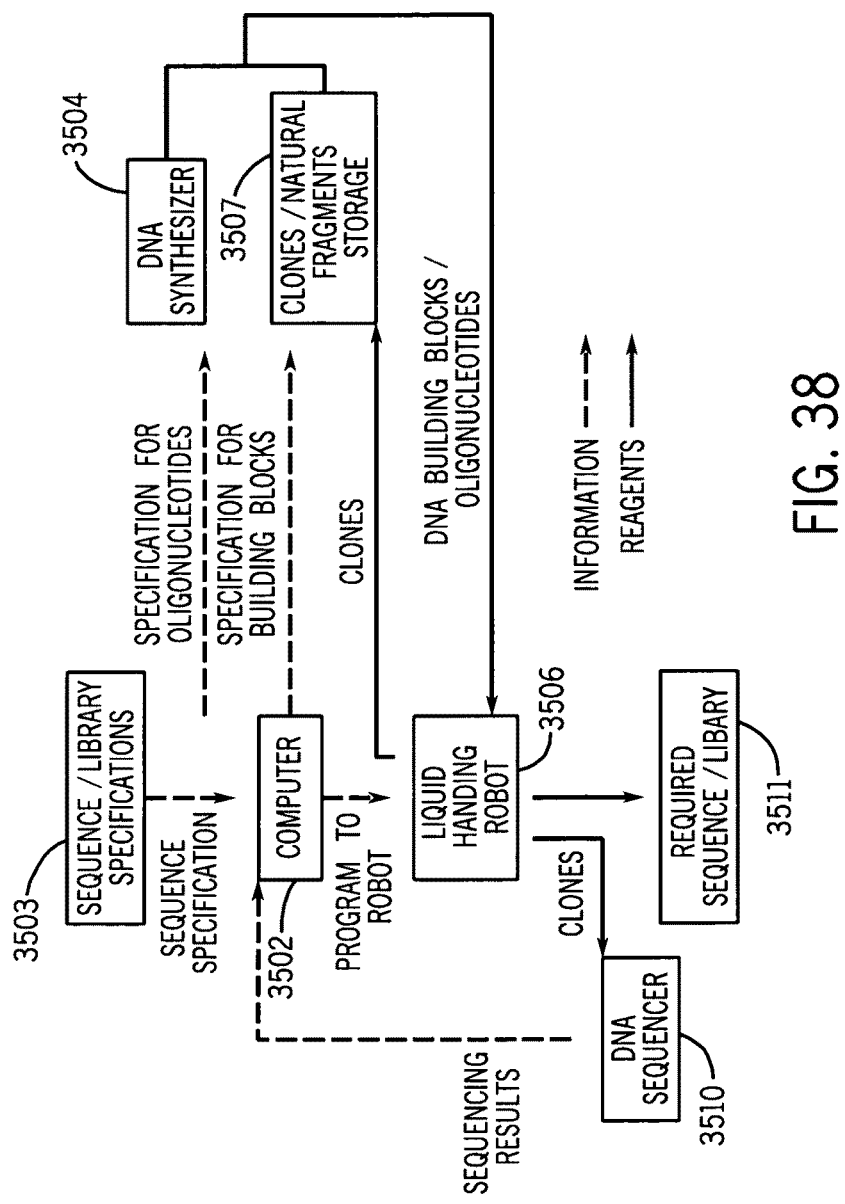
FIG. 38 shows an exemplary automated system according to the present invention.

This Section relates to a plurality of different exemplary, illustrative embodiments of an apparatus for implementing various embodiments of the system and method of the present invention. FIG. 38 is a detailed flow diagram implementation in a given architecture according to an exemplary embodiment of the present invention, while FIGS. 39-42 are generalized architectural illustrations of some possible, illustrative, exemplary embodiments of machines according to the present invention.

FIG. 38 shows an exemplary automated system according to the present invention. As shown, a system 3500 preferably features a computational device 3502 which receives the sequence and/or library specifications 3503 for the sequence and/or library to be synthesized. Computational device 3502 then determines the process for construction, which is preferably hierarchical and which is more preferably determined according to the minimal cut algorithm described herein. Computational device 3502 then preferably sends instructions for oligonucleotide synthesis to an appropriate synthesizer 3504. Alternatively or additionally, computational device 3505 can also optionally identify building blocks from other sources (e.g. previously constructed DNA and\or naturally existing DNA for use in the synthetic process).

Computational device 3502 also preferably sends the required program to a synthesizing robot 3508, which also receives the synthesized building blocks from synthesizer 3504 and\or optionally or alternatively from other sources as described above which may optionally be stored in a storage 3507. Synthesizing robot 3508 then synthesizes the required sequence and/or library, which is preferably checked for accuracy by a sequencer 3510. The required sequence and/or library is then preferably stored in an output storage 3511. Informational flows are shown with arrows having dashed lines, while the flow of reagents and/or physical material is shown with arrows having solid lines.

Figure 39:
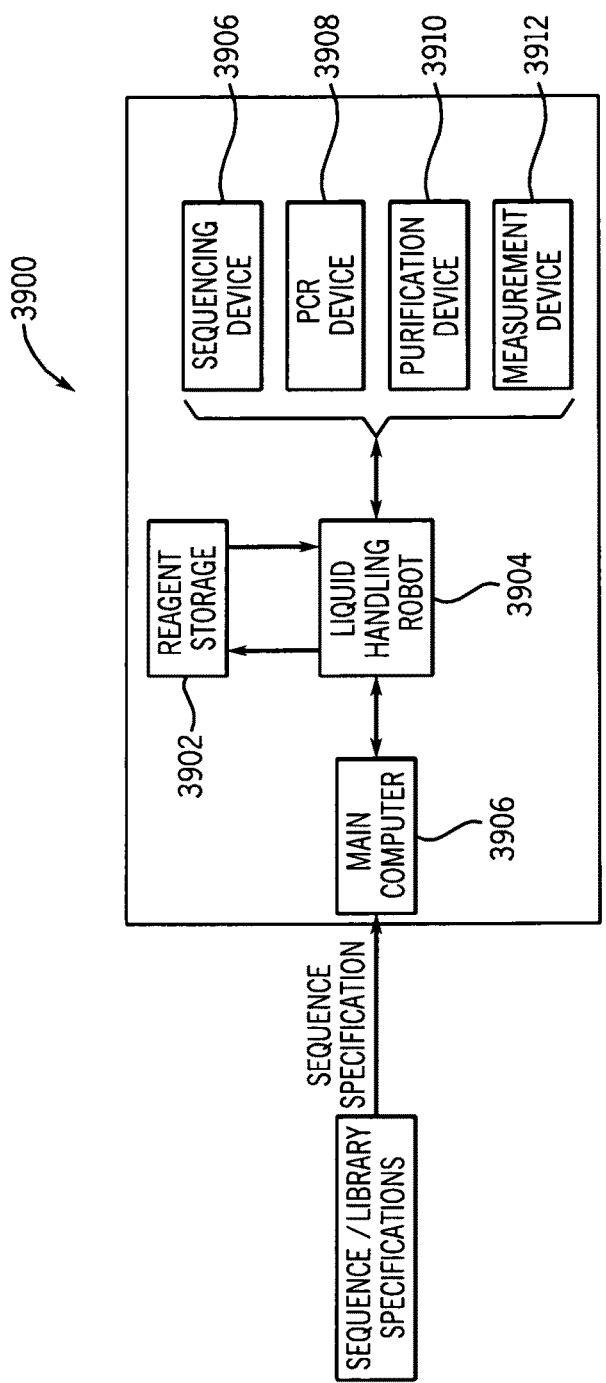
FIG. 39 shows a first illustrative embodiment of an apparatus according to the present invention, showing an apparatus 3900.

FIG. 39 shows another illustrative embodiment of an apparatus according to the present invention, showing an apparatus 3900. The process of operation optionally and preferably starts with reagents at a reagent storage 3902 which communicates with a liquid handling robot 3904. Reagents may be obtained from or placed into reagent storage 3902 by liquid handling robot 3904. The operations of liquid handling robot 3904 are preferably controlled by a computer 3906 which is more preferably operating software according to previously described methods of the present invention for polynucleotide synthesis. Computer 3906 preferably receives information regarding the sequence(s) to be constructed and then performs one or more methods as described herein for determining recursive construction of a polynucleotide, optionally and more preferably with error correction. The liquid handling robot 3904 preferably communicates with a sequencing device 3906, a PCR device 3908, a purification device 3910 and a measurement device 3912 for directing the performance of the synthetic process. For example, assuming the synthetic process comprises a plurality of subprocesses, optionally and preferably each subprocess includes PCR amplification with PCR device 3908, optionally followed by sequencing with sequencing device 3906 to look for one or more errors (alternatively and optionally, sequencing is performed at the end of the synthetic process, and/or after a plurality of subprocesses have been performed but before the synthetic process is complete). Purification device 3910 may optionally be used between the performance of subprocesses (for example if sequencing is optionally performed between subprocesses) but alternatively is optionally performed after the one or more sequences have been synthesized (and/or after a plurality of subprocesses have been performed but before the synthetic process is complete). Measurement device 3912 is preferably used during the synthetic process to monitor the amount of polynucleotide being synthesized.

Figure 40:
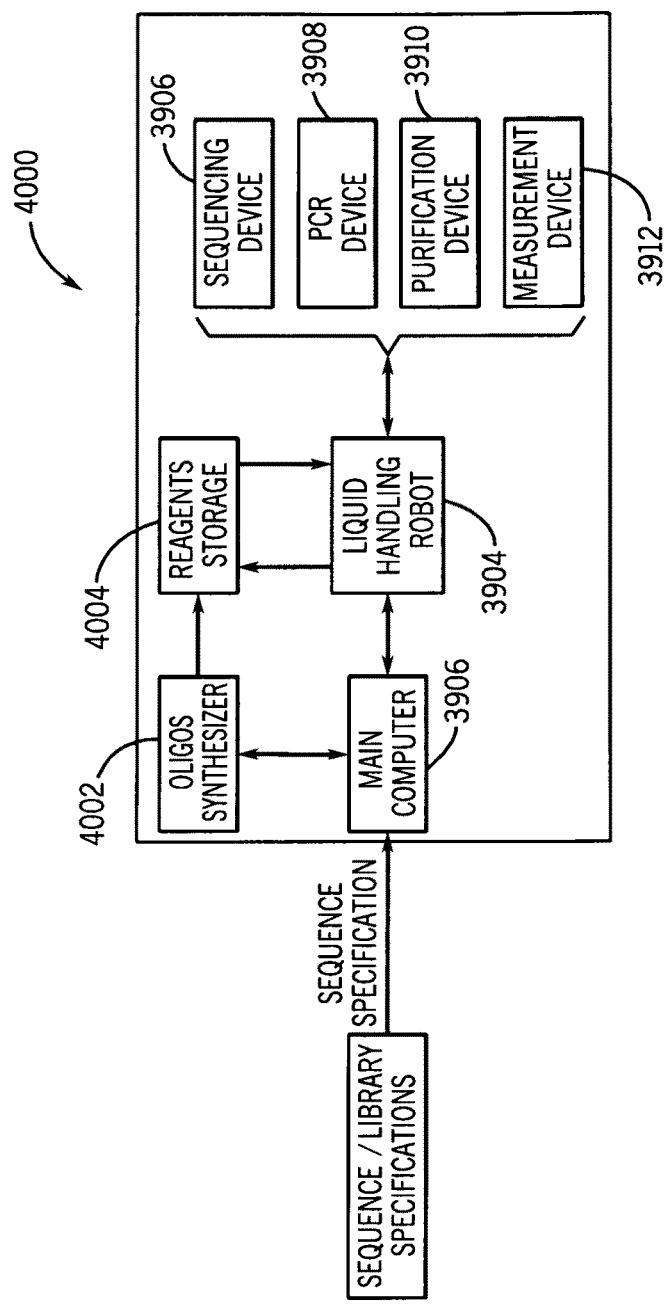
FIG. 40 shows another optional embodiment, which relates to an apparatus configuration with OLIGOS synthesizer component.

FIG. 40 shows another optional embodiment, which relates to an apparatus configuration with an oligonucleotide synthesizer component. An apparatus 4000 features many of the same and/or similar components as for FIG. 39, except that an oligonucleotide synthesizer 4002 is also included; reagent storage 4004 is optionally and preferably configured to support storage of such oligonucleotides.

Figure 41:
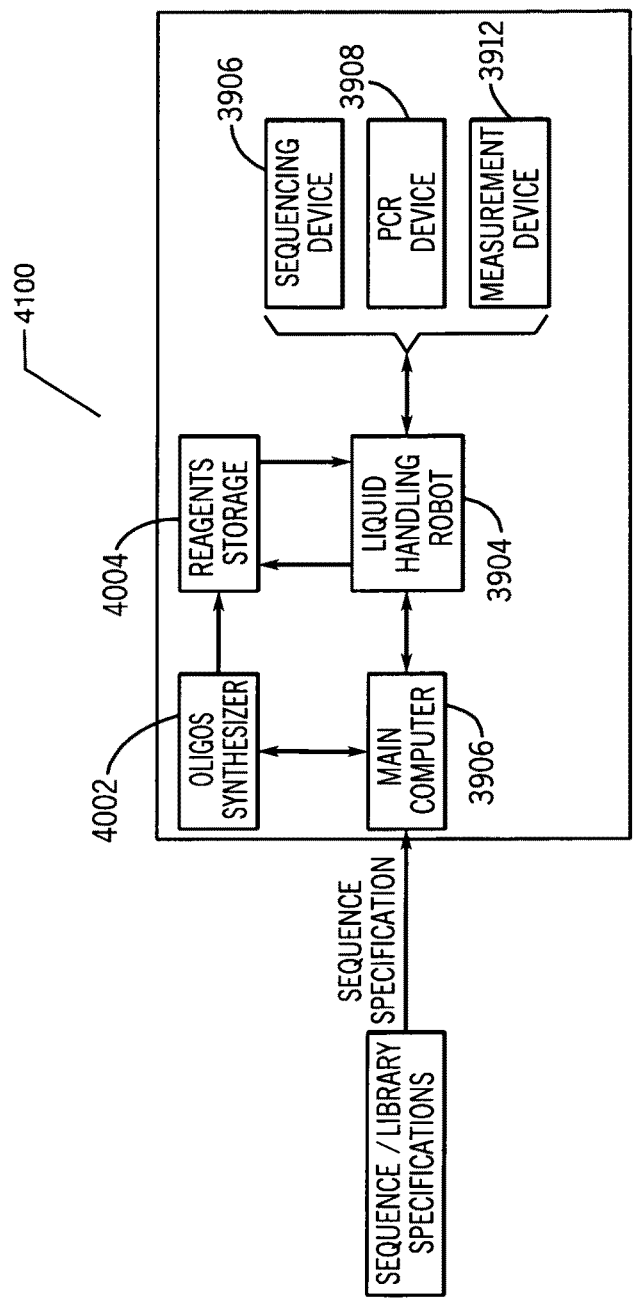
FIG. 41 relates to an apparatus configuration with solid support.

FIG. 41 relates to an apparatus configuration with solid support, which is highly similar to that of FIG. 41, except that now apparatus 4100 preferably lacks a separate purification device, as all purification is preferably performed on the solid support to which the DNA is attached, as is known in the art.

Figure 42:
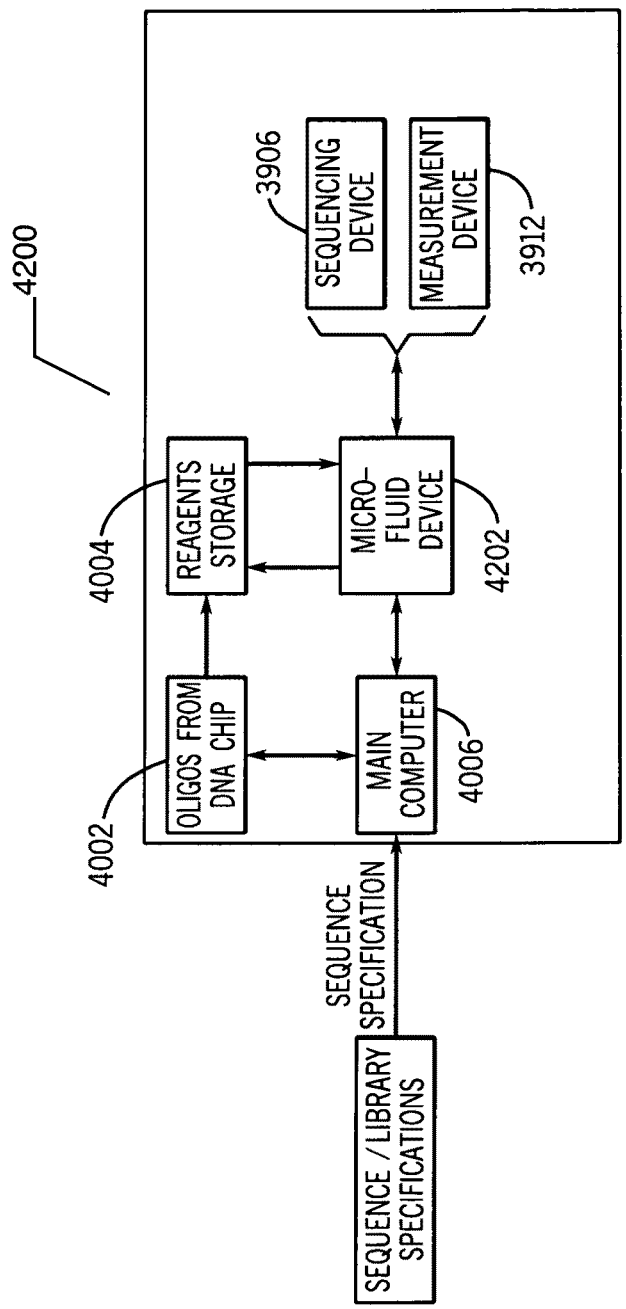
FIG. 42 relates to an apparatus configuration with microfluidics and DNA chips.

FIG. 42 relates to an apparatus configuration with microfluidics and DNA chips. The methods for DNA chip synthesis described above may optionally be used here as well. In addition, methods and devices for micro-fluidics are described in Whitesides, G. M. The origins and the future of microfluidics. Nature 442, 368-373 (2006), which is hereby incorporated by reference as if fully set forth herein. Again this apparatus is similar to the configuration of FIG. 40, except that in place of a liquid handling robot, a micro-fluidic device 4202 is preferably provided, which operates as is known in the art. Also the apparatus optionally and preferably lacks a separate PCR device.

For the different embodiments of the apparatus shown in FIGS. 39-42, each such apparatus may optionally and preferably be implemented as a small, portable or even miniature device. Also, for each such apparatus above, control is preferably provided by computer 3906. Communication between computer 3906 and either liquid handling robot 3904 or micro-fluidic device 4202, is preferably bidirectional. Such bidirectional communication preferably provides feedback for the proper operation of the construction process and for quantity and quality control during the construction process.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES

Goeden-Wood N L, Conticello V P, Muller S J, Keasling J D. Improved assembly of multimeric genes for the biosynthetic production of protein polymers. Biomacromolecules. 2002 July-August; 3(4):874-9.

Stemmer W P, Crameri A, Ha K D, Brennan T M, Heyneker H L. Single-step assembly of a gene and entire plasmid from large numbers of oligodeoxyribonucleotides. Gene. 1995 Oct. 16; 164(1):49-53.

Stahl S, Hansson M, Ahlborg N, Nguyen T N, Liljeqvist S, Lundeberg J, Uhlen M. Solid-phase gene assembly of constructs derived from the *Plasmodium falciparummalaria* blood-stage antigen Ag332. Biotechniques. 1993 March; 14(3):424-34.

Hostomsky Z, Smrt J, Arnold L, Tocik Z, Paces V. Solid-phase assembly of cow colostrum trypsin inhibitor gene. Nucleic Acids Res. 1987 Jun. 25; 15(12):4849-56.

Caruthers M H. Gene synthesis machines: DNA chemistry and its uses. Science. 1985 Oct. 18; 230(4723):281-5.

SantaLucia J Jr. A unified view of polymer, dumbbell, and oligonucleotide DNA nearest-neighbor thermodynamics. Proc Natl Acad Sci USA. 1998 Feb. 17; 95(4):1460-5.

What is claimed is:

1. A method for at least semi-automatically manufacturing a biopolymer, comprising:

a. analyzing the biopolymer to be constructed to determine a plurality of potentially faulty subcomponents for collectively defining the biopolymer; wherein said subcomponents are selected from the group consisting of nucleotides, polynucleotide, oligonucleotide, double stranded or single stranded DNA or RNA, a synthetic gene, an oligonucleotide of at least about 100 bases in length, an oligonucleotide of at least about 200 bases in length, an oligonucleotide of at least about 400 bases in length, or combinations thereof;

b. determining a hierarchical process for recursively constructing the biopolymer from said potentially faulty subcomponents, said determining comprising decomposing said hierarchical process into a plurality of sub-processes by searching for an optimal and valid division point of said hierarchical process, and then selecting an optimal set of sub-processes to construct the biopolymer for said hierarchical process, said hierarchical process comprising a plurality of stages, each stage comprising a plurality of sub-processes such that an output of said sub-processes of said stage is a plurality of sub-components to be combined as an output of said stage, wherein said output of a previous stage is an input to a subsequent stage of said hierarchical process, wherein a first stage and a first plurality of sub-processes are defined according to said division point, which determines a starting point for said hierarchical process, such that all subsequent stages and sub-processes are determined according to said first stage and said first plurality of sub-processes; wherein said sub-processes are collectively optimized and wherein at least one sub-process for combining a plurality of subcomponents is selected according to one or more criteria selected from the group consisting of: time, energy input, by-products, monetary expense, number of subcomponents, sub-processes required, and any combination thereof, wherein said valid division point is at least partially determined according to at least one constraint selected from the group consisting of availability of at least one subcomponent, characterization of at least one subcomponent and cost of performing an associated sub-process; wherein said hierarchical process is determined at least partially according to an optimal protocol wherein said optimal protocol is determined based on a set of constraints and a set of cost parameters wherein said set of constraints comprises a plurality of subcomponents to be synthesizable as oligo-primers, size of oligonucleotides, number of oligonucleotides, number of reactions, number of sub-processes, number of levels in the construction hierarchy, availability of oligonucleotides having defined sequences, and use of natural DNA or RNA; and c. constructing a set of instructions for assembling the biopolymer according to said plurality of potentially faulty subcomponents and according to said hierarchical process; and d. recursively constructing the biopolymer according to said set of instructions from a plurality of subcomponents, wherein at least one subcomponent has an error and wherein at least one sub-process of said hierarchical process corrects said error providing a final biopolymer product not featuring an error, wherein said biopolymer is a polynucleotide or oligonucleotide;

wherein said subcomponents comprise single stranded DNA and at least one oligonucleotide primer, and said plurality of sub-processes comprise elongation, phosphorylation and degradation by a DNA degrading enzyme, such that said recursively constructing the biopolymer comprises performing an elongation reaction with two input overlapping ssDNA fragments to form a dsDNA; phosphorylating a primer at the 5' end; amplifying the dsDNA with said primer; and degrading said phosphate-labeled PCR strand with said DNA degrading enzyme, yielding an elongated ssDNA fragment as output; wherein said stages are repeated to form said biopolymer.

2. The method of claim 1, wherein said at least one sub-process for correcting said error combines a plurality of erroneous subcomponents, together having a complete set of error free parts.

3. The method of claim 1, further comprising constructing a library of biopolymers.

4. The method of claim 1, wherein said biopolymer is manufactured or synthesized automatically.

5. The method of claim 1 wherein said determining said hierarchical process further comprises:
   determining an efficient path for recursively constructing the final cut from said first stage and said first sub-processes according to a branch and bound algorithm.

6. The method of claim 5, wherein said analyzing further comprises constructing each subcomponent separately.

7. The method of claim 3 for constructing a library of final biopolymers, further comprising:
   a. Analyzing the plurality of final biopolymers to detect at least one shared subcomponent between the final biopolymers; and
   b. Determining a recursive, hierarchical construction process with a minimal number of sub-processes by using said at least one shared subcomponent.

8. The method of claim 1, wherein said two input overlapping ssDNA fragments comprise two oligonucleotide primers the first time said stages are performed.

9. The method of claim 8, wherein said recursively constructing the biopolymer according to set of instructions from said plurality of subcomponents comprises determining whether an error free ssDNA fragment is generated by a subprocess; if not, repeating said processes of elongation, phosphorylation and degradation with one or more potentially faulty subcomponents until said error free ssDNA fragment is generated.

* * * * *

SEQUENCE LISTING

<160> NUMBER OF SEQ ID NOS: 22

<210> SEQ ID NO 1
<211> LENGTH: 748
<212> TYPE: DNA
<213> ORGANISM: Artificial Sequence
<220> FEATURE:
<223> OTHER INFORMATION: synthetic

<400> SEQUENCE: 1
atgagtattc aacatttccg tgtccgtgtc gcccttattc cctttttgc ggcattttgc    60

| | |
|---|---:|
| cttcctgttt tgctcaccc agaaacgctg gtgaaaagta aagatgctg aagatcagtt | 120 |
| gggtgcacga gtgggttaca tcgaactgga tctcaacagc ggtaagatcc ttgagagttt | 180 |
| tcgccccgaa gaacgttttc caatgatgag catttaaagt tctgctatgt ggcgcggtat | 240 |
| tatcccgtat tgacgccggg caagagcaac tcggtcgccg catacactat tctcagaatg | 300 |
| acttggttga gtgctgccat aaccatgagt gataacactg cggccaacct tacttctgac | 360 |
| aacgatctgc agtgctgcca taaccatgag tgattaacac tgcggccaac ttacttctga | 420 |
| caacgatcgg aggaccgaag agctaaccgc ttttttgcac aacatggggg atcatgaact | 480 |
| cgccttgatc gttgggaacc ggagctgaat gaagccatac aaacgacga gcgtgacacc | 540 |
| acgatgcctg taggcgaact acttgcaatg caacaacgt tgcgcaaact attaactctc | 600 |
| tagcttcccg gccaacaatt aatagactgg atggaggcgg ataaagttgc aggaccactt | 660 |
| ctgcgctcgg cccttccggc tggctggtta ttgctgataa atctggagcc ggtgagcgtg | 720 |
| agcgtgggtc tcgcggtatc attgcagc | 748 |

<210> SEQ ID NO 2
<211> LENGTH: 247
<212> TYPE: DNA
<213> ORGANISM: artificial sequence
<220> FEATURE:
<223> OTHER INFORMATION: synthetic

<400> SEQUENCE: 2

| | |
|---|---:|
| gtcgccttat tccctttttt gcggcatttt gccttcctgt ttttgctcac ccagaaacgc | 60 |
| tggtgaaagt aaaagatgct gaagatcagt tgggtgcacg agtgggttac atcgaactgg | 120 |
| atctcaacag cggtaagatc cttgagagtt tcgccccga gaacgttttt ccaatgatga | 180 |
| gcatttaaa gttctgctat gtggcgcggt attatcccgt attgacgccg ggcaagagca | 240 |
| actcggt | 247 |

<210> SEQ ID NO 3
<211> LENGTH: 587
<212> TYPE: DNA
<213> ORGANISM: artificial sequence
<220> FEATURE:
<223> OTHER INFORMATION: synthetic

<400> SEQUENCE: 3

| | |
|---|---:|
| ggtaagatcc ttgagagttt cgccccgaa gaacgttttc caatgatgag cattttaaag | 60 |
| ttctgctatg tggcgcggta ttatcccgta ttgacgccgg gcaagagcaa ctcggtcgcc | 120 |
| gcaatacact attctcagaa tgacttggtt gagtgctgcc ataaccatga gtgataacac | 180 |
| tgcggccaac ttacttctga ccaacgatct gcagtgctgc cataaccatg agtgataaca | 240 |
| ctgcggccaa cttacttctg acaacgatcg gaggaccgaa ggagctaacc gcttttttgc | 300 |
| acaacatggg ggatcatgta actcgccttg atcgttggga accggagctg aatgaagcca | 360 |
| taccaaacga cgagcgtgac accaacgatg cctgtagcaa tggcaacaac gttgcgcaaa | 420 |
| ctattaactg gcgaactact tactctagct tcccggcaac aattaataga ctggatggag | 480 |
| gcggataaag ttgcaggacc acttctgcgc tcggcccttc cggctggctg gttattgctg | 540 |
| ataaatctgg agccggtgag cgtgggtctc gcggtatcat tgcagca | 587 |

<210> SEQ ID NO 4
<211> LENGTH: 307
<212> TYPE: DNA
<213> ORGANISM: artificial sequence

```
<220> FEATURE:
<223> OTHER INFORMATION: synthetic

<400> SEQUENCE: 4
cttgcccggc tcaatacggg ataataccgc gccacatagc agaactttaa aagtgctcat      60
cattggaaaa cgttcttcgg ggcgacttgc ccggctcaat acgggataat accgcgccac     120
atacgagaac tttaaaagtg ctcatcattg gaaaacgttc ttcggggcga gggataatac     180
cgcgccacat agcagaactt taaaagtgct catcattgga aaacgttct tcggggcgag      240 ggataatacc gcgccacata gcagaacttt aaaagtgctc atcattggaa aacgttcttc     300
ggggcga                                                                307

<210> SEQ ID NO 5
<211> LENGTH: 86
<212> TYPE: DNA
<213> ORGANISM: artificial sequence
<220> FEATURE:
<223> OTHER INFORMATION: synthetic

<400> SEQUENCE: 5
ctgccccgaa gaacgttttc caatgatgag cactttttaaa gttctgctat gtggcgcggt     60
attatcccgt attgacgccg ggcaag                                            86

<210> SEQ ID NO 6
<211> LENGTH: 87
<212> TYPE: DNA
<213> ORGANISM: artificial sequence
<220> FEATURE:
<223> OTHER INFORMATION: synthetic

<400> SEQUENCE: 6
tcgccccgaa gaaacgtttt ccaatgatga gcacttttaa agttctgcta tgtggcgcgg     60
tattatcccg tattgacgcc gggcaag                                          87

<210> SEQ ID NO 7
<211> LENGTH: 86
<212> TYPE: DNA
<213> ORGANISM: artificial sequence
<220> FEATURE:
<223> OTHER INFORMATION: synthetic

<400> SEQUENCE: 7
tcgccccgaa gaacgttttc caatgatgag cacttttaaa gttctgctat gtggcgcggt     60
attatcccgt attgacgccg ggcaag                                            86

<210> SEQ ID NO 8
<211> LENGTH: 86
<212> TYPE: DNA
<213> ORGANISM: artificial sequence
<220> FEATURE:
<223> OTHER INFORMATION: synthetic

<400> SEQUENCE: 8
tcgccccgaa gaacgttttc caatgatgag cacttttaaa gttctgctat gtggcgcggt     60
attatcccgt attgacgccg ggcaag                                            86

<210> SEQ ID NO 9
<211> LENGTH: 134
<212> TYPE: DNA
<213> ORGANISM: artificial sequence
<220> FEATURE:
```

```
<223> OTHER INFORMATION: synthetic

<400> SEQUENCE: 9
ttacatatcg aactggatct caacagcggt aagatcctga gagttttcgc cccgaagaac      60
gttttccaat gatgagcact tttaaagttc tgctatgtgg cgcggtatta tcccgtattg     120
acgccgggca agaa                                                       134

<210> SEQ ID NO 10
<211> LENGTH: 107
<212> TYPE: DNA
<213> ORGANISM: artificial sequence
<220> FEATURE:
<223> OTHER INFORMATION: synthetic

<400> SEQUENCE: 10
ggtaagatcc ttgagagttt tcgccccgaa gaacgttttc caatgatgag cacttttaaa      60
gttctgctat gggcgcggta ttatcccgta ttgacgccgg gcaagaa                   107

<210> SEQ ID NO 11
<211> LENGTH: 107
<212> TYPE: DNA
<213> ORGANISM: artificial sequence
<220> FEATURE:
<223> OTHER INFORMATION: synthetic

<400> SEQUENCE: 11
ggtaagagcc ttgagagttt tcgccccgaa gaacgttttc caatgtgagc acttttaaag      60
ttctgctatg tggcgcggta ttatcccgta ttgacgccgg gcaagaa                   107

<210> SEQ ID NO 12
<211> LENGTH: 137
<212> TYPE: DNA
<213> ORGANISM: artificial sequence
<220> FEATURE:
<223> OTHER INFORMATION: synthetic

<400> SEQUENCE: 12
tacatcgaac tggatctcaa cagcggtaag atccttgaga gttttcgccc cgaagattat      60
gtggcggcgg tattatcccg tattgacggc cgggcaagcg ttttccaatg atgagcactt     120
ttaaagttct gctatgc                                                    137

<210> SEQ ID NO 13
<211> LENGTH: 130
<212> TYPE: DNA
<213> ORGANISM: artificial sequence
<220> FEATURE:
<223> OTHER INFORMATION: synthetic

<400> SEQUENCE: 13
tacatcgaac tggatctcaa cagcggtaag atccttgaga gttttcgccc cgaagaacgt      60
ttccaatgat gagcactttt aaagttctgc tatgtggcgc ggtattatcc cgtattgacg     120
gccgggcaag                                                            130

<210> SEQ ID NO 14
<211> LENGTH: 132
<212> TYPE: DNA
<213> ORGANISM: artificial sequence
<220> FEATURE:
<223> OTHER INFORMATION: synthetic

<400> SEQUENCE: 14
```

```
tacatcgaac tggatctgaa cagcggtaag atccttgaga gttttcgccc cgaagaacgt      60
ttttccaatg atgagcactt ttaaagttct gctatgtggc gcggtattat cccgtattga     120
cggccgggca ag                                                         132
```

```
<210> SEQ ID NO 15
<211> LENGTH: 132
<212> TYPE: DNA
<213> ORGANISM: artificial sequence
<220> FEATURE:
<223> OTHER INFORMATION: synthetic

<400> SEQUENCE: 15
tacatcgaac tggatctcaa cagcggtaag atccttgaga gttttcgccc cgaagaacgt      60
tttccaatga tgagcacttt taaagttct gctatgtggc gcggtattat cccgtattga     120
cggccgggca ag                                                         132
```

```
<210> SEQ ID NO 16
<211> LENGTH: 131
<212> TYPE: DNA
<213> ORGANISM: artificial sequence
<220> FEATURE:
<223> OTHER INFORMATION: synthetic

<400> SEQUENCE: 16
tacatcgaac tggatctcaa cagcggtaag atccttgaga gttttcgccc cgaagaacgt      60
tttccaatga tgagcacttt taaagttctg ctatgtggcg cggtattatc ccgtattgac     120
ggccgggcaa g                                                          131
```

```
<210> SEQ ID NO 17
<211> LENGTH: 86
<212> TYPE: DNA
<213> ORGANISM: artificial sequence
<220> FEATURE:
<223> OTHER INFORMATION: synthetic

<400> SEQUENCE: 17
tcgccccgaa gaacgttttc catgatgagc acttttaaag ttctgctatg tggcgcggta      60
ttatcccgta ttgacggccg ggcaag                                           86
```

```
<210> SEQ ID NO 18
<211> LENGTH: 65
<212> TYPE: DNA
<213> ORGANISM: artificial sequence
<220> FEATURE:
<223> OTHER INFORMATION: synthetic

<400> SEQUENCE: 18
accggtcatg agattatcaa aaggatcttc acctagatc cttttaaatt aaaaatgaag      60
tttta                                                                  65
```

```
<210> SEQ ID NO 19
<211> LENGTH: 84
<212> TYPE: DNA
<213> ORGANISM: artificial sequence
<220> FEATURE:
<223> OTHER INFORMATION: synthetic

<400> SEQUENCE: 19
tcacctagat ccttttaaat taaaaatgaa gttttaaatc aatctaaagt atatatgagt      60
```

```
aaacttggtc tgacagttac caat                                          84

<210> SEQ ID NO 20
<211> LENGTH: 84
<212> TYPE: DNA
<213> ORGANISM: artificial sequence
<220> FEATURE:
<223> OTHER INFORMATION: synthetic

<400> SEQUENCE: 20
caggcaacta tggatgaacg aaatagacag atcgctgaga taggtgcctc actgattaag   60
cattggtaac tgtcagacca agtt                                          84

<210> SEQ ID NO 21
<211> LENGTH: 79
<212> TYPE: DNA
<213> ORGANISM: artificial sequence
<220> FEATURE:
<223> OTHER INFORMATION: synthetic

<400> SEQUENCE: 21
tcgttcatcc atagttgcct gactgcccgt cgtgtagata actacgatac gggagggctt   60
accatctggc cccagtgct                                                79

<210> SEQ ID NO 22
<211> LENGTH: 51
<212> TYPE: DNA
<213> ORGANISM: artificial sequence
<220> FEATURE:
<223> OTHER INFORMATION: synthetic

<400> SEQUENCE: 22
gaaacgattc cggtcgagac cttgcggtat cattgcagca ctggggccag a            51
```